US012558555B2

(12) United States Patent
Zaidi

(10) Patent No.: US 12,558,555 B2
(45) Date of Patent: Feb. 24, 2026

(54) MIXED-SEGMENT ELECTROCARDIOGRAM ANALYSIS IN COORDINATION WITH CARDIOPULMONARY RESUSCITATION FOR EFFICIENT DEFIBRILLATION ELECTROTHERAPY

(71) Applicant: ZOLL Medical Corporation, Chelmsford, MA (US)

(72) Inventor: Naveed Zaidi, Shrewsbury, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 665 days.

(21) Appl. No.: 17/456,746

(22) Filed: Nov. 29, 2021

(65) Prior Publication Data

US 2022/0168583 A1     Jun. 2, 2022

Related U.S. Application Data

(60) Provisional application No. 63/119,138, filed on Nov. 30, 2020.

(51) Int. Cl.
*A61N 1/39*       (2006.01)
*A61N 1/02*       (2006.01)
       (Continued)

(52) U.S. Cl.
CPC ......... *A61N 1/39044* (2017.08); *A61N 1/025* (2013.01); *A61N 1/3925* (2013.01);
       (Continued)

(58) Field of Classification Search
CPC .. A61N 1/39044; A61N 1/3987; A61N 1/025; A61N 1/3925; G16H 20/40; G16H 40/63
See application file for complete search history.

(56) References Cited

U.S. PATENT DOCUMENTS 6,553,257 B2     4/2003 Snyder et al.
7,463,922 B1 * 12/2008 Snyder ................... A61B 5/361
                                                                607/5

(Continued)

FOREIGN PATENT DOCUMENTS

WO       2014141080 A1     9/2014

OTHER PUBLICATIONS

International Search Report and Written Opinion for PCT Application No. PCT/US2021/072617 Date of Mailing: Mar. 21, 2022 (14 pages.

*Primary Examiner* — Lynsey C Eiseman
*Assistant Examiner* — Benjamin Allyn Schmitt
(74) *Attorney, Agent, or Firm* — Finch & Maloney PLLC

(57)       ABSTRACT

An external defibrillator includes therapy delivery circuitry configured to discharge electrotherapy to a patient, a chest compression sensor configured to acquire motion signals during and after administration of CPR to the patient, an ECG sensor configured to acquire ECG signals from the patient, and a processor coupled to the therapy delivery circuitry, the chest compression sensor, and the ECG sensor. The processor is configured to generate first ECG data from ECG signals acquired during a cycle of CPR, generate second ECG data from ECG signals acquired after the cycle of CPR, identify a plurality of temporally overlapping segments in the first ECG data, determine shock/no-shock guidance based on the plurality of temporally overlapping segments, confirm the shock/no-shock guidance based on the second ECG data, and control the therapy delivery circuitry to discharge the electrotherapy where the shock/no-shock guidance is confirmed to specify electrotherapy.

21 Claims, 30 Drawing Sheets

(51) Int. Cl.
  *G16H 20/40* (2018.01)
  *G16H 40/63* (2018.01)
(52) U.S. Cl.
  CPC ........... *A61N 1/3987* (2013.01); *G16H 20/40* (2018.01); *G16H 40/63* (2018.01)

(56) References Cited

U.S. PATENT DOCUMENTS

| | | | |
|---|---|---|---|
| 8,738,129 B2 | 5/2014 | Packer | |
| 9,126,055 B2 | 9/2015 | Abdeen et al. | |
| 9,168,385 B2 | 10/2015 | Snyder | |
| 9,283,400 B2 | 3/2016 | Sullivan et al. | |
| 9,409,034 B2 | 8/2016 | Babaeizadeh et al. | |
| 9,801,561 B2 | 10/2017 | Sullivan et al. | |
| 9,919,160 B2* | 3/2018 | Firoozabadi ........... | A61B 5/346 |
| 10,143,387 B2 | 12/2018 | Tan et al. | |
| 10,155,120 B2* | 12/2018 | Zaidi ................... | A61B 5/0245 |
| 10,314,504 B2* | 6/2019 | Albadawi .............. | A61B 5/339 |
| 10,335,604 B2 | 7/2019 | Gehman et al. | |
| 10,716,949 B2 | 7/2020 | Freeman | |
| 2011/0105930 A1* | 5/2011 | Thiagarajan ......... | A61B 5/7217 600/523 |
| 2012/0157798 A1* | 6/2012 | Averina ............. | A61N 1/36542 600/301 |
| 2017/0095214 A1* | 4/2017 | Ramachandran ...... | A61B 5/053 |
| 2017/0361118 A1* | 12/2017 | Liu ........................ | A61B 5/347 |
| 2018/0001100 A1 | 1/2018 | Gehman et al. | |
| 2019/0001144 A1* | 1/2019 | Liu ..................... | A61N 1/3925 |
| 2019/0105504 A1 | 4/2019 | Liu et al. | |

* cited by examiner

FIG. 8D

MIXED-SEGMENT ELECTROCARDIOGRAM ANALYSIS IN COORDINATION WITH CARDIOPULMONARY RESUSCITATION FOR EFFICIENT DEFIBRILLATION ELECTROTHERAPY

CROSS-REFERENCE TO RELATED APPLICATIONS

This application claims priority under 35 U.S.C. § 119 (e) to U.S. Provisional Application Ser. No. 63/119,138, titled "MIXED-SEGMENT ELECTROCARDIOGRAM ANALYSIS IN COORDINATION WITH CARDIOPUL- MONARY RESUSCITATION FOR EFFICIENT DEFI- BRILLATION ELECTROTHERAPY," filed Nov. 30, 2020, which is hereby incorporated herein by reference in its entirety.

BACKGROUND

Medical devices that can assist a healthcare provider in the administration of cardiopulmonary resuscitation (CPR) include automated resuscitation systems and automated defibrillators, among others. Some automated defibrillators intelligently monitor a patient's condition, periodically pro- vide instructions regarding treatment, and even administer treatment to the patient autonomously. Automated defibril- lators include electrodes that can be coupled to the patient's skin to acquire electrical signals generated by a patient's cardiac activity. These electrical signals may be referred to as electrocardiogram (ECG) signals. Automated defibrilla- tors also include circuitry that can analyze the acquired electrocardiogram signals in an attempt to categorize the analyzed signals into one of several predefined cardiac rhythms. These rhythms can include a normal sinus rhythm or arrhythmias such as ventricular fibrillation (VF), ven- tricular tachycardia (VT), atrial fibrillation (AF), tachycar- dia, bradycardia, asystole, and pulseless electrical activity (PEA), to name a few. Exhibition of certain arrhythmias can indicate a life-threatening condition that can be treatable via electrotherapy. For example, a cardiac condition indicated by ventricular fibrillation can be treated by a defibrillating shock to the patient's myocardium. As such, some auto- mated defibrillators include circuitry that can discharge electrotherapy automatically, or under control of a health- care provider. These automated defibrillators include, or have access to, an energy source to power the electrotherapy and electrodes connected to the energy source through which the electrotherapy can be discharged.

To guide a healthcare provider in the administration of CPR, some automated defibrillators include a user interface to output instructions to the healthcare provider. These instructions can include prompts to begin a cycle of CPR, feedback to help pace compressions, prompts to administer rescue breaths, and prompts to pause CPR so that the automated defibrillator can analyze the patient's ECG sig- nals to provide further instructions. These further instruc- tions can include directions to administer subsequent cycles of CPR and/or to administer electrotherapy to the patient.

SUMMARY

In at least one example, an external defibrillator is pro- vided. The external defibrillator includes therapy delivery circuitry configured to discharge electrotherapy to a patient, at least one chest compression sensor configured to acquire motion signals during and after administration of cardiopulmonary resuscitation (CPR) to the patient, at least one electrocardiogram (ECG) sensor configured to acquire ECG signals from the patient, and at least one processor coupled to the therapy delivery circuitry, the at least one chest compression sensor, and the at least one ECG sensor. The at least one processor is configured to generate first ECG data from ECG signals acquired during a cycle of CPR, generate second ECG data from ECG signals acquired after the cycle of CPR, identify a plurality of temporally overlapping segments in the first ECG data, determine shock/no-shock guidance based on the plurality of temporally overlapping segments, confirm the shock/no-shock guidance based on the second ECG data, and control the therapy delivery circuitry to discharge the electrotherapy where the shock/ no-shock guidance is confirmed to specify electrotherapy.

Examples of the external defibrillator can include one or more of the following features.

In the external defibrillator, to determine the shock/no- shock guidance can include to analyze each segment of the plurality of temporally overlapping segments to derive at least one feature from the segment, determine whether the at least one feature meets at least one criterion of a plurality of criteria, each criterion of the plurality of criteria specifying one or more constraints on one or more features of an ECG signal, and increment at least one counter associated with the at least one criterion where the at least one feature meets the at least one criterion. The at least one feature can specify at least one attribute of an ECG waveform specified in the segment. The at least one attribute can be one or more of waveform slope, waveform amplitude, waveform frequency, QRS width, QRS rate, or QRS variation. The plurality of criteria can include at least one criterion associated with 1-second reconfirmation, at least one criterion associated with 2-second reconfirmation, at least one criterion associate with 3-second reconfirmation, and at least one criterion associated with noise. The at least one processor can be further configured to determine whether the noise is reduc- ible via settling time.

In the external defibrillator, at least one segment of the plurality of temporally overlapping segments can span a duration different from a duration of another segment of the plurality of temporally overlapping segments. At least two segments of the plurality of temporally overlapping seg- ments can span an equal duration. At least one segment of the plurality of temporally overlapping segments can include an overlapping portion sharing a period of time with another segment of the plurality of temporally overlapping segments and a new portion distinct from the overlapping portion. One or more segments of the plurality of temporally overlapping segments can span 3 seconds and include an overlapping portion spanning 2.5 seconds. The plurality of temporally overlapping segments can be a first plurality of temporally overlapping segments and to confirm the shock/no-shock guidance can include to identify a second plurality of temporally overlapping segments in the second ECG data, and confirm the shock/no-shock guidance based on the second plurality of temporally overlapping segments in the second ECG data. To confirm the shock/no-shock guidance based on the second plurality of temporally overlapping segments can include to analyze each segment of the second plurality of temporally overlapping segments to derive at least one feature from the segment, determine whether the at least one feature meets at least one criterion specifying one or more constraints on one or more features of an ECG signal, and confirm the shock/no-shock guidance where the at least one feature meets the at least one criterion. The second plurality of temporally overlapping segments can include segments spanning different durations and segments spanning equal durations. The different durations can include 1 second durations and 2 second durations. The shock/no-shock guidance can specify electrotherapy or continued CPR.

In the external defibrillator, the at least one processor can be further configured to determine at least one impedance measurement based on an impedance detection signal acquired after the cycle of CPR and/or determine at least one acceleration measurement based on motion signals acquired after the cycle of CPR, and determine, based on the at least one impedance measurement and/or the at least one acceleration measurement, whether the second ECG data comprises noise sufficient to prevent confirmation. The at least one impedance measurement can include a plurality of impedance measurements, the at least one acceleration measurement can include a plurality of acceleration measurements, and to determine whether the second ECG data comprises noise sufficient to prevent confirmation can include to derive at least one standard deviation measurement for the plurality of impedance measurements and/or the plurality of acceleration measurements, compare the at least one standard deviation measurement to at least one threshold value, and determine that the second ECG data comprises noise sufficient to prevent confirmation where the at least one standard deviation measurement transgresses the at least one threshold value and an amplitude transgresses a threshold value. To determine whether the second ECG data comprises noise sufficient to prevent confirmation can include to determine whether the second ECG data indicates saturation and determine that the second ECG data comprises noise sufficient to prevent confirmation where the second ECG data indicates saturation. The at least one impedance measurement can include a plurality of impedance measurements, the at least one acceleration measurement can include a plurality of acceleration measurements, and to determine whether the second ECG data comprises noise sufficient to prevent confirmation can include to determine that the second ECG data does not indicate saturation, derive at least one standard deviation measurement for the plurality of impedance measurements and/or the plurality of acceleration measurements, compare the at least one standard deviation measurement to at least one threshold value, determine that the at least one standard deviation measurement transgresses the at least one threshold value, determine whether an amplitude specified within the second ECG data transgresses a threshold value, and determine that the second ECG data comprises noise sufficient to prevent confirmation where the at least one standard deviation measurement transgresses the at least one threshold value and the amplitude transgresses the threshold value. The plurality of temporally overlapping segments can be a first plurality of temporally overlapping segments, the second ECG data can include a second plurality of temporally overlapping segments, and to determine whether the second ECG data comprises noise sufficient to prevent confirmation can include to determine whether at least one segment of the plurality of temporally overlapping segments comprises noise sufficient to prevent confirmation.

In at least one example, an external defibrillator is provided. The external defibrillator includes therapy delivery circuitry configured to discharge electrotherapy to a patient, at least one chest compression sensor configured to acquire motion signals during and after administration of cardiopulmonary resuscitation (CPR) to the patient, at least one electrocardiogram (ECG) sensor configured to acquire ECG signals from the patient, and at least one processor coupled to the therapy delivery circuitry, the at least one chest compression sensor, and the at least one ECG sensor. The at least one processor is configured to generate first ECG data from ECG signals acquired during a cycle of CPR, generate second ECG data from ECG signals acquired after the cycle of CPR, determine shock/no-shock guidance based on the first ECG data, identify a plurality of temporally overlapping segments in the second ECG data, confirm the shock/no-shock guidance based on the plurality of temporally overlapping segments in the second ECG data, and control the therapy delivery circuitry to discharge the electrotherapy where the shock/no-shock guidance is confirmed to specify electrotherapy.

Examples of the external defibrillator can include one or more of the following features.

In the external defibrillator, to confirm the shock/no-shock guidance can include to analyze each segment of the plurality of temporally overlapping segments to derive at least one feature from the segment, determine whether the at least one feature meets at least one criterion specifying one or more constraints on one or more features of an ECG signal, and confirm the shock/no-shock guidance where the at least one feature meets the at least one criterion. The at least one feature can specify at least one attribute of an ECG waveform specified in the segment. The at least one attribute can include one or more of waveform slope, waveform amplitude, waveform frequency, QRS width, QRS rate, or QRS variation. The at least one segment of the plurality of temporally overlapping segments can span a duration different from a duration of another segment of the plurality of temporally overlapping segments. The at least two segments of the plurality of temporally overlapping segments can span an equal duration. The at least one segment of the plurality of temporally overlapping segments can include an overlapping portion sharing a period of time with another segment of the plurality of temporally overlapping segments and a new portion distinct from the overlapping portion. The at least one segment of the plurality of temporally overlapping segments can completely overlap another segment of the plurality of temporally overlapping segments. The plurality of temporally overlapping segments can include segments spanning different durations and segments spanning equal durations. The different durations can include 1 second durations and 2 second durations.

In the external defibrillator, the plurality of temporally overlapping segments can be a first plurality of temporally overlapping segments and to determine the shock/no-shock guidance can include to identify a second plurality of temporally overlapping segments in the first ECG data, and determine the shock/no-shock guidance based on the second plurality of temporally overlapping segments in the first ECG data. To determine the shock/no-shock guidance based on the second plurality of temporally overlapping segments can include to analyze each segment of the second plurality of temporally overlapping segments to derive at least one feature from the segment, determine whether the at least one feature meets at least one criterion of a plurality of criteria, each criterion of the plurality of criteria specifying one or more constraints on one or more features of an ECG signal, and increment at least one counter associated with the at least one criterion where the at least one feature meets the at least one criterion. The plurality of criteria can include at least one criterion associated with 1-second reconfirmation, at least one criterion associated with 2-second reconfirmation, at least one criterion associate with 3-second reconfirmation, and at least one criterion associated with noise. The at least one processor can be further configured to determine whether the noise is reducible via settling time. One or more segments of the second plurality of temporally overlapping segments can span 3 seconds and can include an overlapping portion spanning 2.5 seconds. In the external defibrillator, the shock/no-shock guidance can specify electrotherapy or continued CPR.

In the external defibrillator, the at least one processor can be further configured to determine at least one impedance measurement based on an impedance detection signal acquired after the cycle of CPR and/or determine at least one acceleration measurement based on motion signals acquired after the cycle of CPR, and determine, based on the at least one impedance measurement and/or the at least one acceleration measurement, whether the second ECG data comprises noise sufficient to prevent confirmation. To determine whether the second ECG data comprises noise sufficient to prevent confirmation can include to determine whether the second ECG data indicates saturation and determine that the second ECG data comprises noise sufficient to prevent confirmation where the second ECG data indicates saturation. The at least one impedance measurement can include a plurality of impedance measurements, the at least one acceleration measurement can include a plurality of acceleration measurements, and to determine whether the second ECG data comprises noise sufficient to prevent confirmation can include to determine that the second ECG data does not indicate saturation, derive at least one standard deviation measurement for the plurality of impedance measurements and/or the plurality of acceleration measurements, compare the at least one standard deviation measurement to at least one threshold value, determine that the at least one standard deviation measurement transgresses the at least one threshold value, determine whether an amplitude specified within the second ECG data transgresses a threshold value, and determine that the second ECG data comprises noise sufficient to prevent confirmation where the at least one standard deviation measurement transgresses the at least one threshold value and the amplitude transgresses the threshold value. The plurality of temporally overlapping segments can be a first plurality of temporally overlapping segments, the second ECG data can include a second plurality of temporally overlapping segments, and to determine whether the second ECG data comprises noise sufficient to prevent confirmation can include to determine whether at least one segment of the plurality of temporally overlapping segments comprises noise sufficient to prevent confirmation.

In at least one example, an external defibrillator is provided. The external defibrillator includes therapy delivery circuitry configured to discharge electrotherapy to a patient, at least one chest compression sensor configured to acquire motion signals during and after administration of cardiopulmonary resuscitation (CPR) to the patient, at least one electrocardiogram (ECG) sensor configured to acquire ECG signals from the patient, and at least one processor coupled to the therapy delivery circuitry, the at least one chest compression sensor, and the at least one ECG sensor. The at least one processor is configured to generate first ECG data from ECG signals acquired during a cycle of CPR, generate second ECG data from ECG signals acquired after the cycle of CPR, determine shock/no-shock guidance based on the first ECG data, confirm the shock/no-shock guidance based on the second ECG data, to confirm comprising to determine at least one impedance measurement based on an impedance detection signal acquired after the cycle of CPR and/or determine at least one acceleration measurement based on motion signal acquired after the cycle of CPR, and determine, based on the at least one impedance measurement and/or the at least one acceleration measurement, whether the second ECG data comprises noise sufficient to prevent confirmation, and control the therapy delivery circuitry to discharge the electrotherapy where the shock/no-shock guidance is confirmed to specify electrotherapy.

Examples of the external defibrillator can include one or more of the following features.

In the external defibrillator, the at least one impedance measurement can include a plurality of impedance measurements, the at least one acceleration measurement can include a plurality of acceleration measurements, and to determine whether the second ECG data comprises noise sufficient to prevent confirmation can include to derive at least one standard deviation measurement for the plurality of impedance measurements and/or the plurality of acceleration measurements, compare the at least one standard deviation measurement to at least one threshold value, and determine that the second ECG data comprises noise sufficient to prevent confirmation where the at least one standard deviation measurement transgresses the at least one threshold value and the amplitude transgresses the threshold value. The at least one impedance measurement can include a plurality of impedance measurements and/or the at least one acceleration measurement can include a plurality of acceleration measurements and to determine whether the second ECG data comprises noise sufficient to prevent confirmation can include to derive at least one standard deviation measurement for the plurality of impedance measurements and/or the plurality of acceleration measurements, compare the at least one standard deviation measurement to at least one threshold value, determine that the at least one standard deviation measurement transgresses the at least one threshold value, determine whether an amplitude specified within the second ECG data transgresses a threshold value, and determine that the second ECG data comprises noise sufficient to prevent confirmation where the at least one standard deviation measurement transgresses the at least one threshold value and the amplitude transgresses the threshold value. To determine whether the second ECG data comprises noise sufficient to prevent confirmation can include to determine whether the second ECG data indicates saturation and determine that the second ECG data comprises noise sufficient to prevent confirmation where the second ECG data indicates saturation. The at least one impedance measurement can include a plurality of impedance measurements, the at least one acceleration measurement can include a plurality of acceleration measurements, and to determine whether the second ECG data comprises noise sufficient to prevent confirmation can include to determine that the second ECG data does not indicate saturation, derive at least one standard deviation measurement for the plurality of impedance measurements and/or the plurality of acceleration measurements, compare the at least one standard deviation measurement to at least one threshold value, determine that the at least one standard deviation measurement transgresses the at least one threshold value, determine whether an amplitude specified within the second ECG data transgresses a threshold value, and determine that the second ECG data comprises noise sufficient to prevent confirmation where the at least one standard deviation measurement transgresses the at least one threshold value and the amplitude transgresses the threshold value.

In the external defibrillator, to determine whether the second ECG data comprises noise sufficient to prevent confirmation can include to identify a plurality of temporally overlapping segments in the second ECG data, determine a plurality of impedance measurements based on the ECG signals acquired after the cycle of CPR and/or determine a plurality of acceleration measurements based on motion signal acquired after the cycle of CPR, and determine, based on the at least one impedance measurement and/or the at least one acceleration measurement, whether at least one segment of the plurality of temporally overlapping segments comprises noise sufficient to prevent confirmation. The at least one impedance measurement can include a plurality of impedance measurements and/or the at least one acceleration measurement can include a plurality of acceleration measurements, and to determine whether the at least one segment of the plurality of temporally overlapping segments comprises noise sufficient to prevent confirmation can include to derive at least one standard deviation measurement for the plurality of impedance measurements and/or the plurality of acceleration measurements, compare the at least one standard deviation measurement to at least one threshold value, determine that the at least one standard deviation measurement transgresses the at least one threshold value, determine whether an amplitude specified within the at least one segment of the plurality of temporally overlapping segments transgresses a threshold value; and determine that at least one segment of the plurality of temporally overlapping segments comprises noise sufficient to prevent confirmation where the at least one standard deviation measurement transgresses the at least one threshold value and the amplitude transgresses the threshold value. To determine whether at least one segment of the plurality of temporally overlapping segments comprises noise sufficient to prevent confirmation can include to determine whether the at least one segment of the plurality of temporally overlapping segments indicates saturation and determine that the at least one segment of the plurality of temporally overlapping segments comprises noise sufficient to prevent confirmation where the at least one segment of the plurality of temporally overlapping segments indicates saturation. The at least one impedance measurement can include a plurality of impedance measurements, the at least one acceleration measurement can include a plurality of acceleration measurements, and to determine whether the at least one segment comprises noise sufficient to prevent confirmation can include to determine that the at least one segment of the plurality of temporally overlapping segments does not indicate saturation, derive at least one standard deviation measurement for the plurality of impedance measurements and/or the plurality of acceleration measurements, compare the at least one standard deviation measurement to at least one threshold value, determine that the at least one standard deviation measurement transgresses the at least one threshold value, determine whether an amplitude specified within the at least one segment transgresses a threshold value, and determine that the at least one segment of the plurality of temporally overlapping segments comprises noise sufficient to prevent confirmation where the at least one standard deviation measurement transgresses the at least one threshold value and the amplitude transgresses the threshold value.

In the external defibrillator, to determine the shock/no-shock guidance can include to identify a plurality of temporally overlapping segments in the first ECG data and determine the shock/no-shock guidance based on the plurality of temporally overlapping segments in the first ECG data. To determine the shock/no-shock guidance based on the plurality of temporally overlapping segments can include to analyze each segment of the plurality of temporally overlapping segments to derive at least one feature from the segment, determine whether the at least one feature meets at least one criterion of a plurality of criteria, each criterion of the plurality of criteria specifying one or more constraints on one or more features of an ECG signal, and increment at least one counter associated with the at least one criterion where the at least one feature meets the at least one criterion. The plurality of criteria can include at least one criterion associated with 1-second reconfirmation, at least one criterion associated with 2-second reconfirmation, at least one criterion associate with 3-second reconfirmation, and at least one criterion associated with noise. The at least one processor can be further configured to determine whether the noise is reducible via settling time. At least one segment of the plurality of temporally overlapping segments can span a duration different from a duration of another segment of the plurality of temporally overlapping segments. One or more segments of the plurality of temporally overlapping segments can span 3 seconds and include an overlapping portion spanning 2.5 seconds.

In the external defibrillator, to confirm the shock/no-shock guidance can include to identify a plurality of temporally overlapping segments in the second ECG data and confirm the shock/no-shock guidance based on the plurality of temporally overlapping segments in the second ECG data. To confirm the shock/no-shock guidance based on the plurality of temporally overlapping segments can include to analyze each segment of the plurality of temporally overlapping segments to derive at least one feature from the segment, determine whether the at least one feature meets at least one criterion specifying one or more constraints on one or more features of an ECG signal, and confirm the shock/no-shock guidance where the at least one feature meets the at least one criterion. The plurality of temporally overlapping segments can include segments spanning different durations and segments spanning equal durations. The different durations can include 1 second durations and 2 second durations. The shock/no-shock guidance can specify electrotherapy or continued CPR.

Still other aspects, examples, and advantages of these aspects and examples, are discussed in detail below. Moreover, it is to be understood that both the foregoing information and the following detailed description are merely illustrative examples of various aspects and features and are intended to provide an overview or framework for understanding the nature and character of the claimed aspects and examples. Any example or feature disclosed herein can be combined with any other example or feature. References to different examples are not necessarily mutually exclusive and are intended to indicate that a particular feature, structure, or characteristic described in connection with the example can be included in at least one example. Thus, terms like "other" and "another" when referring to the examples described herein are not intended to communicate any sort of exclusivity or grouping of features but rather are included to promote readability.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral.

For purposes of clarity, not every component may be labeled in every figure. A quantity of each component in a particular figure is an example only and other quantities of each, or any, component could be used.

FIG. 8D is a graphical diagram illustrating another ECG waveform in relation to CPR treatments in accordance with at least one example disclosed herein.

DETAILED DESCRIPTION

Figure 1:
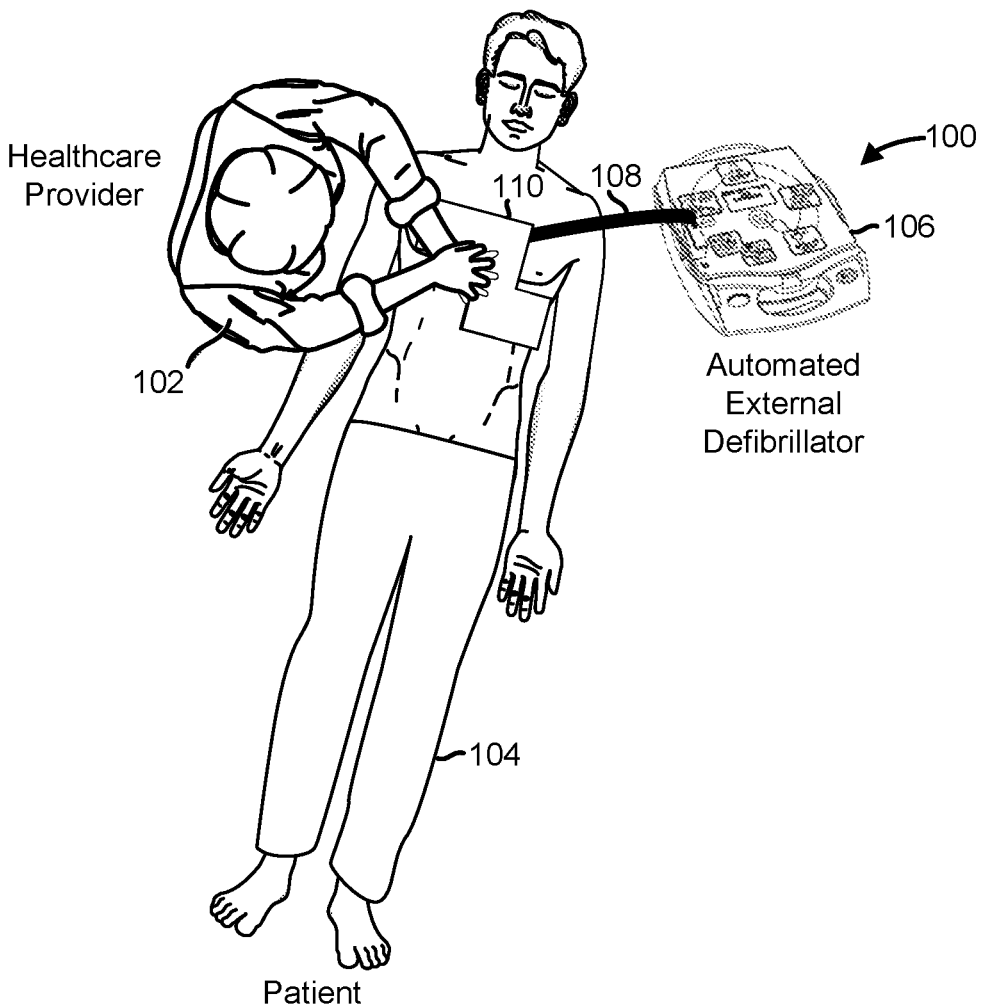
FIG. 1 is a context diagram illustrating a medical device treating a patient in accordance with at least one example disclosed herein.

As summarized above, certain examples described herein are directed to medical devices (e.g., automated external defibrillators) that are equipped to analyze ECG signals of a cardiac arrest patient and make a determination in as short a time as possible as to whether the patient's heart condition is indicative of a shockable or non-shockable rhythm. The medical device then provides an immediate indication of this determination, so that appropriate and timely treatment can be provided. In examples described herein, external defibrillator systems employ decision rules that enable a shockable or non-shockable decision to be made within time frames that are unprecedented (e.g., less than 3 seconds, less than 2 seconds, less than 1 second), so that CPR or other treatments may be administered as soon as possible. That is, time taken to assess whether the patient's heart is in a shockable or non-shockable condition is time taken away from CPR or other life-saving treatments. In certain examples, medical devices provided herein are further able to guide administration of CPR to a patient. As discussed, the aim of CPR is to maintain the patient's circulatory and respiratory systems during cardiac arrest in an attempt to save the life of the patient. The sooner consistent, continuous, and proper administration of CPR begins, the better the patient's chances of survival.

However, the circumstances under which CPR is performed and the physical activity involved with proper performance of CPR present practical obstacles to medical devices configured to guide its administration. For example, consider an illustrative scenario where a patient suffers from sudden cardiac arrest while in a public location. In this scenario, the patient's collapse may be witnessed by a bystander who wishes to help the patient. Depending on the circumstances, the bystander may or may not be able to locate and utilize an automated external defibrillator (AED) to treat the patient. Where the bystander is able to locate an AED, the bystander's inexperience and the gravity of the situation may lead to improper fitting of the AED to the patient and/or improper administration of CPR to the patient. For instance, the bystander may misposition a therapy pad of the AED, and the sensors included therein, on the patient's body. Such incorrect coupling of sensors to the patient can result in acquisition of sensor signals that are contaminated with noise, which complicates accurate analysis of the sensor signals. Alternatively or additionally, the bystander may deliver chest compressions and/or rescue breaths using improper technique and/or at improper times. These actions, too, can complicate accurate analysis of sensor signals. Moreover, the bystander may move the patient during CPR administration and/or cease CPR administration unexpectedly due to fatigue or other unforeseen environmental factors. As with the other activities described above, moving the patient and/or unexpected cessation of CPR can introduce noise and/or otherwise make analysis of sensor signals and provision of shock/no-shock guidance difficult. Furthermore, even where the AED is properly fitted to the patient and CPR is properly administered, the noise generated by CPR compressions can contaminate sensor signals, complicating accurate analysis of the sensor signals and obscuring the patient's ECG signal in unforeseen ways.

The scenario articulated above illustrates only a few of the practical obstacles encountered by health care providers and the medical devices they use to administer CPR. However, the applicants have discovered that, within the context of this unpredictable environment, analysis of multiple segments of sensor data at specific times and in specific combinations can help a medical device to overcome many of these practical obstacles. Using these techniques, the example medical devices described herein accurately analyze sensor signals and guide a healthcare provider through the administration of CPR despite the chaotic environment in which CPR is often administered.

For instance, in some examples, a medical device (e.g., a defibrillator) includes sensors and circuitry configured to monitor signals acquired by the sensors for indications of administration of CPR. The sensors can include motion sensors and/or ECG sensors. The indications of CPR administration can include motion signals that follow a specific, predefined waveform (e.g., signals indicative of chest compressions) and/or motion signals that are detected within an expected time window (e.g., following specific prompts issued by the medical device). By monitoring the sensor signals, the medical device can identify initiation of a cycle of CPR. Such a cycle of CPR includes provision of chest compressions (e.g., 30 compressions) and rescue breaths (e.g., 2 breaths) prior to a pause in CPR.

In certain examples, the medical device also includes sensors and circuitry configured to detect impedance of a circuit including the medical device and the patient's body. In these examples, the medical device can, for example, include an electrode configured to inject an electrical impedance detection signal into the patient's body and another electrode configured to acquire the impedance detection signal from the patient's body. The injected electrical impedance signal can have a known frequency, voltage, and current. Further, in these examples, the medical device is configured to monitor the acquired impedance detection signal to determine its voltage drop and use the same to calculate impedance and changes in impedance over time. Impedance can be one indication of the quality of the electrical connection between the medical device and the patient's body.

In some examples, the medical device continuously generates sensor data (e.g., ECG data, motion data, and impedance data) based on, and representative of, the sensor signals acquired before, during, and after administration of each cycle of CPR. To minimize any pause in CPR, the medical device implements a mixed-segment analysis process that identifies and analyzes various combinations of segments of sensor data. These combinations of segments include, in at least some examples, a plurality of temporally overlapping segments of sensor data generated from signals acquired while CPR is being administered (e.g., during active delivery of chest compressions and/or rescue breaths to the patient). Next, the mixed-segment analysis process attempts to determine shock/no-shock guidance based on the temporally overlapping segments. Use of temporally overlapping segments helps decrease the adverse impact of noise on shock/no-shock guidance accuracy. This feature of overlapping segments is particularly helpful within the context of CPR administration, at least in part due to the noise generated by CPR activities.

In some examples, the combinations of segments identified and analyzed during execution of the mixed-segment analysis processes described herein can also include one or more additional segments acquired during a pause in CPR. These additional segments will generally include less noise artifact due to the absence of CPR activity during their acquisition. Therefore, some example medical devices rely upon one or more of these additional segments to confirm previously established preliminary shock/no-shock guidance determined via analysis of the overlapping segments described above. This confirmation process may be referred to herein as "reconfirmation." The additional segments used by some medical devices within reconfirmation have durations ranging between 1 and 3 seconds.

In some examples, the mixed-segment analysis processes executed by medical devices further identify temporally overlapping segments of sensor data generated from signals acquired during a pause in CPR. By leveraging temporally overlapping segments within this reconfirmation period, the examples described herein extract more information from a given duration of sensor data than do other analysis techniques. This feature enables some example medical devices to complete reconfirmation and provide accurate shock/no-shock guidance more swiftly than other analysis techniques. During the reconfirmation period, CPR chest compressions are paused, and therefore no blood or oxygen is delivered to the heart, brain, and other vital organs. It has been shown that pauses in compressions with durations as short as 1-3 seconds immediately prior to a defibrillation shock will adversely impact the success rates of the defibrillation shocks, and thereby also causing a decrease in overall survival of a cardiac arrest victim. Mixed-segment analysis processes described herein can reduce the pause period by as much as 10-15 seconds, thus significantly improving the chance of a successful defibrillation shock for those cases.

In certain examples, to determine accurate shock/no-shock guidance, the mixed-segment analysis processes described herein attempt to detect any of several predefined cardiac rhythms as being present in the segments of ECG data. In these examples, each of the predefined cardiac rhythms is associated with particular shock/no-shock guidance. For instance, where the medical device determines that one or more segments of ECG data present VF, the medical device can issue shock/no-shock guidance to administer electrotherapy to the patient because VF is a shockable rhythm. In some examples, to detect predefined cardiac rhythms present in segments of ECG data, the medical device compares features derived from the segments of ECG data to one or more sets of constraints on these features. These sets of constraints (referred to herein as "clauses") specify values of features known to be indicators of the predefined cardiac rhythms. What clauses are and how examples utilize them is described further below, but it should be noted that clauses can be used to analyze overlapping segments of varying durations to reach varying levels of certainty regarding the presentation of particular cardiac rhythms. By analyzing temporally overlapping segments of various durations (i.e., shorter durations, where possible), the mixed-segment analysis processes described herein resourcefully utilize the information at hand to reach accurate shock/no-shock guidance as quickly as possible.

In certain examples, to identify temporally overlapping segments, the medical device selects segments with at least some attributes that are based upon the clauses used to determine shock/no-shock guidance. For instance, in some examples, the medical device selects temporally overlapping segments having durations that are equal to durations associated with the clauses. These durations can be, for example, 1 second, 2 seconds, 3 seconds, or 6 seconds, although the medical device can identify segments and utilize clauses with other durations in some examples.

In at least some examples, each clause has a duration of presentation required to reach a threshold accuracy (e.g., 99%) in determining a patient's condition. Accuracy of a clause is based on levels of sensitivity, specificity, positive predictive value, and/or negative predictive value of the clause as an indicator of the patient's true condition. For instance, in one example, the accuracy of a clause is simply the positive predictive value of the clause when present within a patient's ECG signal. Generally, in these examples, the duration of a clause is directly related to the accuracy associated with the clause (e.g., longer duration clauses generally have higher accuracy than shorter clauses), although this is not necessarily true in all cases. For instance, an accuracy of a first clause having a duration of 1 second may be sufficient to give weight to a segment of ECG data exhibiting the clause in determining shock/no-shock guidance, while an accuracy of a second clause having a duration of 2 seconds may be sufficient to give additional (e.g. definitive) weight to a segment exhibiting the second clause in determining the shock/no-shock guidance. In this case, the medical device may identify temporally overlapping segments with durations of 1 second and/or 2 seconds so that the segments can be evaluated vis-à-vis both the first clause and the second clause.

In some examples, in determining the shock/no-shock guidance based on the previously identified temporally overlapping segments, the medical device first filters out any segment of the temporally overlapping segments that is contaminated with excessive noise. The filtering techniques implemented by the medical device can vary between examples. For instance, in some examples, the medical device executes a filtering operation by detecting sensor saturation within a segment, motion data values in excess of a threshold within the segment, ECG data (amplitude) values in excess of a threshold within the segment, and/or impedance variability values in excess of a threshold within the segment. This type of filtering can be particularly useful for sensor data acquired during a pause in CPR, as artifacts present in sensor data during this reconfirmation period tend to indicate improper placement and/or improper use of the medical device rather than the performance of CPR activities, which have ceased. At least one process for determining whether a segment is contaminated with excessive noise is described below with reference to FIG. 7. Next, the medical device attempts to detect a predefined cardiac rhythm within the segment, as described above, to determine the shock/no-shock guidance (e.g., shock/no-shock guidance associated with the cardiac rhythm). For instance, the medical device can attempt to detect a predefined cardiac rhythm within the segment by determining whether each segment satisfies a clause associated with the cardiac rhythm and the shock/no-shock guidance. This shock/no-shock guidance may be, for example, to administer another CPR cycle where the patient's condition is not treatable via electrotherapy or to administer the electrotherapy where the patient condition is treatable via the electrotherapy.

In certain examples, the medical device continues to acquire and process sensor signals to generate additional, temporally overlapping segments and to determine shock/no-shock guidance based on the temporally overlapping segments until the medical device detects a pause in CPR. In these examples, upon detecting a pause in CPR, the medical device attempts to confirm the shock/no-shock guidance determined during the previously active CPR cycle. For instance, in some examples, the medical device continues to acquire and process sensor signals during the pause in CPR to generate new segments and to confirm the shock/no-shock guidance based on the new segments. These new segments can include multiple, temporally overlapping segments with durations based on clauses to which the new segments will be compared. In some examples, the medical device attempts to confirm the shock/no-shock guidance by determining whether the new segments indicate the same patient condition (and thus shock/no-shock guidance) as the segments analyzed during active CPR. Where the medical device determines that the new segments indicate the same patient condition and/or shock/no-shock guidance (e.g., whether the cardiac rhythm is shockable or non-shockable), the medical device confirms the shock/no-shock guidance of whether defibrillation is recommended. In these examples, the medical device can determine whether the new segments indicate the same patient condition by filtering out any segments from the new segments that are contaminated with excessive noise and attempting to detect the presence of predefined cardiac rhythms as described above.

In certain examples, the medical device communicates and/or executes confirmed shock/no-shock guidance. For instance, in some examples where the confirmed shock/no-shock guidance is to administer electrotherapy to the patient, the medical device announces the same, requests that the healthcare provider disengage and remain clear of the patient, and controls electrotherapy delivery components of the medical device to discharge the electrotherapy to the patient. Actual control of electrotherapy delivery may be automatic in which the medical device delivers the electrotherapy (e.g., defibrillation shock) without user intervention, or electrotherapy delivery may be semi-automatic in which the medical device provides an indication that electrotherapy (e.g., defibrillation shock) should be delivered, yet requires a user to actuate an input (e.g., shock button) to actually deliver the electrotherapy. This electrotherapy can be transcutaneous where the medical device is an external defibrillator, such as an AED. Where the confirmed guidance is to continue CPR, the medical device announces the same and requests that the healthcare provider administer another cycle of CPR. Alternatively or additionally, where the medical device includes an automated chest compression system, the medical device controls chest compression components of the medical device to administer compressions to the patient.

In some examples, where the medical device cannot confirm the previously established shock/no-shock guidance, the medical device continues to monitor the patient in an attempt to determine new shock/no-shock guidance. In these examples, the medical device continues to acquire and process sensor signals during the pause in CPR to generate new segments. These new segments can include multiple, temporally overlapping segments with durations based on clauses to which the new segments will be compared. In some examples, the medical device filters out any segments from the new segments that are contaminated with excessive noise and compares the new segments to the clauses. Where the medical device determines that the new segments satisfy a clause, the medical device can determine the new shock/no-shock guidance to be shock/no-shock guidance associated with the clause. Next, the medical device communicates and/or executes the new shock/no-shock guidance as it would have communicated and/or executed the confirmed shock/no-shock guidance as described above. Where the medical device cannot establish new shock/no-shock guidance within a predetermined time window, the medical device can take another action, such as communicate, recommend, instruct, and/or execute a new cycle of CPR.

The techniques and apparatus disclosed herein for guiding administration of CPR to a patient can be implemented via a variety of medical devices. These medical devices may include, for example, external defibrillators/monitors, AEDs, wearable defibrillators, and automated resuscitation systems. Examples of external defibrillators/monitors include the R SERIES® or X SERIES® defibrillators commercially available from ZOLL Medical Corporation of Chelmsford, Massachusetts. External defibrillators/monitors are commonly found in hospitals and used by emergency medical services. Examples of AEDs include the AED PLUS® automated external defibrillator or the AED PRO® automated external defibrillator commercially available from ZOLL Medical Corporation. AEDs are frequently seen in airports, public gymnasiums, schools, shopping areas and other public spaces. Examples of wearable defibrillators include the ZOLL® LIFEVEST® wearable cardioverter defibrillator commercially available from ZOLL Medical Corporation. Examples of automated resuscitation systems include the AutoPulse® chest compression device commercially available from the ZOLL Medical Corporation.

Turning now to FIG. 1, an AED 100 is illustrated within the context of patient treatment. The AED 100 is coupled to a patient 104, who is being cared for by a healthcare provider 102. As shown in FIG. 1, the AED 100 includes a control unit 106, a therapy pad 110, and a connector 108. The control unit 106 includes a processor, memory, a user interface, device interfaces, and/or a battery or other power source. The memory can persistently store instructions executable by the processor to perform various functions described herein as being performed by the AED 100 (or more generally by a medical device). The functions can include, for example, monitoring of a patient's ECG signals among many others described below. The therapy pad 110 includes ECG sensors (e.g., sensing electrodes) to acquire the patient's ECG signals and electrotherapy delivery components (e.g., electrotherapy electrodes) to discharge transcutaneous electrotherapy to the patient's myocardium. The therapy pad 110 can also include additional sensors, such as a motion sensor (e.g., an accelerometer). To detect impedance, the AED 100 can utilize the ECG sensors to detect an impedance signal injected by the electrotherapy delivery components or may include separate, dedicated components for this purpose. The connector 108 can include wiring suitable to convey the patient's ECG signals, motion signals, and impedance signals from the sensors to the control unit 106 and/or to convey the electrotherapy from the control unit 106 to the electrotherapy delivery components. Further details regarding the AED 100, and medical devices more generally, are articulated below with reference to FIGS. 10 and 11.

As shown in FIG. 1, the healthcare provider 102 is treating the patient 104 using the AED 100. To treat the patient 104, the healthcare provider 102 may administer one or more cycles of CPR, with each cycle including a series of chest compressions and one or more rescue breaths. Before, during, between, and after administering each CPR cycle, the healthcare provider 102 may consult and/or consider guidance presented to the healthcare provider 102 by the AED 100. This guidance can include instructions rendered in any human perceptible medium, such as audio and/or visual output via the user interface. In some implementations and/or situations, the AED 100 instructs the healthcare provider 102 to pause between CPR cycles, so that the AED 100 can analyze sensor signals (including ECG signals of the patient) and present additional guidance based on the results of the analysis.

Figure 2:
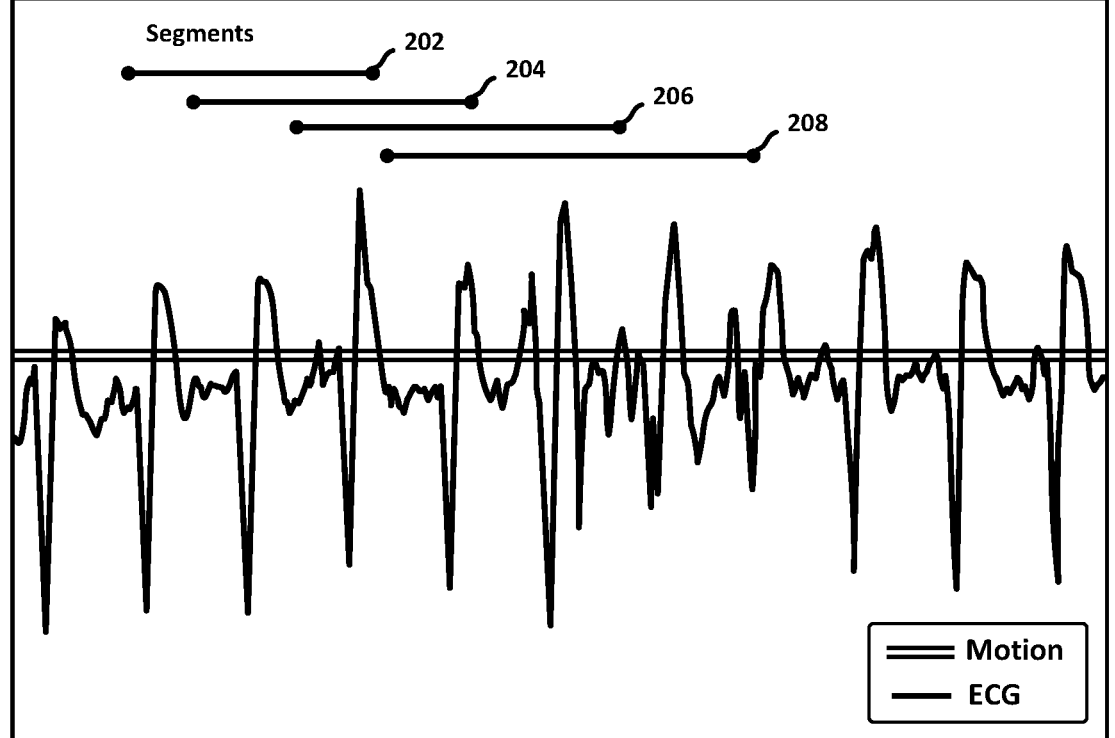
FIG. 2 is a graphical diagram illustrating analysis, by a medical device, of multiple overlapping segments of sensor data as part of a mixed-segment analysis process in accordance with at least one example disclosed herein.

As explained above, it is important to minimize pauses in CPR, as even a few seconds of CPR inactivity can mean the difference between life and death in some patient encounters. As such, some examples disclosed herein implement processes that provide precise and accurate guidance of whether the patient's ECG is indicative of a shockable or non-shockable condition as quickly as possible, and thereby help minimize pauses in CPR. In these examples, medical devices such as the AED 100 are configured to identify one or more segments of sensor data and to analyze these one or more segments to determine guidance to render to a healthcare provider. FIG. 2 illustrates an example in which a medical device is configured to identify and analyze multiple, temporally overlapping segments 202-208.

As shown in FIG. 2, each of the segments 202-208 includes data digitized from a series of consecutive signal samples acquired by sensors of the medical device and stored in a memory of the medical device. In some examples illustrated by FIG. 2, each of the segments 202-208 includes 750 samples. Each of the samples is associated with a 4 millisecond time period during which the sample was acquired. Thus, in these examples, each of the segments 202-208 represents an overall time period of 3 seconds. However, as provided herein, such segments of sensor data can have multiple time durations (e.g., 1 second, 2 seconds 3 seconds, 4 seconds, 5 seconds, or longer). As shown in FIG. 2, for some examples, each of the segments 202-208 may include sensor data derived from multiple types of sensors. This sensor data includes ECG data based on ECG signals acquired by one or more sensing electrodes, motion data based on motion signals acquired by one or more accelerometers, and impedance data based on an impedance detection signal acquired by the one or more sensing electrodes. The ECG data may be analyzed to determine the nature of the current cardiac rhythm of the patient; and the motion and/or impedance data may be analyzed to determine the reliability of the ECG data based on how much noise is present in the system.

However, it should be noted that segments, such as the segments 202-208, can have the same, or different, durations and that segments can include data derived from a single type of sensor or multiple types of sensors. For example, the number of samples within each of the segments 202-208 can vary based on the type, model, and/or configuration of the sensors that acquire the samples. For instance, a sensor of a first type (e.g., a sensing electrode) can have a sampling rate that is different from a sensor of a second type (e.g., an accelerometer). Similarly, a first model of accelerometer can have a sampling rate that is different from a second model of accelerometer and some models of accelerometers can be configured to sample at different rates. As such, each of segments 202-208 can span durations as short as 100 milliseconds to as long as 15 seconds. These differences in sampling rates can result in segments with the same duration having varying numbers of samples.

Continuing with the example of FIG. 2, each of the segments 202-208 includes ECG data, motion data, and impedance data. Each of the ECG data, the motion data, and the impedance data can be represented as a distinct waveform with features and/or feature combinations that specify information about the patient's condition, the medical device, and activity involving the patient and/or the medical device. In the case of the ECG data, certain components of interest of the waveform include the patient's distinct cardiac morphology. Some of the features of the waveform representations of the ECG, motion, and impedance data include, for example, maximum slope, relative flatness, amplitude variability, average amplitude, maximum amplitude, minimum amplitude, number of peaks, average peak width, peak width variability, peak top amplitude variability, peak top interval variability, width variability, and slope zero crossings among other features. Features specific to ECG waveforms can include, for example, QRS rate, QRS width variability, maximum QRS width, and number of supraventricular tachycardia (SVT) beats. It should be noted that the waveforms specified by the sensor data of the segments 202-208 can have other features salient to the example guidance processes disclosed herein.

Some features and/or combinations of features can indicate whether excessive noise is present within one or more of the segments 202-208. For instance, segments of ECG data with values that reach a limit of the dynamic range of the ECG sensor indicate the presence of excessive noise. Additionally, samples of ECG data with values that exceed a threshold value that coincide with samples of motion data and/or impedance data that presents variability that exceeds corresponding threshold values can indicate excessive noise. One example of a process that a medical device, such as the AED 100, can execute to detect such noise is described further below with reference to FIG. 7.

Some features and/or combinations of features can indicate whether one or more of the segments 202-208 present one or more of the predefined cardiac rhythms described herein. For instance, ECG data within one or more of the segments 202-208 may have features that satisfy one or more predefined sets of constraints (clauses) that indicate the presence of one or more of the cardiac rhythms. Satisfaction of the constraints of a clause by features of a segment indicates, to a degree of accuracy associated with the clause, whether electrotherapeutic treatment of an arrhythmia underlying the segment is advisable or not advisable. Arrhythmias for which electrotherapeutic defibrillation treatment is advisable may be referred to as shockable rhythms. Arrhythmias for which electrotherapeutic defibrillation treatment is not advisable may be referred to as non-shockable rhythms. Examples of processes that a medical device, such as the AED 100, can execute to determine shock/no-shock guidance are described further below with reference to FIGS. 5-6G.

In some examples, but not all instances, the degree of accuracy associated with some clauses varies directly with a duration of time that the clauses are satisfied. For instance, in some examples, a particular clause is a high accuracy clause where the clause is satisfied by an ECG data segment for a threshold duration (e.g., a duration associated with the particular clause). Further, the same clause may be a normal accuracy clause where the clause is satisfied by an ECG data segment for less than the threshold duration. Thus, for these clauses, there will be minimum ECG data segments with durations below which the clauses are only normal accuracy clauses, and are not suitable as high accuracy clauses, but for ECG data segments with durations longer than this minimum duration, the clauses can be high accuracy clauses.

For instance, there may be clauses for which the minimum duration is 1 second, which are termed "1-second clauses." For instance, there may be clauses for which the minimum duration is 2 seconds, which are termed "2-second clauses." For instance, there may be clauses for which the minimum duration is 3 seconds, which are termed "3-second clauses." Segments for which the minimum duration is 6 seconds are termed "6-second clauses." Some examples of these are listed in TABLE 1.

TABLE 1

| Clause Timing | Intended Waveforms | Clause | Shock/ No-Shock Guidance |
|---|---|---|---|
| 1-second | Normal sinus rhythm (one clear peak) | Maximum Slope >200 µV/sample and Relative Flatness >100 | No Shock |
| 1-second | Asystole (low max and min amplitudes) | Maximum Amplitude <50 µV and Minimum Amplitude <−50 µV | No Shock |
| 1-second | Slow VT | Peaks <3 and Average Peak Width >160 ms | No Shock |
| 1-second | PEA | Maximum Slope <30 µV/sample and Peaks <3 | No Shock |

TABLE 1-continued

| Clause Timing | Intended Waveforms | Clause | Shock/ No-Shock Guidance |
|---|---|---|---|
| 1-second | VFIB | Peaks >3 and Relative Flatness <50 | Shock |
| 1-second | Fast VT | Peaks >= 4, Average Peak Width >160 ms, and Peak Width Variability <100 | Shock |
| 2-second | AFIB (many peaks but one or more tall peaks) | Maximum Slope >200 µV/sample, Relative Flatness >80, and Peak Amplitude Variability <250 | No Shock |
| 2-second | Slow PEA | Maximum Slope <50 µV/sample, Peak Amplitude Variability <250, and Peak Interval Variability <100 | No Shock |
| 2-second | VF (many peaks) | Maximum Slope >50 µV/sample, Relative Flatness <50, and Slope Zero Crossings >20 | Shock |
| 2-second | VT (high rate) | R-R Interval <350 ms, QRS Width >140 ms, and QRS Width Variability = Stable | Shock |
| 3-second | Few sharp peaks | Amplitude Variability <Threshold, Maximum Amplitude >250 µV, and Maximum Slope >Threshold | No Shock |
| 3-second | Stable HR and QRS width | (QRS Rate >220, QRS Width Variability = Stable, QRS Width <100 ms) or (SVT = detected and QRS Rate >245) | No Shock |
| 3-second | Stable QRS width | QRS Width Variability = Stable, QRS Width <65 ms, Maximum Amplitude >250 µV, and QRS Rate >300 | No Shock |
| 3-second | Stable QRS amplitude, large QRS amplitude, clear peaks, HR >180 | Amplitude Variability <Threshold, Maximum Amplitude >500 µV, QRS Variability <Threshold, and QRS Rate >300 | No Shock |
| 6-second | VT waveform (HR > 150 bpm and wide complexes) | R-R Interval <400 ms, QRS Width >140 ms, QRS Width Variability = 1, and Relative Flatness >50 | Shock |
| 6-second | Irregular PEA rhythm (intermittent flat areas and wide peaks) | Relative Flatness >200 and Peak Width >300 | No Shock |
| 6-second | Asystole waveform with very small electrical activity | Average Amplitude >100 µV | No Shock |
| 6-second | Fast PEA type waveform where HR >160 with some variability and stable QRS width but maximum slope is low | QRS Rate >270 bpm, QRS Variability <Threshold, Maximum Slope <Threshold, and QRS Width Variability <Threshold | No Shock |
| 6-second | SVT type waveform, number of SVT beats exceeds threshold, HR <185 | SVT = detected or (SVT Beats >Threshold, QRS Rate >Threshold, and QRS Width <140 ms) | No Shock |

In certain examples, the relative flatness referred to herein can be calculated as a difference between the greatest slope and/or amplitude of ECG data within a segment and the average slope or amplitude. Measures of variability referred to in TABLE 1 include, for example, standard deviations of the subject metric. QRS widths are considered stable where the standard deviation of the QRS widths falls within a range of, for example, 7 to 20 ms. The slope and variability thresholds referred to in TABLE 1 are dynamically set based on the characteristics of the segment being analyzed and/or neighboring/overlapping segments.

In some examples, any of the segments 202-208 that satisfies a high accuracy clause is definitive regarding the shock/no-shock guidance associated with the segments 202-208. As such, where one of the segments 202-208 satisfies a high accuracy clause, the shock/no-shock guidance associated with the high accuracy clause is recorded as the shock/no-shock guidance for the segments 202-208. Alternatively or additionally, in some examples, any of the segments 202-208 that satisfies a normal accuracy clause is counted as a vote for the shock/no-shock guidance associated with the normal accuracy clause. Each of these votes can be counted, for example, by incrementing a counter variable stored in memory and associated with the shock/no-shock guidance. Further, in these examples, the shock/no-shock guidance recorded for the segments 202-208 is the shock/no-shock guidance associated with the segments in the voting majority.

Turning to FIGS. 3A-3H, an example is illustrated in which a medical device (e.g., the AED 100 of FIG. 1) analyzes a mixed set of segments in multiple phases, with each phase of the analysis corresponding to one or more of the FIGS. 3A-3H. By structuring its analysis as shown in FIGS. 3A-3H, the medical device in this example positions itself to render reliable shock/no-shock guidance more quickly than medical devices that execute other guidance processes.

Figure 3A:
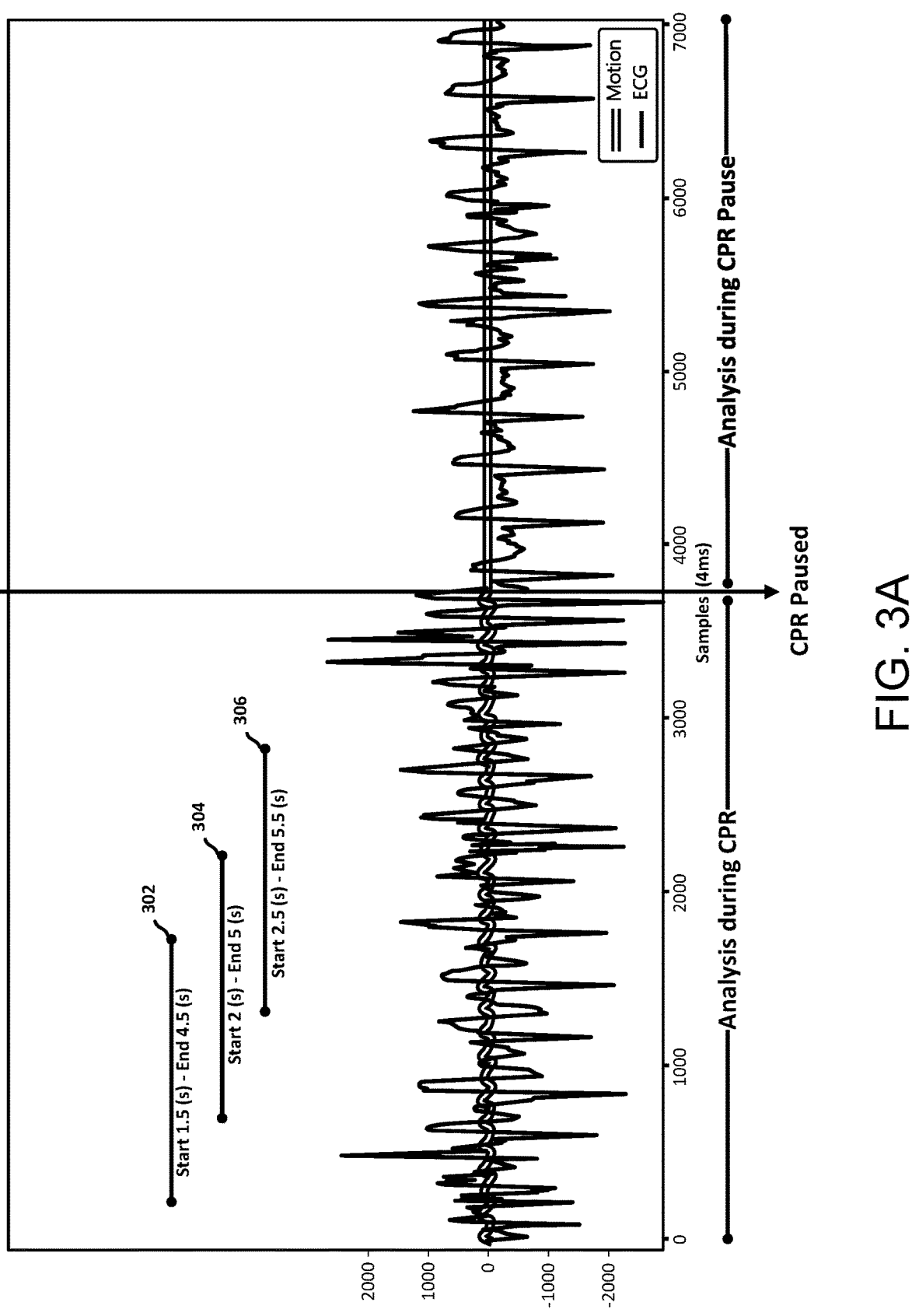
FIG. 3A is a graphical diagram illustrating analysis, by a medical device, of multiple overlapping segments of sensor data generated from signals acquired during administration of CPR as part of a mixed-segment analysis process in accordance with at least one example disclosed herein.

FIG. 3A illustrates a phase in which the medical device identifies and analyzes multiple, temporally overlapping segments 302-306 generated from signals acquired during administration of CPR. Any of the segments 302-306 can have the attributes of any of the segments 202-208 described above. As shown in FIG. 3A, each of the segments 302-306 spans 3 seconds and each of the segments 304 and 306 is offset 0.5 seconds from the previous segment. As shown in FIG. 3A, the segment 302 begins 1.5 seconds after initiation of a cycle of CPR, the segment 304 begins 2 seconds after initiation of the cycle of CPR, and the segment 306 begins 2.5 seconds after initiation of the cycle of CPR. For various embodiments, segment start times and durations other than those depicted and described may be appropriate. Additionally, in some examples, the offset times listed above may be less than 0.5 seconds (e.g., 0.1 seconds, 0.2 seconds, etc.) to increase scrutiny of, and information gleaned, from sensor data acquired during administration of CPR. Alternatively, in some examples, the offset times listed above may be greater than 0.5 (e.g., 0.6 seconds, 0.7 seconds, etc.) to decrease the computational load placed on the medical device.

In the example of FIG. 3A, because each of the segments 302-306 includes data generated from signals acquired during a cycle of CPR, each of the segments 302-306 is expected to have some level of noise generated by chest compressions, rescue breaths, and other motion that sometimes occurs during administration of a cycle of CPR. As such, none of the segments 302-306 can definitively determine shock/no-shock guidance. Rather, in this example, the medical device records (e.g., by incrementing a counter), for each of the segments 302-306, a vote toward determination of a process for confirming, during a future pause in CPR, the shock/no-shock guidance of the majority of the segments 302-306. This process of confirming shock/no-shock guidance may be referred to as a "reconfirmation" phase. In certain examples, these reconfirmation phases can include 1-second reconfirmation, 2-second reconfirmation, and 3-second reconfirmation. Reconfirmation is helpful, if not required, for more definitive determination of shock/no-shock guidance because in reconfirmation phases the medical device analyzes segments of data generated from signals acquired during a pause in physical CPR activities. These signals tend to be higher quality than signals acquired during administration of a CPR cycle as at least some of the sources of noise present during administration of a CPR cycle are absent during a pause in CPR. Accordingly, in reconfirmation, the ECG analysis during the CPR pause is able to confirm the previous analysis and tentative treatment determination that had been made during the CPR period. Although FIG. 3A illustrates 3 segments, the examples described herein are not limited to a particular number of segments or time spanned thereby. For instance, in some examples, the medical device identifies 15 segments of sensor data generated from signals acquired during 12 seconds of active CPR.

In some examples, the medical device can analyze the segments 302-306 to determine whether reconfirmation is appropriate and, as such, made available. In these examples, the medical device can make this determination using a voting scheme. Under a voting scheme, each reconfirmation phase is associated, within a memory of the medical device, with a set of criteria that a segment must meet for the segment to contribute (e.g., by incrementing a counter) a vote toward electing the reconfirmation phase. Further, under a voting scheme, the medical device can determine whether each of the segments 302-306 meets any of the sets of criteria associated with the reconfirmation phases. Where one of the segments 302-306 meets a set of criteria, the medical device can record a vote for the reconfirmation phase associated with the set of criteria. Additionally, in some examples, the medical device can record a vote for no reconfirmation for each of the segments 302-306 that is contaminated with excessive noise or can record a vote for provision of settling time for each of the segments 302-306 that exhibits noise likely to be absent during a pause in CPR (e.g., low frequency noise generated by CPR activities). Thus, in these examples, each of the segments 302-306 can cause the medical device to record a vote for either 1-second reconfirmation, 2-second reconfirmation, 3-second reconfirmation, provision of settling time, or no reconfirmation due to noise. The set of criteria associated with each reconfirmation phase can vary, but in at least some examples, the set of criteria includes satisfaction, by features of the segment, of at least one clause associated with a particular reconfirmation phase or type of noise. Thus, in some examples, determining whether a segment meets a set of criteria associated with a reconfirmation phase includes determining whether the segment meets a clause specified by the set of criteria associated with the reconfirmation phase. It should be noted that, in some situations, a segment can meet clauses for multiple confirmation phases (1-second reconfirmation, 2-second reconfirmation, and/or 3-second reconfirmation). In these situations, the medical device records a vote for the shortest duration reconfirmation phase associated with a clause met by the segment.

How the medical device uses the voting results can vary between examples. In some examples, the medical device avoids unnecessary computing time and overhead by, for example, proceeding directly to specific phases based on the votes. For instance, where a threshold number of the segments 302-306 are contaminated with excessive noise, the medical device can avoid reconfirmation altogether. Additionally or alternatively, where a threshold number of segments cause the medical device to vote for allocation of settling time, the medical device can proceed directly to 3-second reconfirmation as illustrated and described below with reference to FIG. 3F. However, in other examples, the medical device can proceed through at least a portion of each reconfirmation phase so as to leverage, as quickly as possible, the information gleaned from the segments 302-306 in combination with newly generated segments based on "clean" (without CPR artifacts) sensor signals. For instance, in these examples, the medical device can always attempt to confirm shock/no-shock guidance via 1-second reconfirmation and move to longer reconfirmation phases if necessary. Examples illustrating these principles of flow control are described in detail below with reference to FIGS. 5-6F.

Figure 3B:
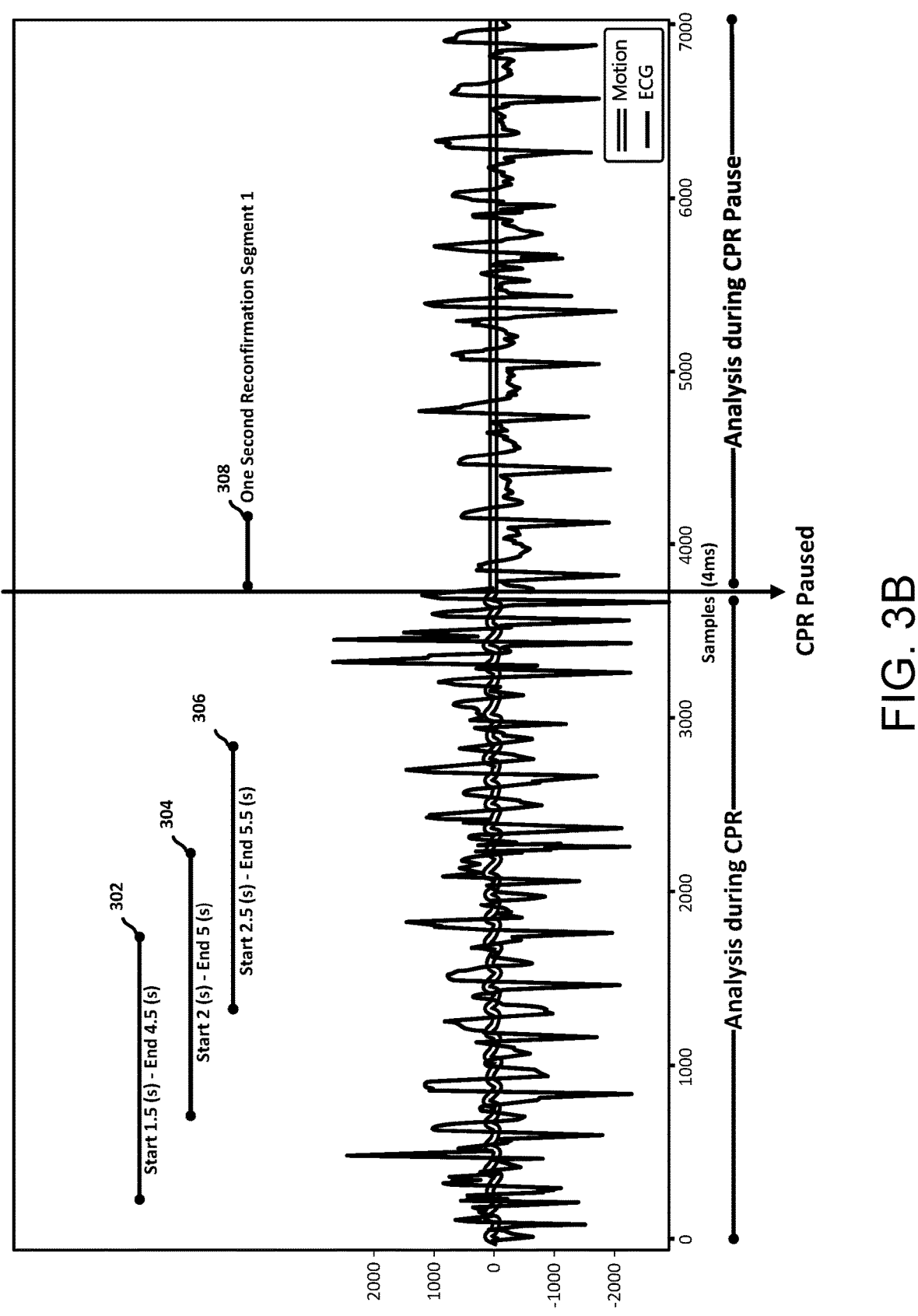
FIG. 3B is a graphical diagram illustrating analysis, by a medical device, of a single segment of sensor data generated from signals acquired during a pause of CPR as part of a mixed-segment analysis process in accordance with at least one example disclosed herein.

Referring now to FIG. 3B, a first 1-second reconfirmation phase is illustrated. In the 1-second reconfirmation phase, the medical device identifies and analyzes a new segment 308 of data generated from signals acquired during a pause in administration of CPR. In this example, in identifying and analyzing the new segment 308, the medical device attempts to confirm previously established preliminary shock/no-shock guidance that is associated with clauses met by the segments 302-306 that generated a vote for 1-second reconfirmation. The new segment 308 can have the attributes of any of the segments 202-208 described above. As shown in FIG. 3B, the segment 308 spans 1 second and starts at a point in time where a pause in CPR is detected.

In the example of FIG. 3B, because the new segment 308 is generated from signals acquired during a pause in CPR, the new segment 308 is expected to be contaminated with less noise due to CPR artifacts than the segments 302-306. As such, the new segment 308 can be used by the medical device to finalize shock/no-shock guidance quickly where the shock/no-shock guidance determined from the new segment 308 agrees with the previously established preliminary shock/no-shock guidance. For instance, in some examples, the medical device can determine whether there is agreement by extracting features from the new segment 308 and comparing those features to one or more clauses associated with shock/no-shock guidance that is the same as the preliminary shock/no-shock guidance. In these examples, the medical device determines that the new segment 308 agrees with the previously established preliminary shock/no-shock guidance and finalizes the previously established shock/no-shock guidance where features of the new segment 308 satisfy one or more of the clauses. Where the medical device is able to finalize the previously established preliminary shock/no-shock guidance, the medical device renders the previously established preliminary shock/no-shock guidance to the healthcare provider of whether the patient's cardiac rhythm is shockable or non-shockable, so as to minimize the pause in CPR.

Alternatively or additionally, in some examples, the medical device can determine to not confirm shock/no-shock guidance using 1-second reconfirmation where an insufficient number of the segments 302-306 generate a vote for 1-second reconfirmation (e.g., due to the ECG characteristics being inconclusive) and/or where one or more of the segments 302-306 are contaminated with excessive noise. Where the medical device is unable to confirm the previously established preliminary shock/no-shock guidance using the new segment 308, the medical device proceeds to a second 1-second reconfirmation phase, which is illustrated by FIG. 3C.

Figure 3C:
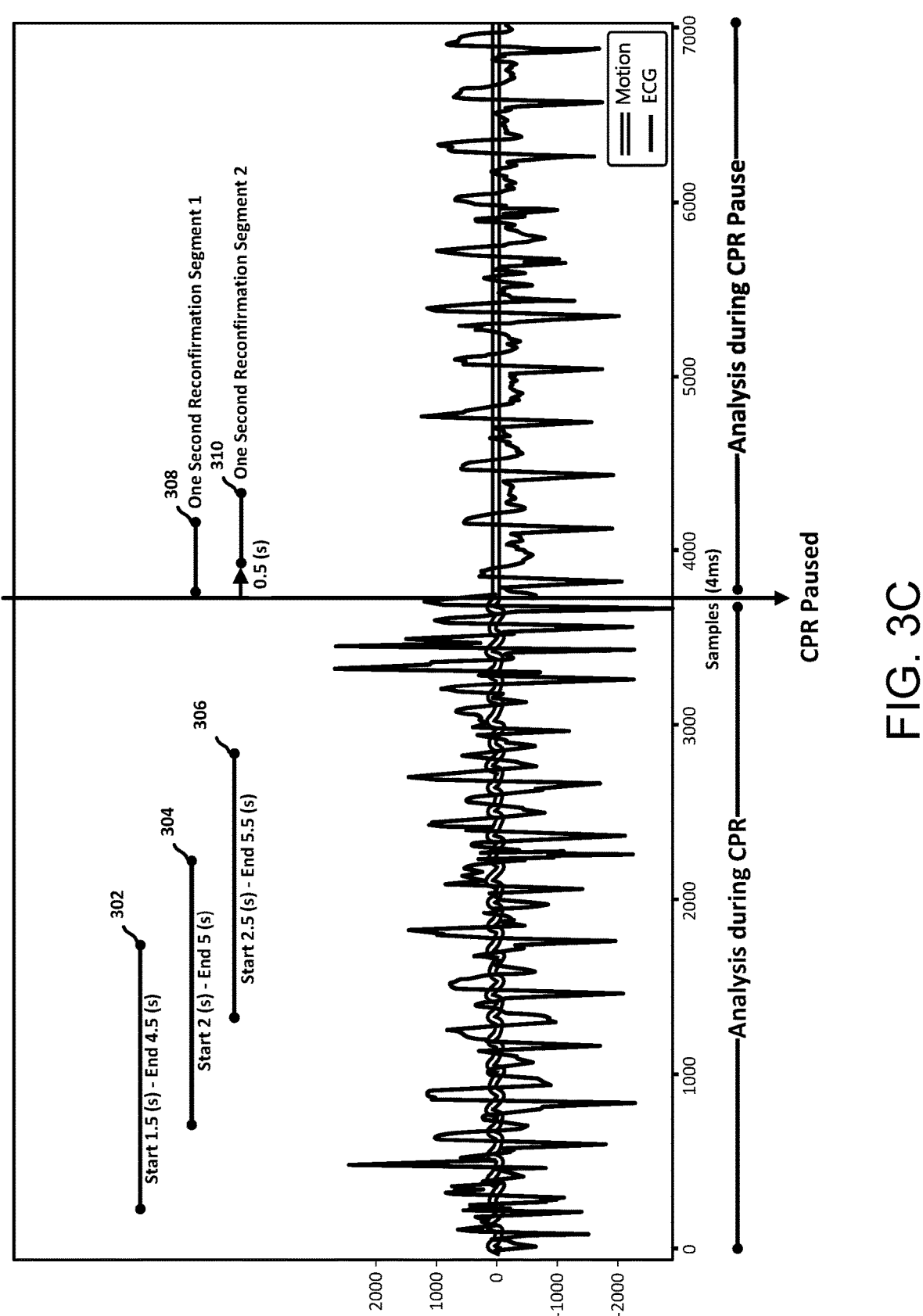
FIG. 3C is a graphical diagram illustrating analysis, by a medical device, of multiple overlapping segments of sensor data generated from signals acquired during a pause of CPR as part of a mixed-segment analysis process in accordance with at least one example disclosed herein.

As shown in FIG. 3C, in the second 1-second reconfirmation phase, the medical device identifies and analyzes a new segment 310 of data generated from signals acquired during a pause in administration of CPR. In this example, in identifying and analyzing the new segment 310, the medical device attempts to confirm previously established preliminary shock/no-shock guidance that is associated with clauses met by the segments 302-306 that generated a vote for 1-second reconfirmation. The new segment 310 can have the attributes of any of the segments 202-208 described above. As shown in FIG. 3B, the segment 310 spans 1 second and starts 0.5 seconds after a point in time where a pause in CPR is detected.

Figure 3D:
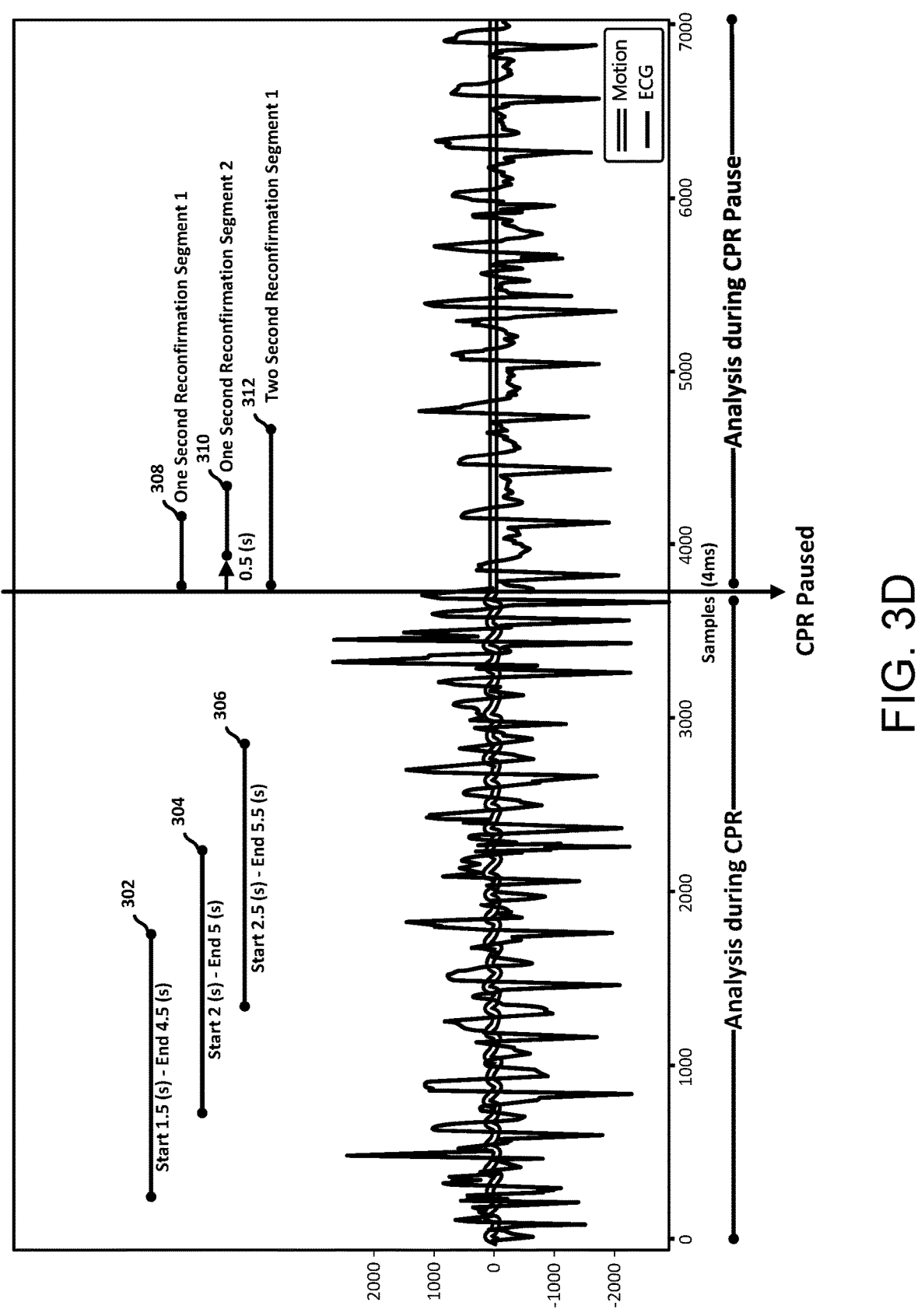
FIG. 3D is a graphical diagram illustrating analysis, by a medical device, of other multiple overlapping segments of sensor data generated from signals acquired during a pause of CPR as part of a mixed-segment analysis process in accordance with at least one example disclosed herein.

In the example of FIG. 3C, because the new segment 310, like the segment 308, is generated from signals acquired during a pause in CPR, the new segment 310 is expected to be contaminated with less noise due to CPR artifacts than the segments 302-306. As such, the new segment 310 can be used by the medical device to finalize shock/no-shock guidance quickly where the shock/no-shock guidance determined from the new segment 310 agrees with the previously established preliminary shock/no-shock guidance. For instance, in some examples, the medical device can determine whether there is agreement by extracting features from the new segment 310 and comparing those features to one or more clauses associated with shock/no-shock guidance that is the same as the preliminary shock/no-shock guidance. In these examples, the medical device determines that the new segment 310 agrees with the previously established preliminary shock/no-shock guidance and finalizes the previously established shock/no-shock guidance where features of the new segment 310 satisfy one or more of the clauses. Where the medical device is able to finalize the previously established preliminary shock/no-shock guidance, the medical device renders the previously established preliminary shock/no-shock guidance to the healthcare provider of whether the patient's cardiac rhythm is shockable or non-shockable, so as to minimize the pause in CPR.

Where the medical device is unable to confirm the previously established preliminary shock/no-shock guidance using the new segment 310, the medical device proceeds to a first phase of 2-second reconfirmation, which is illustrated by FIG. 3D.

FIG. 3D illustrates a phase in which the medical device is configured to identify and analyze a new segment 312 generated from signals acquired during a pause in administration of CPR, which may be in combination with information obtained from segment 308. In this example, in identifying and analyzing the new segment 312, the medical device attempts to confirm previously established preliminary shock/no-shock guidance that is associated with clauses met by the segments 302-306 that generated a vote for 2-second reconfirmation. The new segment 312 can have the attributes of any of the segments 202-208 described above. As shown in FIG. 3D, the segment 312 overlaps with the segments 308 and 310, spans 2 seconds, and starts at a point in time where a pause in CPR is detected.

In the example of FIG. 3D, the new segment 312, like the segments 308 and 310, is generated from signals acquired during a pause in CPR, absent of substantial artifacts due to chest compressions or other CPR activities. As such, the new segment 312, like the segments 308 and 310, and each of which may be taken into account in the analysis, can be used by the medical device to finalize shock/no-shock guidance quickly where the shock/no-shock guidance determined from the new segment 312, optionally in an analysis in combination with that of the segments 308 and 310, agrees with the previously established shock/no-shock guidance. The medical device can, for example, determine whether there is agreement by extracting features from the new segment 312 and comparing those features to clauses associated with shock/no-shock guidance that is the same as the preliminary shock/no-shock guidance. In these examples, the medical device determines that the new segment 312 agrees with the previously established preliminary shock/no-shock guidance and finalizes the previously established shock/no-shock guidance, in the absence of CPR artifact, where features of the new segment 312 satisfy one or more of the clauses. Where the medical device is able to finalize the previously established preliminary shock/no-shock guidance, which had been determined during the CPR period, the medical device renders the previously established shock/no-shock guidance to the healthcare provider, so that the appropriate treatment can be provided as quickly as possible, for example, administering a defibrillation shock and/or minimizing the pause in CPR.

Alternatively or additionally, in some examples, the medical device can determine to not confirm shock/no-shock guidance using 2-second reconfirmation where an insufficient number of segments generated a vote for 2-second reconfirmation and/or where one or more of the segments 302-306 are contaminated with excessive noise. Where the medical device is unable to confirm the previously established preliminary shock/no-shock guidance using the new segment 312, the medical device proceeds to a second phase of 2-second reconfirmation, which is illustrated by FIG. 3E.

Figure 3E:
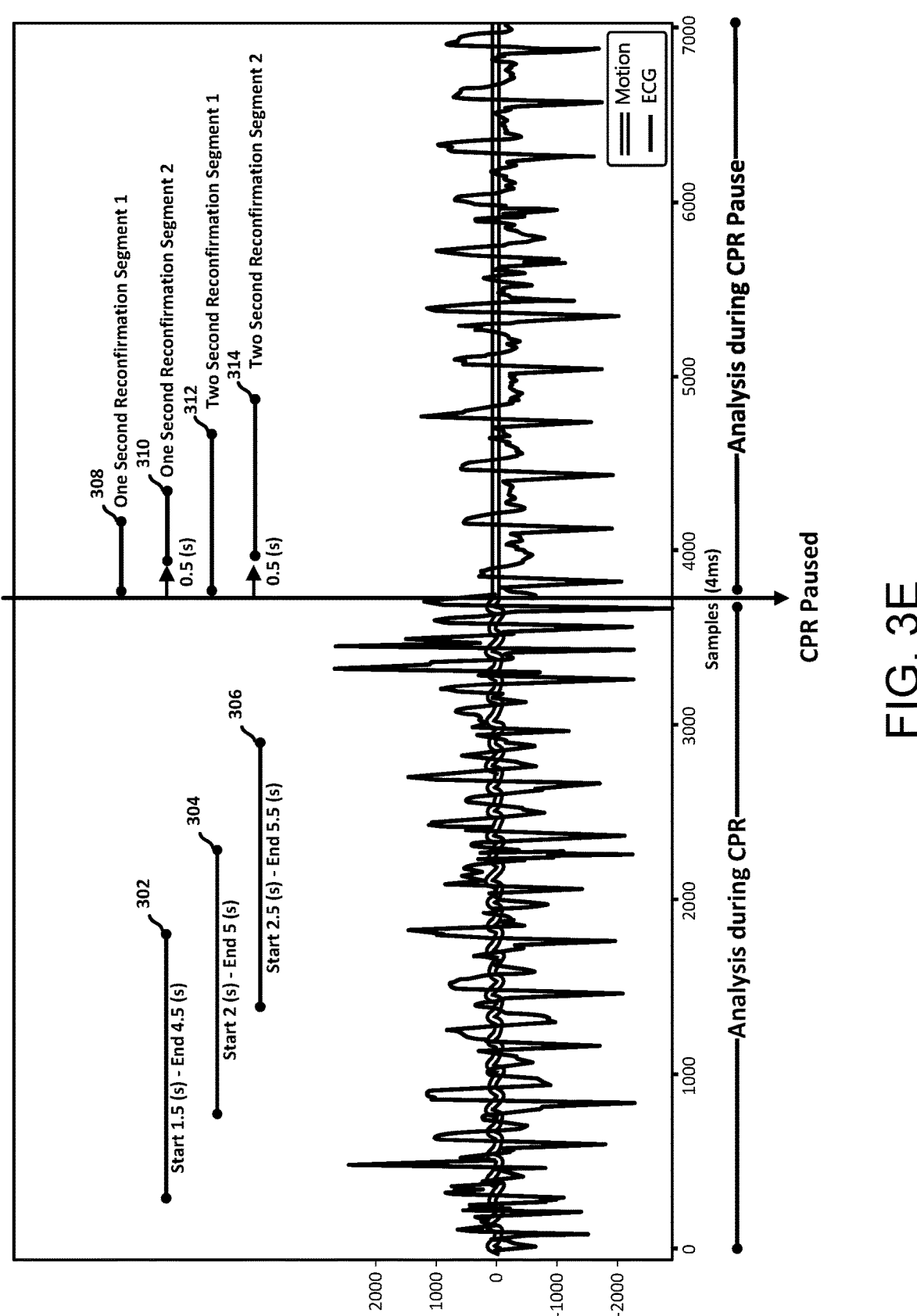
FIG. 3E is a graphical diagram illustrating analysis, by a medical device, of other multiple overlapping segments of sensor data generated from signals acquired during a pause of CPR as part of a mixed-segment analysis process in accordance with at least one example disclosed herein.

FIG. 3E illustrates a phase in which the medical device is configured to identify and analyze a new segment 314 generated from signals acquired during a pause in administration of CPR. In this example, in identifying and analyzing the new segment 314, where such analysis may be in combination with information obtained from segments 308, 310, and 312, the medical device attempts to confirm previously established shock/no-shock guidance that is associated with clauses met by the segments 302-306 that generated a vote for 2-second reconfirmation. The new segment 314 can have the attributes of any of the segments

202-208 described above. As shown in FIG. 3E, the segment 314 overlaps with the segments 308, 310, and 312; spans 2 seconds; and starts at 0.5 seconds after a point in time where a pause in CPR is detected.

Figure 3F:
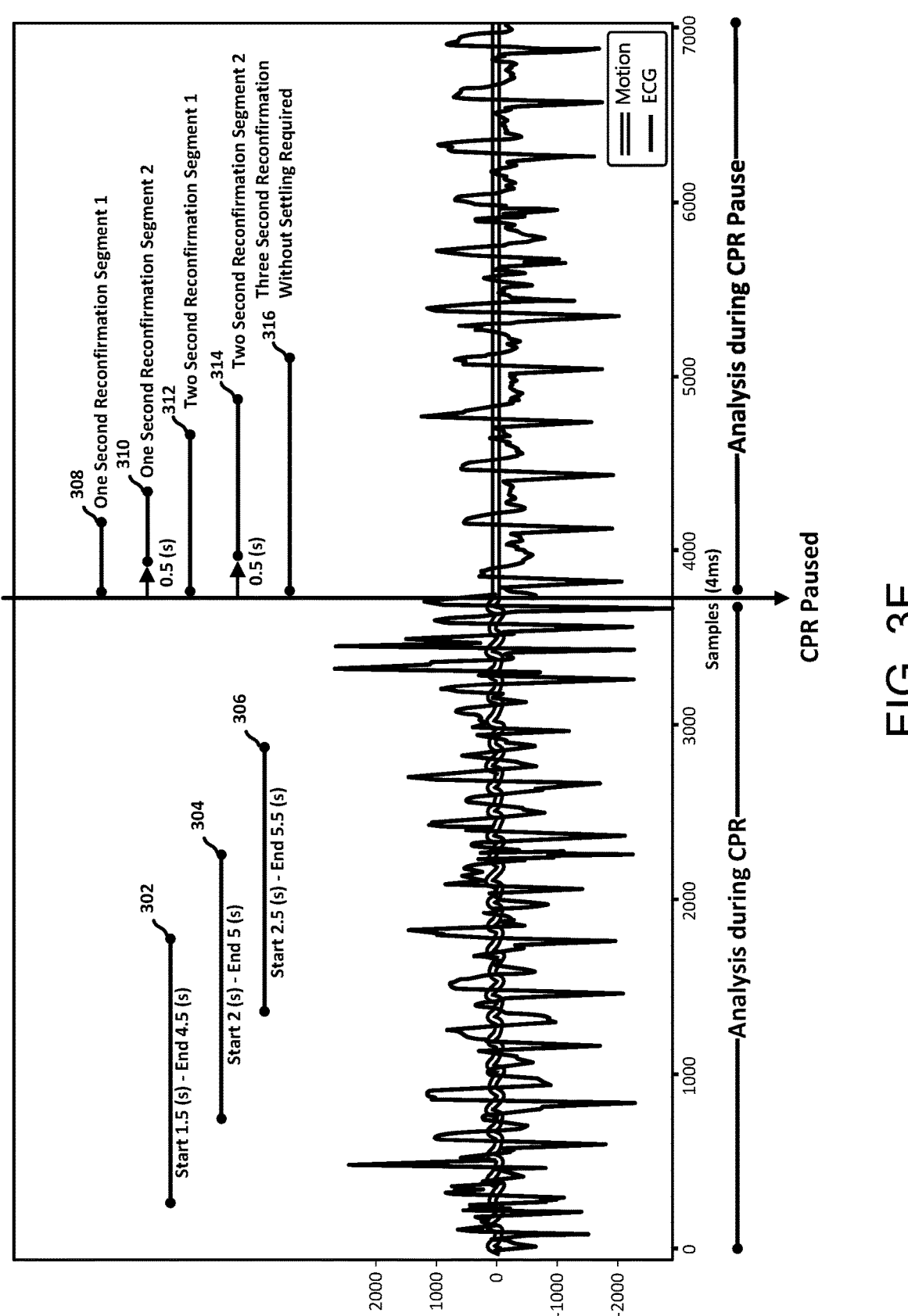
FIG. 3F is a graphical diagram illustrating analysis, by a medical device, of other multiple overlapping segments of sensor data generated from signals acquired during a pause of CPR as part of a mixed-segment analysis process in accordance with at least one example disclosed herein.

In the example of FIG. 3E, the new segment 314, like the segments 308, 310, and 312, is generated from signals acquired during a pause in CPR. As such, the new segment 314, like and optionally along with the segments 308, 310, and 312, can be used by the medical device to finalize shock/no-shock guidance quickly where the shock/no-shock guidance determined from the new segment 314, optionally in an analysis in combination with that of the segments 308, 310 and 312, agrees with the previously established shock/no-shock guidance. The medical device can, for example, determine whether there is agreement by extracting features from the new segment 314 and comparing those features to one or more clauses associated with shock/no-shock guidance that is the same as the preliminary shock/no-shock guidance. In these examples, the medical device determines that the new segment 314, optionally in combination with analysis from segments 308, 310, and 312, agrees with the previously established preliminary shock/no-shock guidance and finalizes the previously established shock/no-shock guidance, which had been determined during the CPR period, where features of the new segment 314 satisfy one or more of the clauses. Where the medical device is able to finalize the previously established shock/no-shock guidance, the medical device renders the shock/no-shock guidance to the healthcare provider, so as to minimize the pause in CPR.

Where the medical device is unable to confirm the previously established preliminary shock/no-shock guidance using the new segment 314, the medical device proceeds to a 3-second reconfirmation without settling time, which is illustrated by FIG. 3F.

FIG. 3F illustrates a phase in which the medical device is configured to identify and analyze a new segment 316 generated from signals acquired during a pause in administration of CPR. In this example, in identifying and analyzing the new segment 316, where such analysis may be in combination with information obtained from segments 308, 310, 312, and 314, the medical device attempts to either identify a high accuracy clause met by the new segment 316 or confirm previously established preliminary shock/no-shock guidance that is associated with clauses met by the segments 302-306 that generated a vote for 3-second reconfirmation. The new segment 316 can have the attributes of any of the segments 202-208 described above. As shown in FIG. 3F, the segment 316 overlaps with the segments 308, 310, 312, and 314; spans 3 seconds; and starts at a point in time where a pause in CPR is detected.

In the example of FIG. 3F, the new segment 316, like the segments 308, 310, 312, and 314 is generated from signals acquired during a pause in CPR. As such, the new segment 316, like and optionally along with the segments 308, 310, 312, and 314 can be used by the medical device to finalize shock/no-shock guidance quickly where the shock/no-shock guidance determined from the new segment 316 agrees with the previously established shock/no-shock guidance. The medical device can, for example, determine whether there is agreement by extracting features from the new segment 316 and comparing those features to one or more clauses associated with shock/no-shock guidance that is the same as the preliminary shock/no-shock guidance. In these examples, the medical device determines that the new segment 316, optionally in combination with analysis from segments 308, 310, 312, and/or 314 agrees with the previously established preliminary shock/no-shock guidance, which had been determined during the CPR period, and finalizes the previously established shock/no-shock guidance where features of the new segment satisfy the clause. Furthermore, in certain examples, the medical device can definitively determine shock/no-shock guidance based on its analysis of the new segment 316 alone by determining that calculated features of the new segment 316 satisfy a high accuracy clause, for example, as described above with reference to FIG. 2. Where the medical device is able to either finalize the previously established shock/no-shock guidance or determine that the new segment 316 meets a high accuracy clause, the medical device renders the shock/no-shock guidance to the healthcare provider, so as to minimize the pause in CPR.

Alternatively or additionally, in some examples, the medical device can determine to not confirm shock/no-shock guidance where an insufficient number of segments generate a vote for 3-second reconfirmation and/or where the segments 302-306 are contaminated with excessive noise. Where the medical device is unable to confirm the previously established preliminary shock/no-shock guidance using the new segment 316 or determine that the new segment 316 meets a high accuracy clause, the medical device proceeds to a non-reconfirmation, which is illustrated by FIG. 3H.

Figure 3G:
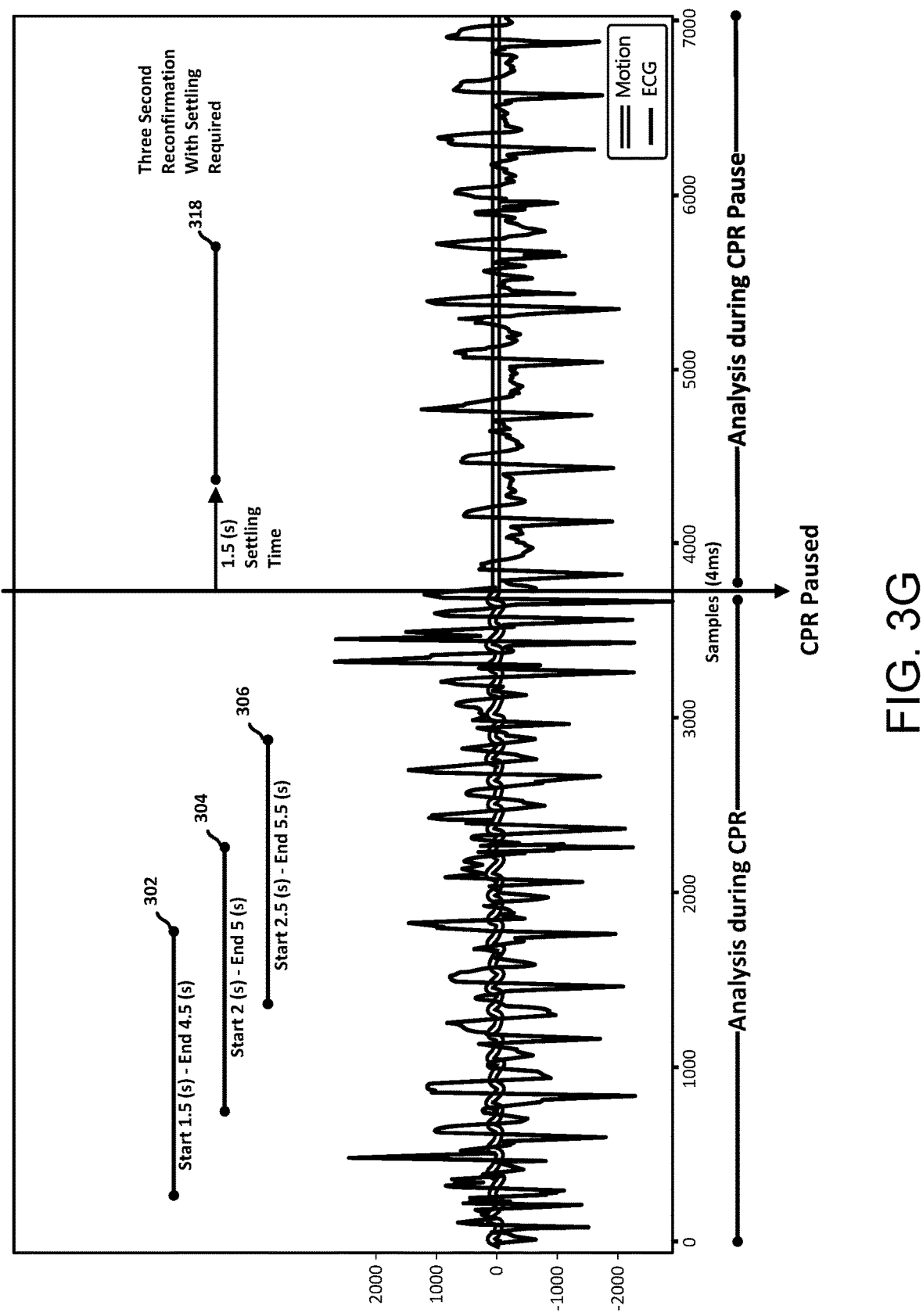
FIG. 3G is a graphical diagram illustrating analysis, by a medical device, of another segment of sensor data generated from signals acquired during a pause of CPR as part of a mixed-segment analysis process in accordance with at least one example disclosed herein.
Figure 3H:
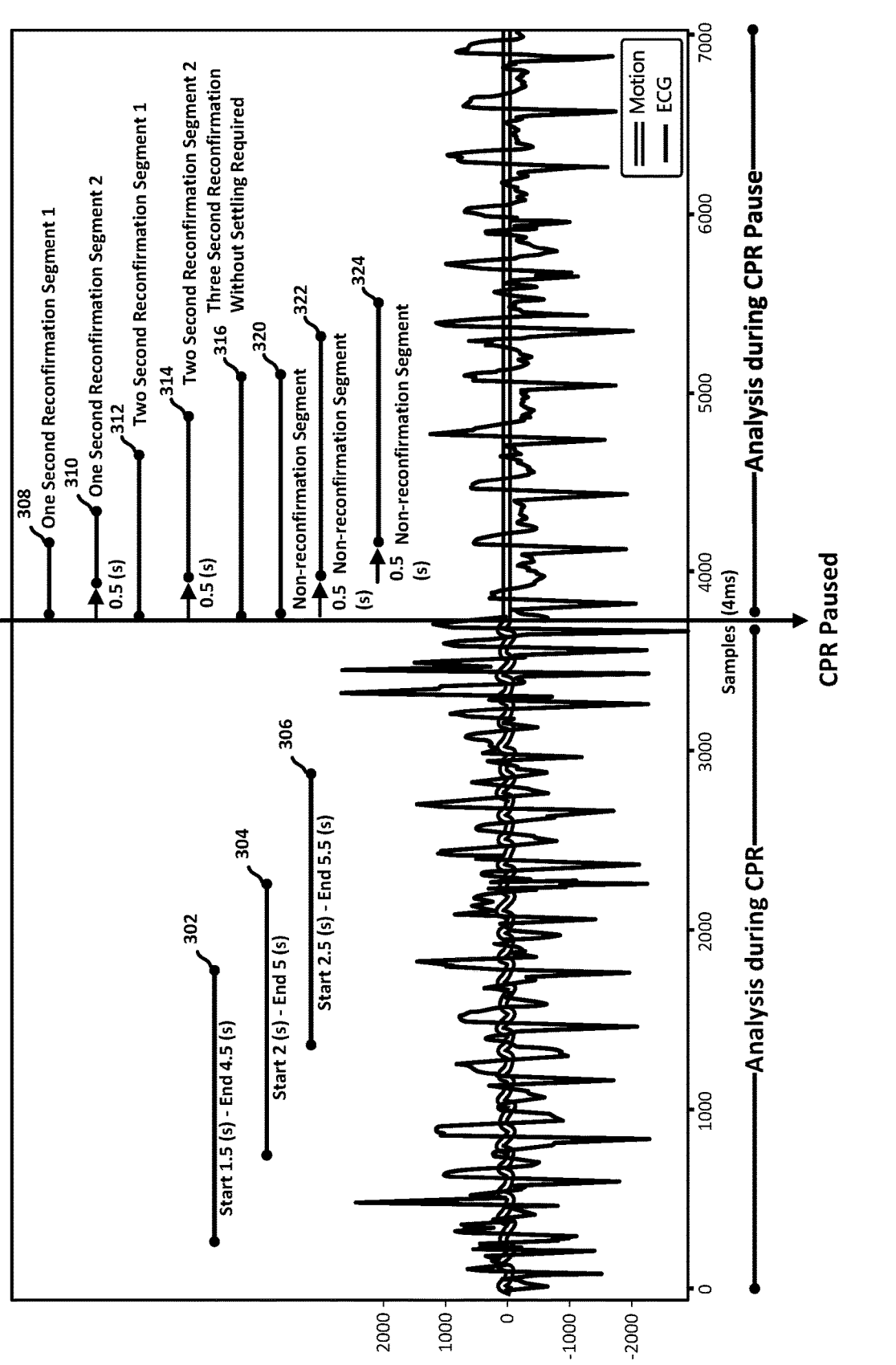
FIG. 3H is a graphical diagram illustrating analysis, by a medical device, of other multiple overlapping segments of sensor data generated from signals acquired during a pause of CPR as part of a mixed-segment analysis process in accordance with at least one example disclosed herein.

FIG. 3G illustrates a phase in which the medical device is configured to identify and analyze a new segment 318 generated from signals acquired during a pause in administration of CPR after a duration of settling time expires. In this example, the medical device is configured to analyze noise within the segments 302-306 in an attempt to identify noise attributes indicative of poor connections between ECG sensors of the medical device and the patient's body. These attributes can include, for instance, low frequency noise (e.g., noise with a frequency of within a range of 0.5 Hz to 1 Hz, a range of 0.75 Hz to 1.5 Hz, a range of 1 Hz to 1.75 Hz, a range of 1.5 Hz to 2 Hz, a range of 0.4 Hz to 2.1 Hz, to name a few ranges). Further, in these examples, the medical device is configured to allocate settling time (e.g., 1.5 seconds) where the noise attributes are identified. This settling time allows the connection between the ECG sensors and the patient's skin to improve due to the absence of movement caused by active administration of CPR. With this improved connection comes improved ECG signal and data quality.

In some examples, in identifying and analyzing the new segment 318, the medical device attempts to either identify a high accuracy clause met by the new segment 318 or confirm previously established preliminary shock/no-shock guidance that is associated with clauses met by the segments 302-306 that generated a vote for 3-second reconfirmation. The new segment 318 can have the attributes of any of the segments 202-208 described above. As shown in FIG. 3G, the segment 318 spans 3 seconds and starts at a point in time 1.5 seconds after a pause in CPR is detected.

In the example of FIG. 3G, the new segment 318 is generated from signals acquired during a pause in CPR. As such, the new segment 318 is expected to be contaminated with less noise than the segments 302-306. In some examples, the new segment 318 can be used by the medical device to finalize shock/no-shock guidance quickly where the shock/no-shock guidance determined from the new segment 318 agrees with the previously established preliminary shock/no-shock guidance. The medical device can, for example, determine whether there is agreement by extracting features from the new segment 318 and comparing those features to clauses associated with shock/no-shock guidance that is the same as the preliminary shock/no-shock guidance. In these examples, the medical device determines that the new segment 318 agrees with the previously established preliminary shock/no-shock guidance and finalizes the shock/no-shock guidance where features of the new segment 318 satisfy one or more of the clauses. Furthermore, in certain examples, the medical device can definitively determine shock/no-shock guidance based on its analysis of the new segment 318 alone by determining that calculated features of the new segment 318 satisfy a high accuracy clause independent of previous analysis that may have been performed during the CPR period, as described above with reference to FIG. 2. Where the medical device is able to either confirm the previously established preliminary shock/no-shock guidance or determine that the new segment 318 satisfies a high accuracy clause, the medical device renders the shock/no-shock guidance to the healthcare provider, so as to minimize the pause in ongoing treatment (e.g., defibrillation, CPR, etc.) after ECG analysis.

Alternatively or additionally, in some examples, the medical device can determine to not confirm shock/no-shock guidance using 3-second reconfirmation with settling time where an insufficient number of segments generate a vote for 3-second reconfirmation and/or provision of settling time and/or where the segments 302-306 are contaminated with excessive noise. Where the medical device is unable to confirm the previously established preliminary shock/no-shock guidance using the new segment 318 or determine that the new segment 318 satisfies a high accuracy clause, the medical device proceeds to a non-reconfirmation phase, which is illustrated by FIG. 3H.

FIG. 3H illustrates a phase in which the medical device is configured to identify and analyze new segments 320-324 generated from signals acquired during a pause in administration of CPR. In this example, in identifying and analyzing the new segments 320-324, the medical device attempts to either identify a high accuracy clause satisfied by one of the new segments 320-324 or identify a threshold number of normal accuracy clauses satisfied by the new segments 320-324 and associated with the same shock/no-shock guidance. The new segments 320-324 can have the attributes of any of the segments 202-208 described above. As shown in FIG. 3H, each of the segments 320-324 spans 3 seconds and each of the segments 322 and 324 is offset 0.5 seconds from the previous segment. As shown in FIG. 3H, the segment 320 begins immediately after detection of a pause in CPR, the segment 322 begins 0.5 seconds after detection of the pause in CPR, and the segment 324 begins 1 second after detection of the pause in CPR.

In the example of FIG. 3H, the new segments 320-324, like the segments 308-316, are generated from signals acquired during a pause in CPR. As such, the new segments 320-324 are expected to be contaminated with less noise (e.g., due to CPR artifact) than the segments 302-306. In some examples, the new segments 320-324 can be used by the medical device to determine shock/no-shock guidance associated with normal clauses met by a majority of the new segments 320-324 and/or shock/no-shock guidance associated with at least one high accuracy clause met by one of the new segments 320-324. The medical device can, for example, make these determinations by extracting features from one or more of the new segments 320-324 and comparing those features to one or more high and/or normal accuracy clauses. Where the medical device determines that at least one of the new segments 320-324 meets a high accuracy clause, the medical device renders shock/no-shock guidance associated with the satisfied high accuracy clause to the healthcare provider. Where the medical device determines that a threshold number of the new segments 320-324 meet normal accuracy clauses, the medical device renders shock/no-shock guidance associated with the met normal accuracy clauses to the healthcare provider. Subsequent to rendering the shock/no-shock guidance, the medical device continues to identify and analyze data segments generated from sensor signals.

Figure 4A:
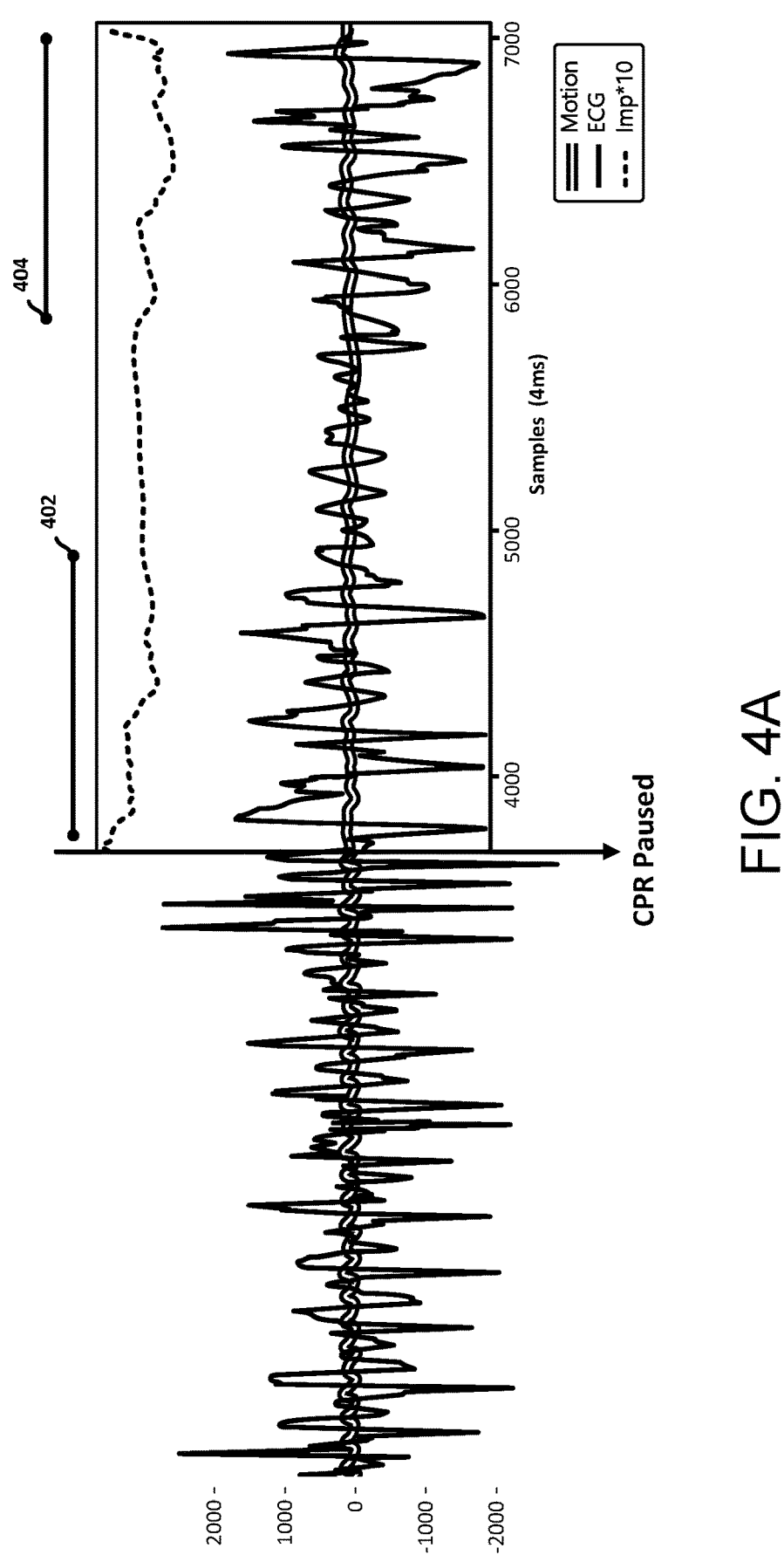
FIG. 4A is a graphical diagram illustrating analysis, by a medical device, of segments of sensor data for noise as part of a mixed-segment analysis process in accordance with at least one example disclosed herein.
Figure 4B:
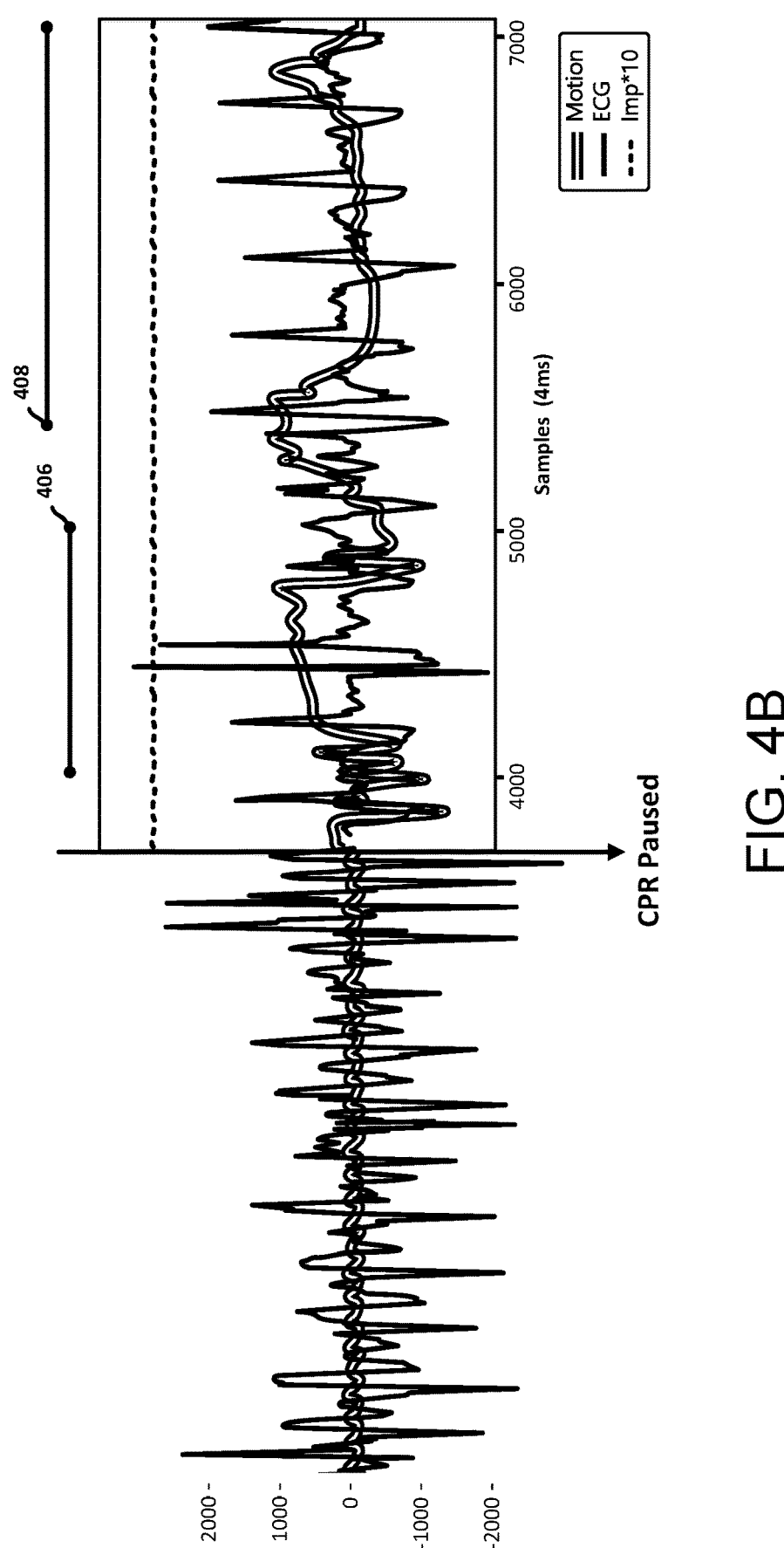
FIG. 4B is a graphical diagram illustrating analysis, by a medical device, of segments of sensor data for noise as part of a mixed-segment analysis process in accordance with at least one example disclosed herein.

Turning to FIGS. 4A and 4B, examples are illustrated in which a medical device (e.g., the AED 100 of FIG. 1) analyzes ECG data, motion data, and/or impedance data to determine whether sensor data is contaminated with excessive noise. This noise analysis can be applied to individual segments, such as the segments 202-208 described above with reference to FIG. 2, and can be applied to sensor data generated from signal acquired during an active CPR cycle and/or during a pause in CPR.

FIG. 4A illustrates an example in which the medical device identifies noise by detecting spikes in the ECG data and variability in impedance data. In the example of FIG. 4A, the medical device detects excessive noise in segments 402 and 404 due to the standard deviation in impedance within the segments exceeding a deviation threshold in combination with the presence of spikes in amplitude of the ECG data within the segments transgressing an amplitude threshold. In various examples, the deviation threshold for impedance can vary between 2 ohms to 10 ohms. In certain examples, the amplitude threshold can vary between 1 millivolt (mV) and 5 mV.

FIG. 4B illustrates an example in which the medical device identifies noise by detecting spikes in the amplitude of ECG data and variability in motion data. In the example of FIG. 4B, the medical device detects excessive noise in segments 406 and 408 due to the standard deviation in motion data within the segments exceeding a deviation threshold in combination with the presence of spikes in amplitude of the ECG data within the segments transgressing an amplitude threshold. In various examples, the deviation threshold for motion can vary between 20 (milli-G's) mG and 100 mG. In certain examples, the amplitude threshold can vary between 1 mV and 5 mV. It should be noted that, in some examples, the medical device identifies noise in segments where variability in motion data and variability in impedance coincides with spikes in the amplitude of ECG data.

Figure 5:
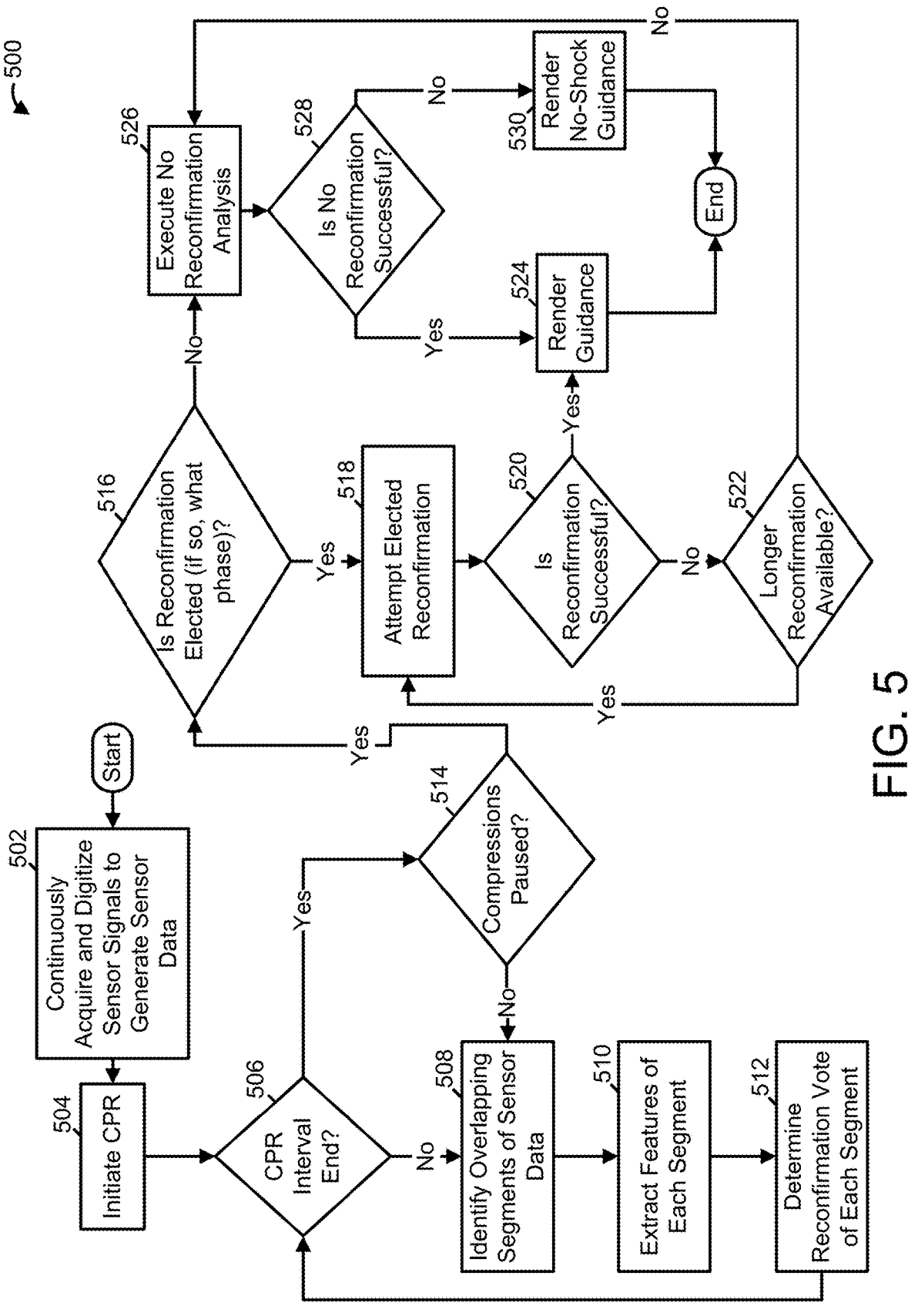
FIG. 5 is a flow diagram illustrating a mixed-segment analysis process in accordance with at least one example disclosed herein.

Turning now to FIG. 5, a mixed-segment analysis process 500 is illustrated. A variety of medical devices, such as the AED 100 described above with reference to FIG. 1, can be configured to execute the mixed-segment analysis process 500, in accordance with the examples described herein.

As shown in FIG. 5, the process 500 starts with the medical device acquiring and digitizing 502, sensor signals to generate sensor data. In some examples, the operation 502 is executed continuously and concurrently with the other operations of the process 500. The sensor data acquired and digitized by the medical device within the operation 502 includes ECG data, motion data, and impedance data.

Continuing with the process 500, the medical device initiates 504 a CPR interval by, for example, prompting a healthcare provider (e.g., the healthcare provider 102 of FIG. 1) to begin a new cycle of CPR. Within the operation 504, the medical device can prompt the healthcare provider via, for example, a user interface of the medical device.

Continuing with the process 500, the medical device determines 506 whether the end of the current CPR interval has been reached (e.g. 15 seconds have elapsed and/or 30 chest compressions and 2 rescue breaths have been administered since the operation 504). Where the medical device determines 506 that the end of the current CPR interval has been reached, the medical device prompts the healthcare provider to cease active CPR activities and disengage from the patient. In this instance, the medical device next proceeds to operation 514. Where the medical device determines 506 that the end of the current CPR interval has not been reached, the medical device proceeds to operation 508.

Continuing with the process 500, the medical device identifies 508 overlapping segments of sensor data. These segments can include, for example, the segments 302-306 described above with reference to FIG. 3A. As such, the overlapping segments identified 508 can include, for example, ECG data, motion data, and/or impedance data generated from signals acquired during an active CPR cycle.

Continuing with the process 500, the medical device extracts 510 features from each identified segment of data. These features can include, for example, any of the features of the segments 202-208 described above with reference to FIG. 2. The medical device next determines 512 a vote for each segment. For instance, the medical device can compare the extracted features of each segment to one or more clauses to determine whether the extracted features meet any of the one or more sets of criteria associated with the reconfirmation phases. Where the extracted features of a segment meet a set of criteria, the medical device records a vote for a reconfirmation phase associated with the met set of criteria. Some examples of reconfirmation phases for which votes can be recorded are described above with reference to FIG. 3A.

Continuing with the process 500, the medical device determines 514 whether CPR is paused (e.g., whether CPR compressions have ceased). For instance, in some examples, the medical device can analyze motion data generated in the operation 502 to identify cessation of rhythmic up and down movement of the parts of the medical device. These parts may include, for example, a chest compression sensor and/or a therapy pad. The therapy pad may include sensing and/or therapy electrodes where the medical device is an AED. In some examples, the medical device determines 514 that CPR has been paused after no up and down movement has been detected for a threshold period of time. In certain examples, the threshold period of time is 1 second. In some examples, this threshold period of time is decreased where no up and down movement is detected within another threshold period of time (e.g. 0.5 seconds) from issuance of a prompt to the healthcare provider to pause CPR. Where the medical device determines 514 that CPR is not paused, the medical device continues to identify 508 overlapping segments of sensor data. Where the medical device determines 514 that CPR is paused, the medical device starts a new analysis interval and proceeds to operation 516. It should be noted that sensor information acquired during the threshold period of time used to detect cessation of compressions can be included in segments analyzed by the various reconfirmation (and no reconfirmation) processes described herein to reach accurate shock/no-shock guidance quickly.

Continuing with the process 500, the medical device determines 516 whether reconfirmation is elected. For instance, the medical device can determine 516 whether enough votes are recorded to elect a reconfirmation phase (e.g., by comparing a number of votes determined 512 to one or more thresholds). For instance, a particular reconfirmation phase can be elected where an overall minimum number of votes (e.g. 8 votes) are recorded and the reconfirmation phase receives the most recorded votes. Where enough votes are recorded and a reconfirmation phase receives the most recorded votes, the medical device determines 516 that reconfirmation is elected and proceeds to operation 518. Where not enough votes are recorded or a reconfirmation phase does not receive the most recorded votes (e.g., no reconfirmation due to noise receives the most votes), the medical device proceeds to operation 526.

Continuing with the process 500, the medical device attempts 518 to confirm previously established preliminary shock/no-shock guidance using the reconfirmation phase that receives the most recorded votes. Examples of various reconfirmation phases are described above with reference to FIGS. 3A-3G. The medical device next determines 520 whether reconfirmation is successful. Where the medical device determines 520 that reconfirmation is successful, the medical device proceeds to operation 524. Where the medical device determines 520 that reconfirmation is not successful, the medical device proceeds to the operation 522.

Continuing with the process 500, the medical device determines 522 whether a longer reconfirmation phase is available. For instance, where the reconfirmation phase attempted was 1-second reconfirmation, the medical device determines 522 that 2-second reconfirmation is available and proceeds to attempt 518 2-second reconfirmation. Where the reconfirmation phase attempted was 2-second reconfirmation, the medical device determines 522 that 3-second reconfirmation is available and proceeds to attempt 518 3-second reconfirmation. Where the reconfirmation phase attempted was 3-second reconfirmation, the medical device determines 522 that no longer reconfirmation phase is available and proceeds to operation 526. Continuing with the process 500, the medical device executes 526 a no reconfirmation phase. One example of a no reconfirmation phase is described above with reference to FIG. 3H. Next, the medical device determines 528 whether the no reconfirmation phase is successful. Where the medical device determines 528 that the no reconfirmation phase is successful, the medical device proceeds to operation 524. In the operation 524, the medical device renders 524 (e.g., via a user interface) shock/no-shock guidance determined from successful execution of the operation 520 or the operation 528, and the process 500 ends. Where the medical device determines 528 that the reconfirmation phase is not successful, the medical device proceeds to the operation 530. In the operation 530, the medical device renders 530 no-shock guidance, having reached inconclusive results, and the process 500 ends.

Turning now to FIG. 6A-6G, a mixed-segment analysis process 600 is illustrated. A variety of medical devices, such as the AED 100 described above with reference to FIG. 1, can be configured to execute the mixed-segment analysis process 600, in accordance with the examples described herein.

Figure 6A:
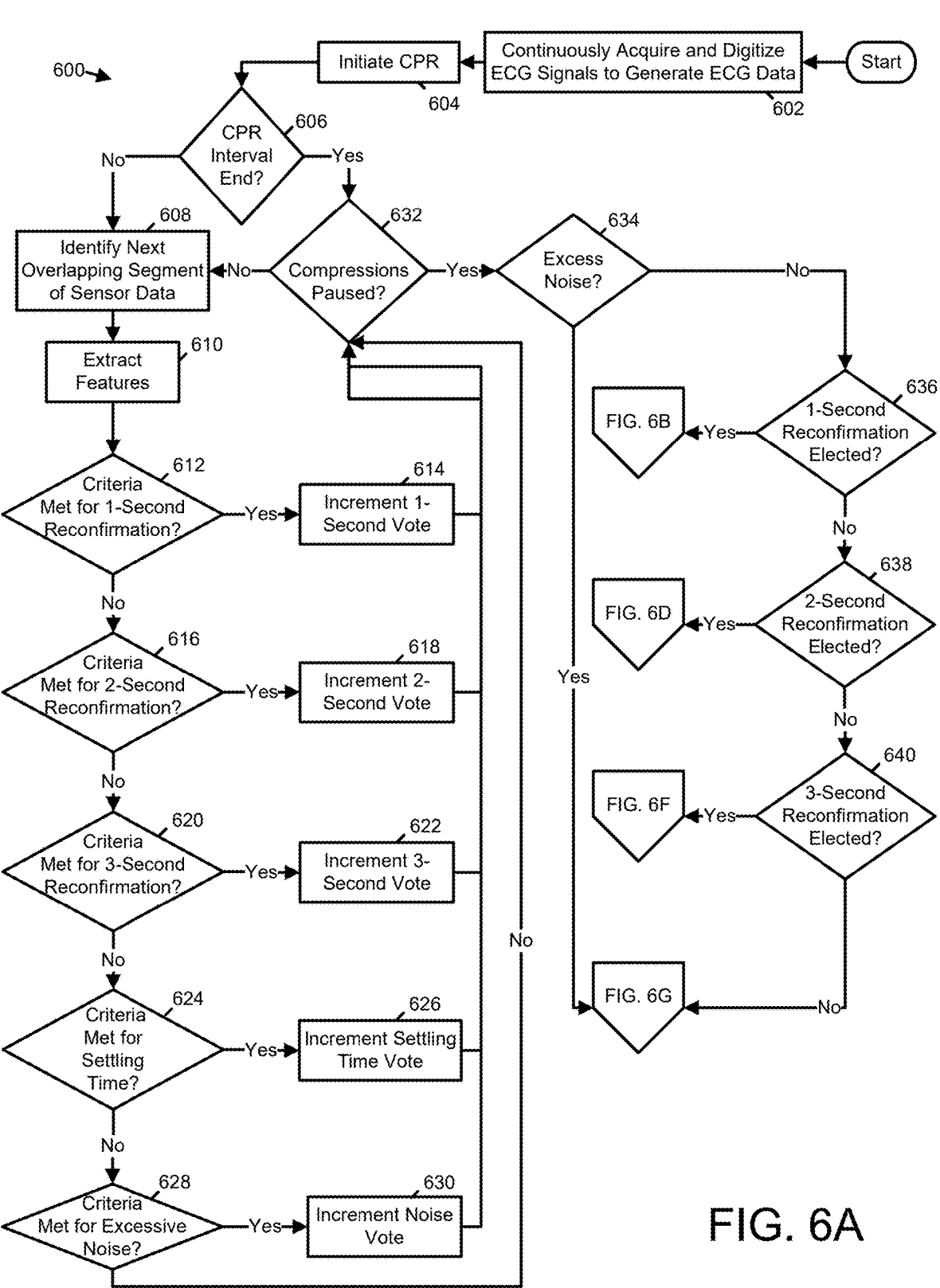
FIG. 6A is a flow diagram illustrating select portions of a mixed-segment analysis process in accordance with at least one example disclosed herein.

As shown in FIG. 6A, the process 600 starts with the medical device acquiring and digitizing 602, sensor signals to generate sensor data. In some examples, the operation 602 is executed continuously and concurrently with the other operations of the process 600. The sensor data acquired and digitized by the medical device within the operation 602 includes ECG data, motion data, and impedance data.

Continuing with the process 600, the medical device initiates 604 a CPR interval by, for example, prompting a healthcare provider (e.g., the healthcare provider 102 of FIG. 1) to begin a new cycle of CPR. Within the operation 604, the medical device can prompt the healthcare provider via, for example, a user interface of the medical device.

Continuing with the process 600, the medical device determines 606 whether the end of the current CPR interval has been reached (e.g. 15 seconds has elapsed and/or 30 chest compressions and 2 rescue breaths have been administered since the operation 604). Where the medical device determines 606 that the end of the current CPR interval has been reached, the medical device prompts the healthcare provider to cease active CPR activities and disengage from the patient. In this instance, the medical device next proceeds to operation 632. Where the medical device determines 606 that the end of the current CPR interval has not been reached, the medical device proceeds to operation 608.

Continuing with the process 600, the medical device identifies 608 a next overlapping segment of sensor data. This segment can include, for example, any of the segments 302-306 described above with reference to FIG. 3A. As such, the overlapping segment identified 608 can include, for example, ECG data, motion data, and/or impedance data generated from signals acquired during an active cycle of CPR.

Continuing with the process 600, the medical device extracts 610 features from the identified segment of data. These features can include, for example, any of the features of the segments 202-208 described above with reference to FIG. 2. The medical device next determines 612 whether the identified segment meets the criteria for 1-second reconfirmation. For instance, in some examples, the medical device can determine 612 whether the features of the identified segment satisfy a clause associated with 1-second reconfirmation. In these examples, the medical device determines 612 that the identified segment meets the criteria for 1-second reconfirmation where the features of the identified segment satisfy a clause associated with 1-second reconfirmation. Where the identified segment meets the criteria for 1-second reconfirmation, the medical device records 614 a vote for 1-second reconfirmation. Where the identified segment does not meet the criteria for 1-second reconfirmation, the medical device proceeds to operation 616.

Continuing with the process 600, the medical device determines 616 whether the identified segment meets the criteria for 2-second reconfirmation. For instance, in some examples, the medical device can determine 616 whether the features of the identified segment satisfy a clause associated with 2-second reconfirmation. In these examples, the medical device determines 616 that the identified segment meets the criteria for 2-second reconfirmation where the features of the identified segment satisfy a clause associated with 2-second reconfirmation. Where the identified segment meets the criteria for 2-second reconfirmation, the medical device records 618 a vote for 2-second reconfirmation. Where the identified segment does not meet the criteria for 2-second reconfirmation, the medical device proceeds to operation 620.

Continuing with the process 600, the medical device determines 620 whether the identified segment meets the criteria for 3-second reconfirmation. For instance, in some examples, the medical device can determine 620 whether the features of the identified segment satisfy a clause associated with 3-second reconfirmation. In these examples, the medical device determines 620 that the identified segment meets the criteria for 3-second reconfirmation where the features of the identified segment satisfy a clause associated with 3-second reconfirmation. Where the identified segment meets the criteria for 3-second reconfirmation, the medical device records 622 a vote for 3-second reconfirmation. Where the identified segment does not meet the criteria for 3-second reconfirmation, the medical device proceeds to operation 624.

Continuing with the process 600, the medical device determines 624 whether the identified segment meets criteria for provision of settling time. For instance, in some examples, the medical device can determine 624 whether the identified segment exhibits noise likely to be absent during a pause in CPR (e.g., low frequency noise generated by CPR activities). In these examples, the medical device determines 624 that the identified segment meets the criteria for provision of settling time where the identified segment exhibits noise likely to be absence during a pause in CPR. Where the identified segment meets the criteria for provision of settling time, the medical device records 626 a vote for provision of settling time. Where the identifier segment does not meet the criteria for provision of settling time, the medical device proceeds to operation 628.

Continuing with the process 600, the medical device determines 628 whether the identified segment meets the criteria for excessive noise. For instance, in some examples, the medical device determines 628 that the identified segment meets the criteria for noise where ECG data within the segment indicates ECG sensor saturation (e.g., the amplitude of the ECG data increases to and beyond the dynamic range of the ECG sensor) and/or where the ECG data includes amplitudes that exceed a noise threshold. Examples of this noise threshold can include amplitude values falling within a range of 2 mV to 7 mV. Where the identified segment meets the criteria for noise, the medical device records 630 a vote for excessive noise. Where the identified segment does not meet the criteria for noise, the medical device proceeds to the operation 632.

Continuing with the process 600, the medical device determines 632 whether CPR is paused (e.g., whether CPR compressions have ceased). For instance, in some examples, the medical device can analyze motion data generated in the operation 602 to identify cessation of rhythmic up and down movement of the parts of the medical device. These parts may include, for example, a chest compression sensor and/or a therapy pad. The therapy pad may include sensing and/or therapy electrodes where the medical device is an AED. In some examples, the medical device determines 632 that CPR has been paused after no up and down movement has been detected for a threshold period of time. In certain examples, the threshold period of time is 1 second. In some examples, this threshold period of time is decreased where no up and down movement is detected within another threshold period of time (e.g. 0.5 seconds) from issuance of a prompt to the healthcare provider to pause CPR. Where the medical device determines 632 that CPR is not paused, the medical device continues to identify 608 overlapping segments of sensor data. Where the medical device determines 632 that CPR is paused, the medical device starts a new analysis interval and proceeds to operation 634. It should be noted that sensor information acquired during the threshold period of time used to detect cessation of compressions can be included in segments analyzed by the various reconfirmation (and no reconfirmation) processes described herein to reach accurate shock/no-shock guidance quickly.

Continuing with the process 600, the medical device determines 634 whether too many of the segments have excessive noise to allow for any sort of reconfirmation. For instance, in some examples, the medical device compares the total number of votes for excessive noise generated by the operation 628 to a noise vote threshold. In these examples, the medical device determines 634 that the overlapping segments include too many segments with excessive noise to allow for reconfirmation where the total number of votes exceeds the noise vote threshold. In some examples, the noise vote threshold is set to 1 vote, so that even 1 segment of excessive noise prevents reconfirmation. In some examples, the noise vote threshold is set to a number that represents a majority of the segments identified 608. Other noise vote thresholds are possible. Where the medical device determines 634 that the overlapping segments do not include too many segments with excessive noise to allow for recon-firmation, the medical device proceeds to operation 636. Where the medical device determines 634 that the overlapping segments include too many segments with excessive noise to allow for reconfirmation, the medical device proceeds to operation 698 illustrated in FIG. 6G. It should also be noted that, in some examples, the medical device limits its determination 634 of whether too many segments have excessive noise to a rolling window of segments having a number of segments equal to a quorum threshold (e.g., 15 segments). This feature prevents stale, noisy segments from preventing reconfirmation using fresh, clean segments generated from later acquired sensor data.

Continuing with the process 600, the medical device determines 636 whether 1-second reconfirmation is elected. For instance, in some examples, the medical device compares the total number of votes for 1-second reconfirmation recorded by the operation 614 to a threshold. This threshold may be, for example, a value equal to a number that represents a majority of the votes recorded in the operations 614, 618, 622, 626, and/or 630. In these examples, the medical device determines 636 that 1-second reconfirmation is elected where the total number of votes for 1-second reconfirmation exceeds the threshold. Where the medical device determines 636 that 1-second reconfirmation is elected, the medical device proceeds to operation 642 illustrated in FIG. 6B. Where the medical device determines 636 that 1-second reconfirmation is not elected, the medical device proceeds to operation 638.

Continuing with the process 600, the medical device determines 638 whether 2-second reconfirmation is elected. For instance, in some examples, the medical device compares the total number of votes for 2-second reconfirmation recorded by the operation 618 to a threshold. This threshold may be, for example, a value equal to a number that represents a majority of the votes recorded in the operations 614, 618, 622, 626, and/or 630. In these examples, the medical device determines 638 that 2-second reconfirmation is elected where the total number of votes for 2-second reconfirmation exceeds the threshold. Where the medical device determines 638 that 2-second reconfirmation is elected, the medical device proceeds to operation 662 illustrated in FIG. 6D. Where the medical device determines 638 that 2-second reconfirmation is not elected, the medical device proceeds to operation 640.

Continuing with the process 600, the medical device determines 640 whether 3-second reconfirmation is elected. For instance, in some examples, the medical device compares the total number of votes for 3-second reconfirmation recorded by the operation 622 to a threshold. This threshold may be, for example, a value equal to a number that represents a majority of the votes recorded in the operations 614, 618, 622, 626, and/or 630. In these examples, the medical device determines 640 that 3-second reconfirmation is elected where the total number of votes for 3-second reconfirmation exceeds the threshold. Where the medical device determines 640 that 3-second reconfirmation is elected, the medical device proceeds to operation 682 illustrated in FIG. 6F. Where the medical device determines 640 that 3-second reconfirmation is not elected, the medical device proceeds to operation 698 illustrated in FIG. 6G.

Figure 6B:
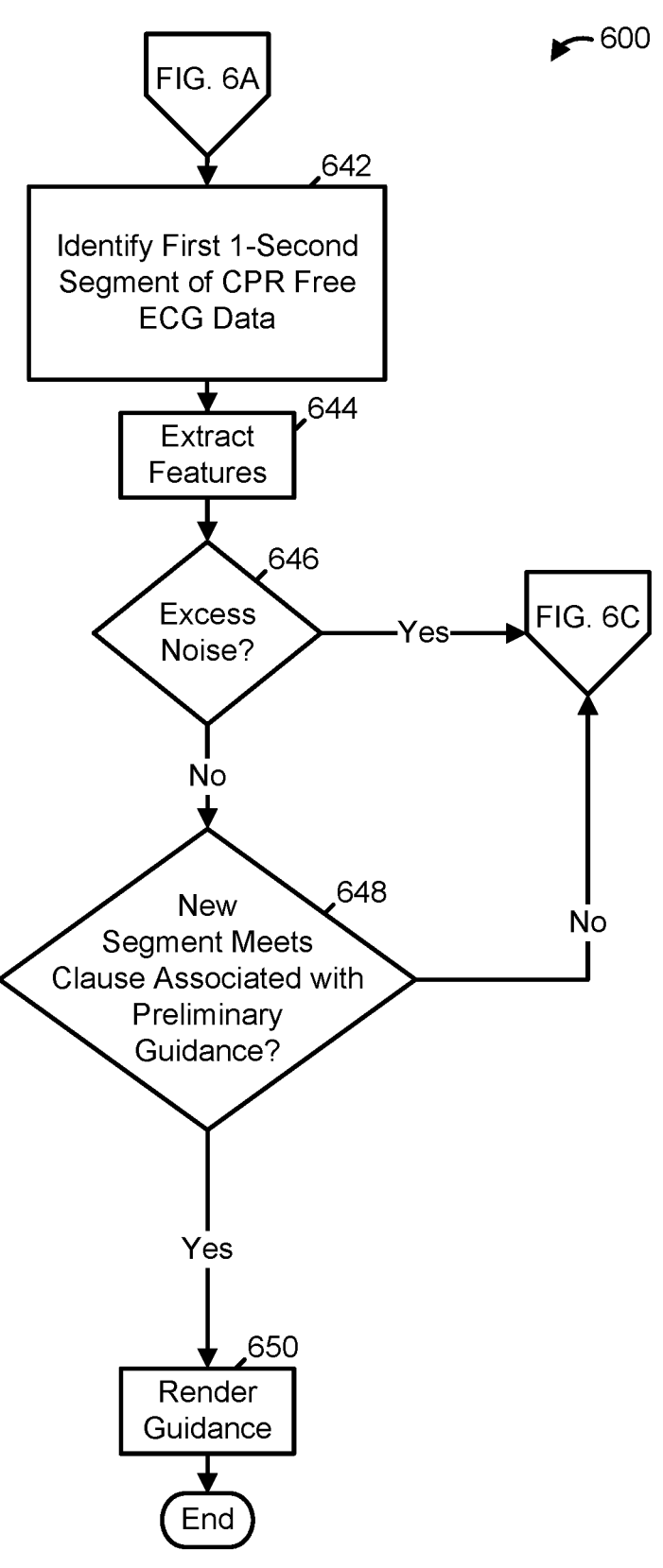
FIG. 6B is a flow diagram illustrating other select portions of a mixed-segment analysis process in accordance with at least one example disclosed herein.

Continuing with the process 600 with reference to FIG. 6B, the medical device identifies 642 a first one second segment of sensor data (e.g., the segment 308 of FIG. 3B) generated from sensor signals acquired during a pause in CPR. The identified segment of sensor data can include, for example, ECG data, motion data, and/or impedance data. The medical device next extracts 644 features from the identified segment. These features can include, for example, any of the features of the segments 202-208 described above with reference to FIG. 2.

Figure 6C:
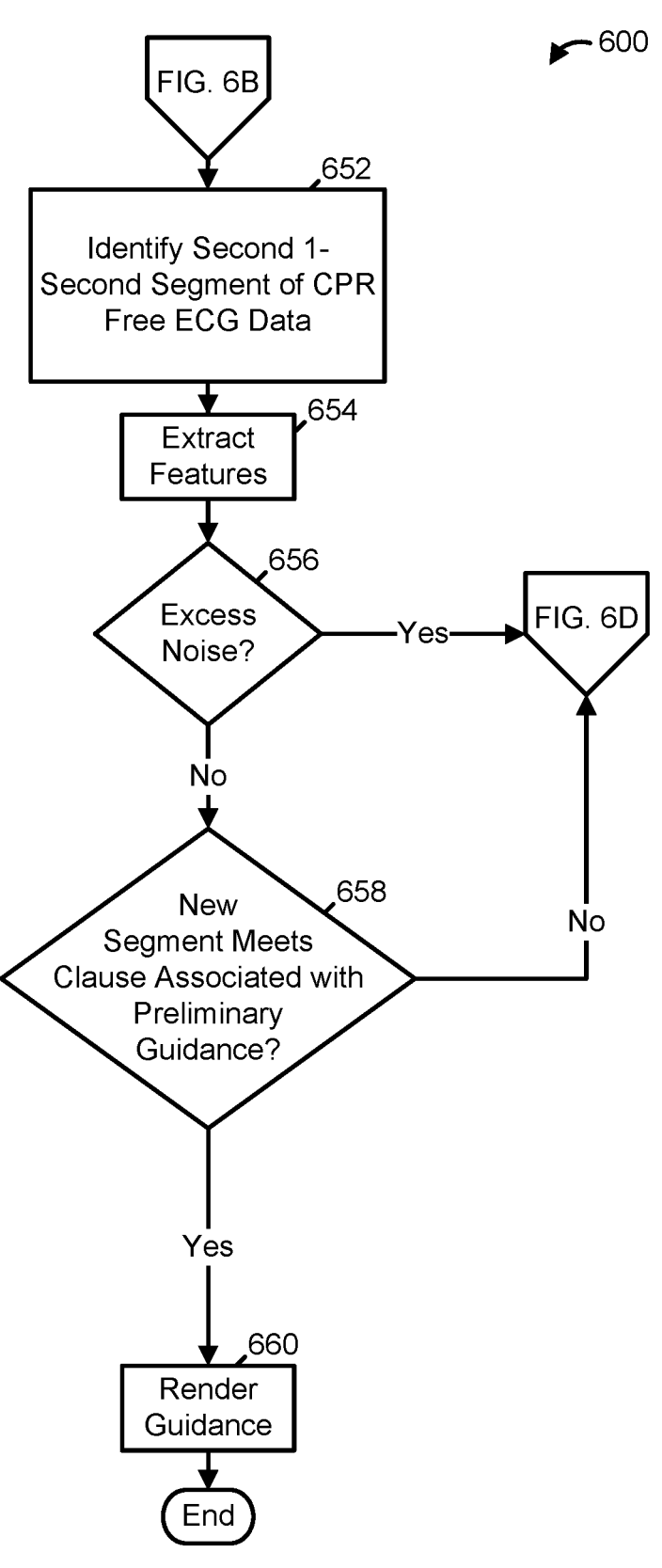
FIG. 6C is a flow diagram illustrating other select portions of a mixed-segment analysis process in accordance with at least one example disclosed herein.

Continuing with the process 600, the medical device determines 646 whether the identified segment includes excessive noise. For instance, in some examples, the medical device can execute a noise detection process (e.g. the noise detection process 700 of FIG. 7) to determine 646 whether the identified segment is contaminated with excessive noise. In these examples, the medical device determines 646 that the identified segment includes excessive noise where the noise detection process declares the same within the identified segment. Where the medical device determines 646 that the identified segment does not include excessive noise, the medical device proceeds to operation 648. Where the medical device determines 646 that the identified segment includes excessive noise, the medical device proceeds to operation 652 as illustrated in FIG. 6C.

Figure 7:
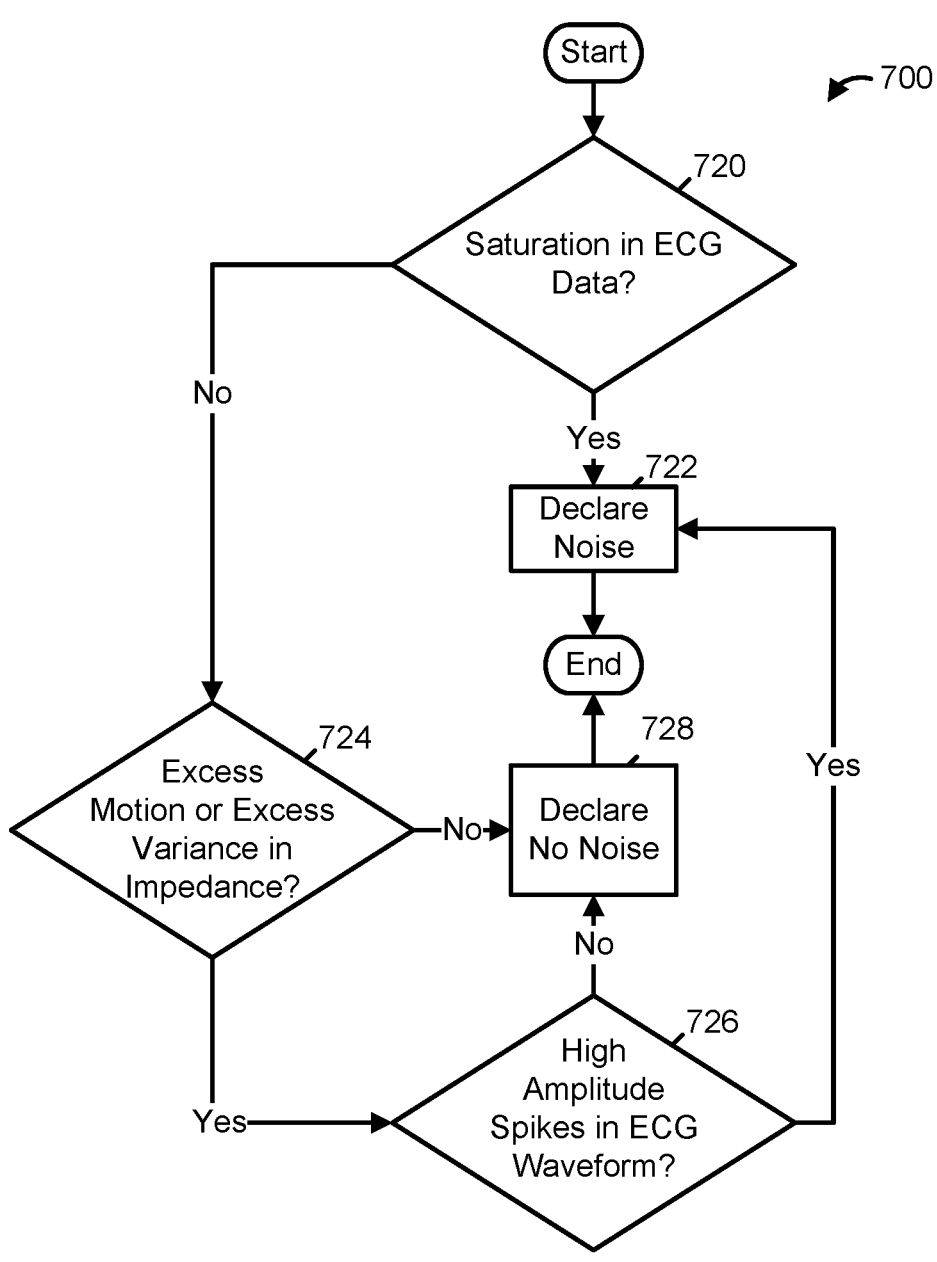
FIG. 7 is a flow diagram illustrating a noise detection process in accordance with at least one example disclosed herein.

Turning now to FIG. 7, a noise detection process 700 is illustrated. As shown in FIG. 7, the noise detection process 700 starts with the medical device determining 720 whether ECG data included in a segment being analyzed for noise includes saturation (i.e., amplitude values that indicate an ECG waveform that extends beyond the dynamic range of the ECG sensor). As dynamic range varies with sensor make and model, so do the amplitude values that indicate saturation. Where the medical device determines 720 that the ECG data includes saturation, the medical device declares 722 the segment to include excessive noise, and the process 700 ends. Where the medical device determines 720 that the ECG data does not include saturation, the medical device proceeds to operation 724.

Continuing with the process 700, the medical device determines 724 whether the motion data or the impedance data included within the segment have excessive variability. For instance, the medical device can calculate the standard deviation of the motion data and the impedance data and can determine that either is excessive where the standard deviation exceeds a corresponding deviation threshold. Examples of these deviation thresholds are described above with reference to FIGS. 4A and 4B. Where the medical device determines that neither the motion data nor the impedance data has a standard deviation that exceeds its corresponding deviation threshold, the medical device declares 728 the segment not to include excessive noise, and the process 700 ends. Where the medical device determines that the motion data and/or the impedance data has a standard deviation that exceeds its corresponding deviation threshold, the medical device proceeds to operation 726.

Continuing with the process 700, the medical device determines 726 whether the ECG data includes one or more high amplitude spikes (e.g., one or more amplitude values that transgress an amplitude threshold). Examples of these deviation thresholds are described above with reference to FIGS. 4A and 4B. Where the medical device determines that the ECG data includes one or more high amplitude spikes, the medical device declares 722 the segment to include excessive noise, and the process 700 ends. Where the medical device determines that the ECG data does not include one or more high amplitude spikes, the medical device declares 728 the segment not to include excessive noise, and the process 700 ends.

Returning to the process 600 as illustrated in FIG. 6B, the medical device determines 648 whether shock/no-shock guidance associated with the identified segment agrees with preliminary shock/no-shock guidance associated with clauses that generated votes for 1-second reconfirmation. For instance, in some examples, to determine 648 whether the shock/no-shock guidance associated with the identified segment agrees with the preliminary shock/no-shock guidance, the medical device compares features of the identified segment to clauses associated with the preliminary shock/no-shock guidance. In these examples, the medical device determines 648 that the shock/no-shock guidance associated with the identified segment agrees with the preliminary shock/no-shock guidance where the features of the identified segment meet one or more of the clauses. Where the medical device determines 648 that the shock/no-shock guidance does not agree with the preliminary shock/no-shock guidance, the medical device proceeds to operation 652 as illustrated in FIG. 6C. Where the medical device determines 648 that the shock/no-shock guidance associated with the identified segment agrees with the preliminary shock/no-shock guidance, the medical device proceeds to operation 650.

Continuing with the process 600, the medical device renders 650 the shock/no-shock guidance. For instance, the medical device can prompt the healthcare provider, via a user interface, to administer another cycle of CPR or administer transcutaneous electrotherapy. Subsequent to rendering 650 of the shock/no-shock guidance, the process 600 ends.

Continuing with the process 600 with reference to FIG. 6C, the medical device identifies 652 a second one second segment of sensor data (e.g., the segment 310 of FIG. 3C) generated from sensor signals acquired during a pause in CPR. The identified segment of sensor data can include, for example, ECG data, motion data, and/or impedance data. The medical device next extracts 654 features from the identified segment. These features can include, for example, any of the features of the segments 202-208 described above with reference to FIG. 2.

Continuing with the process 600, the medical device determines 656 whether the identified segment includes excessive noise. For instance, in some examples, the medical device can execute a noise detection process (e.g. the noise detection process 700 of FIG. 7) to determine 656 whether the identified segment is contaminated with excessive noise. In these examples, the medical device determines 656 that the identified segment includes excessive noise where the noise detection process declares the same within the identified segment. Where the medical device determines 656 that the identified segment does not include excessive noise, the medical device proceeds to operation 658. Where the medical device determines 656 that the identified segment includes excessive noise, the medical device proceeds to operation 662 as illustrated in FIG. 6D.

Continuing with the process 600, the medical device determines 658 whether shock/no-shock guidance associated with the identified segment agrees with preliminary shock/no-shock guidance associated with clauses that generated votes for 2-second reconfirmation. For instance, in some examples, to determine 658 whether the shock/no-shock guidance associated with the identified segment agrees with the preliminary shock/no-shock guidance, the medical device compares features of the identified segment to clauses associated with the preliminary shock/no-shock guidance. In these examples, the medical device determines 658 that the shock/no-shock guidance associated with the identified segment agrees with the preliminary shock/no-shock guidance where the features of the identified segment meet one or more of the clauses. Where the medical device determines 658 that the shock/no-shock guidance does not agree with the preliminary shock/no-shock guidance, the medical device proceeds to operation 662 as illustrated in FIG. 6D. Where the medical device determines 658 that the shock/no-shock guidance associated with the identified segment agrees with the preliminary shock/no-shock guidance, the medical device proceeds to operation 660.

Continuing with the process 600, the medical device renders 660 the shock/no-shock guidance. For instance, the medical device can prompt the healthcare provider, via a user interface, to administer another cycle of CPR or administer transcutaneous electrotherapy. Subsequent to rendering 660 of the shock/no-shock guidance, the process 600 ends.

Figure 6D:
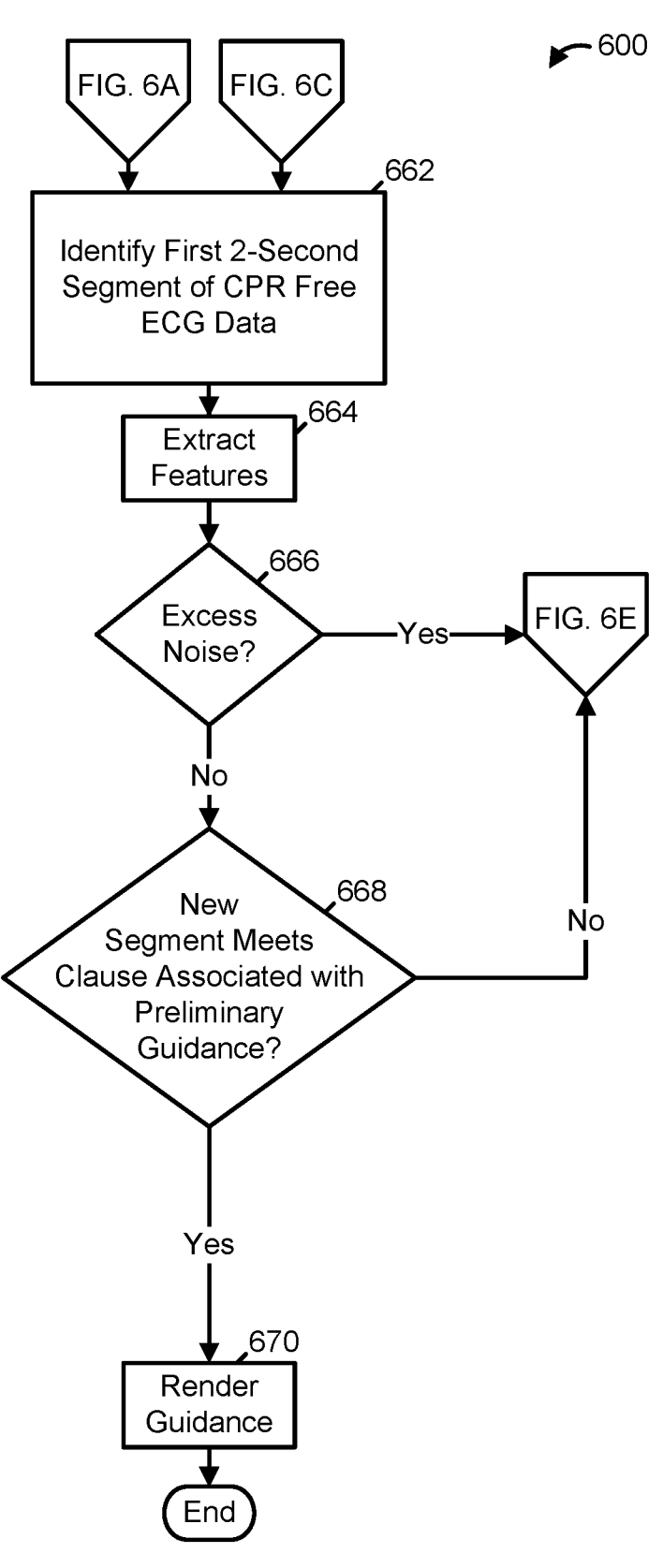
FIG. 6D is a flow diagram illustrating other select portions of a mixed-segment analysis process in accordance with at least one example disclosed herein.

Continuing with the process 600 with reference to FIG. 6D, the medical device identifies 662 a first two second segment of sensor data (e.g., the segment 312 of FIG. 3D) generated from sensor signals acquired during a pause in CPR. The identified segment of sensor data can include, for example, ECG data, motion data, and/or impedance data. The medical device next extracts 664 features from the identified segment. These features can include, for example, any of the features of the segments 202-208 described above with reference to FIG. 2.

Continuing with the process 600, the medical device determines 666 whether the identified segment includes excessive noise. For instance, in some examples, the medical device can execute a noise detection process (e.g. the noise detection process 700 of FIG. 7) to determine 666 whether the identified segment is contaminated with excessive noise. In these examples, the medical device determines 666 that the identified segment includes excessive noise where the noise detection process declares the same within the identified segment. Where the medical device determines 666 that the identified segment does not include excessive noise, the medical device proceeds to operation 668. Where the medical device determines 666 that the identified segment includes excessive noise, the medical device proceeds to operation 672 as illustrated in FIG. 6E.

Continuing with the process 600 as illustrated in FIG. 6D, the medical device determines 668 whether shock/no-shock guidance associated with the identified segment agrees with preliminary shock/no-shock guidance associated with clauses that generated votes for 2-second reconfirmation. For instance, in some examples, to determine 668 whether the shock/no-shock guidance associated with the identified segment agrees with the preliminary shock/no-shock guidance, the medical device compares features of the identified segment to clauses associated with the preliminary shock/no-shock guidance. In these examples, the medical device determines 668 that the shock/no-shock guidance associated with the identified segment agrees with the preliminary shock/no-shock guidance where the features of the identified segment meet one or more of the clauses. Where the medical device determines 668 that the shock/no-shock guidance does not agree with the preliminary shock/no-shock guidance, the medical device proceeds to operation 672 as illustrated in FIG. 6E. Where the medical device determines 668 that the shock/no-shock guidance associated with the identified segment agrees with the preliminary shock/no-shock guidance, the medical device proceeds to operation 670.

Continuing with the process 600, the medical device renders 670 the shock/no-shock guidance. For instance, the medical device can prompt the healthcare provider, via a user interface, to administer another cycle of CPR or administer transcutaneous electrotherapy. Subsequent to rendering 670 of the shock/no-shock guidance, the process 600 ends.

Figure 6E:
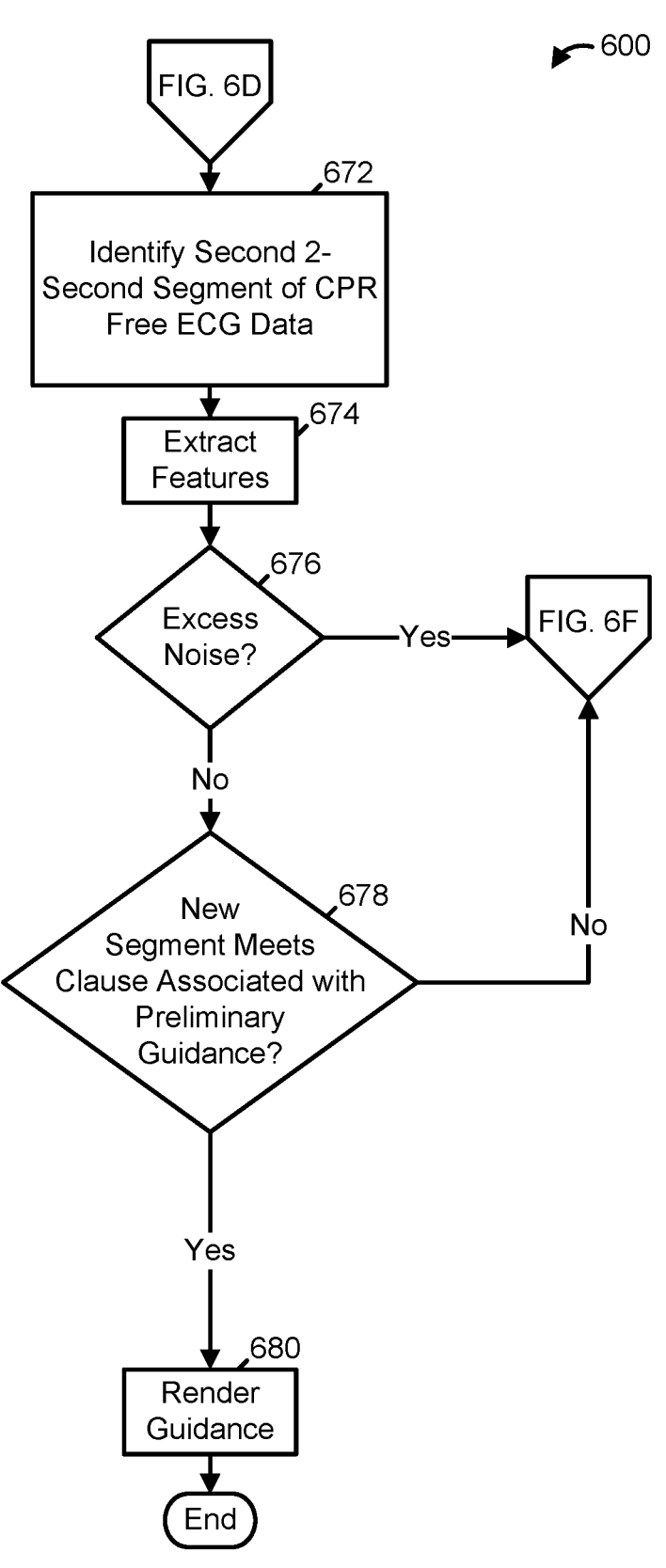
FIG. 6E is a flow diagram illustrating other select portions of a mixed-segment analysis process in accordance with at least one example disclosed herein.

Continuing with the process 600 with reference to FIG. 6E, the medical device identifies 672 a second two second segment of sensor data (e.g., the segment 314 of FIG. 3E) generated from sensor signals acquired during a pause in CPR. The identified segment of sensor data can include, for example, ECG data, motion data, and/or impedance data. The medical device next extracts 674 features from the identified segment. These features can include, for example, any of the features of the segments 202-208 described above with reference to FIG. 2.

Continuing with the process 600, the medical device determines 676 whether the identified segment includes excessive noise. For instance, in some examples, the medical device can execute a noise detection process (e.g. the noise detection process 700 of FIG. 7) to determine 676 whether the identified segment is contaminated with excessive noise. In these examples, the medical device determines 676 that the identified segment includes excessive noise where the noise detection process declares the same within the identified segment. Where the medical device determines 676 that the identified segment does not include excessive noise, the medical device proceeds to operation 678. Where the medical device determines 676 that the identified segment includes excessive noise, the medical device proceeds to operation 682 as illustrated in FIG. 6F.

Continuing with the process 600, the medical device determines 678 whether shock/no-shock guidance associated with the identified segment agrees with preliminary shock/no-shock guidance associated with clauses that generated votes for 2-second reconfirmation. For instance, in some examples, to determine 678 whether the shock/no-shock guidance associated with the identified segment agrees with the preliminary shock/no-shock guidance, the medical device compares features of the identified segment to clauses associated with the preliminary shock/no-shock guidance. In these examples, the medical device determines 678 that the shock/no-shock guidance associated with the identified segment agrees with the preliminary shock/no-shock guidance where the features of the identified segment meet one or more of the clauses. Where the medical device determines 678 that the shock/no-shock guidance does not agree with the preliminary shock/no-shock guidance, the medical device proceeds to operation 682 as illustrated in FIG. 6F. Where the medical device determines 678 that the shock/no-shock guidance associated with the identified segment agrees with the preliminary shock/no-shock guidance, the medical device proceeds to operation 680.

Continuing with the process 600, the medical device renders 680 the shock/no-shock guidance. For instance, the medical device can prompt the healthcare provider, via a user interface, to administer another cycle of CPR or administer transcutaneous electrotherapy. Subsequent to rendering 680 of the shock/no-shock guidance, the process 600 ends.

Figure 6F:
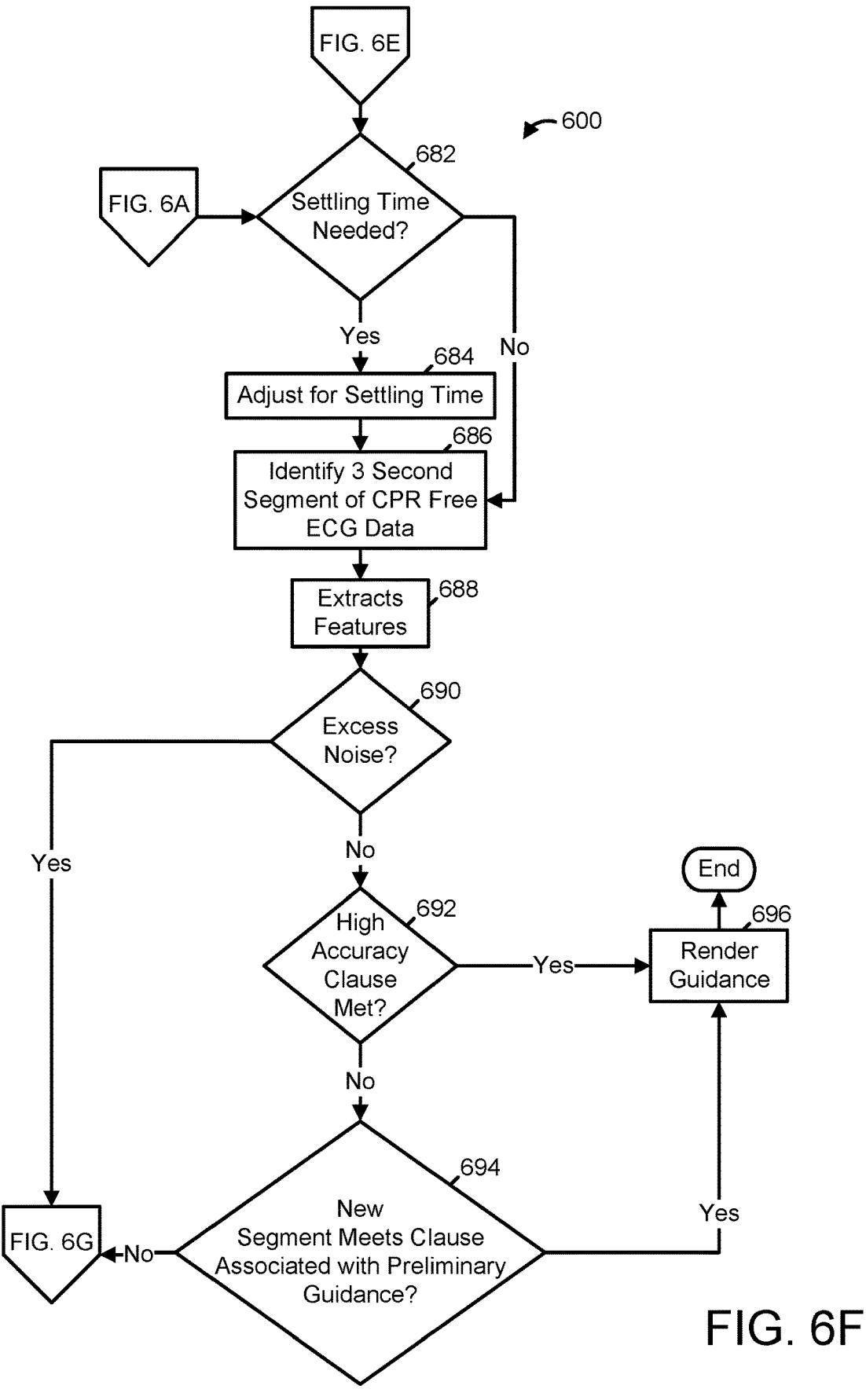
FIG. 6F is a flow diagram illustrating other select portions of a mixed-segment analysis process in accordance with at least one example disclosed herein.

Continuing with the process 600 with reference to FIG. 6F, the medical device determines 682 whether the quality of signals acquired during the CPR interval indicate that the quality of signals to be acquired during a pause in CPR would likely benefit from settling time. For instance, in some examples, the medical device compares the total number of votes for provision of settling time generated by the operation 682 to a settling time vote threshold. In these examples, the medical device determines 682 that the quality of signals to be acquired during a pause in CPR would likely benefit from settling time where the total number of votes exceeds the settling time vote threshold. In some examples, the settling time vote threshold is set to 1 vote. In some examples, the settling time vote threshold is set to a number that represents a majority of the segments identified 608. Other settling time vote thresholds are possible. Where the medical device determines 682 that settling time is to be provided, the medical device adjusts 684 (e.g., delays for a duration of settling time) the period of time for the three second segment to be identified in operation 686. In some examples, this settling time ranges from 1 to 2 seconds. Where the medical device determines 682 that settling time is not to be provided, the medical device proceeds to operation 686. It should be noted that, in some examples of the process 600, the operations 682 and 684 execute as a preface to 1-second reconfirmation and/or 2-second reconfirmation in addition to 3-second reconfirmation.

Continuing with the process 600, the medical device identifies 686 a three second segment of sensor data (e.g., the segment 316 of FIG. 3F or the segment 318 of FIG. 3G) generated from sensor signals acquired during a pause in CPR. The identified segment of sensor data can include, for example, ECG data, motion data, and/or impedance data. The medical device next extracts 688 features from the identified segment. These features can include, for example, any of the features of the segments 202-208 described above with reference to FIG. 2.

Figure 6G:
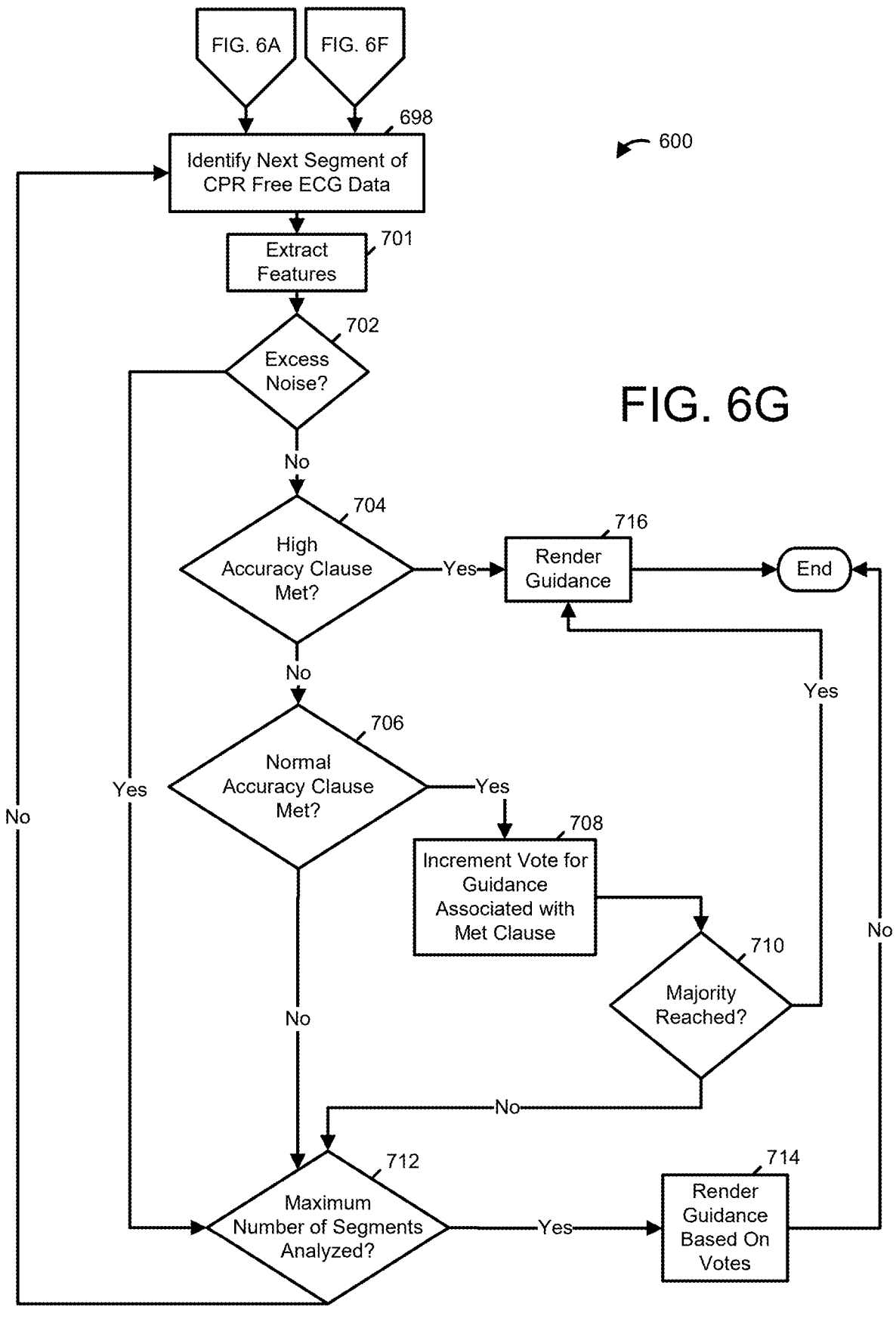
FIG. 6G is a flow diagram illustrating other select portions of a mixed-segment analysis process in accordance with at least one example disclosed herein.

Continuing with the process 600, the medical device determines 690 whether the identified segment includes excessive noise. For instance, in some examples, the medical device can execute a noise detection process (e.g. the noise detection process 700 of FIG. 7) to determine 690 whether the identified segment is contaminated with excessive noise. In these examples, the medical device determines 690 that the identified segment includes excessive noise where the noise detection process declares the same within the identified segment. Where the medical device determines 690 that the identified segment does not include excessive noise, the medical device proceeds to operation 692. Where the medical device determines 690 that the identified segment includes excessive noise, the medical device proceeds to operation 698 as illustrated in FIG. 6G.

Continuing with the process 600, the medical device determines 692 whether the identified segment meets a high accuracy clause for 3-second reconfirmation. For instance, in some examples, the medical device determines 692 that the identified segment meets the high accuracy clause by comparing the features of the identified segment to any 3-second high accuracy clause as described above with reference to FIG. 2. In these examples, the medical device determines 692 that the identified segment meets the high accuracy clause where the features satisfy the high accuracy clause. Where the medical device determines 692 that the identified segment does not meet the high accuracy clause, the medical device proceeds to operation 694. Where the medical device determines 692 that the identified segment meets the high accuracy clause, the medical device records shock/no-shock guidance associated with the high accuracy clause as final shock/no-shock guidance and proceeds to operation 696.

Continuing with the process 600, the medical device determines 694 whether shock/no-shock guidance associated with the identified segment agrees with preliminary shock/no-shock guidance associated with clauses that generated votes for 3-second reconfirmation. For instance, in some examples, to determine 694 whether the shock/no-shock guidance associated with the identified segment agrees with the preliminary shock/no-shock guidance, the medical device compares features of the identified segment to clauses associated with the preliminary shock/no-shock guidance. In these examples, the medical device determines 694 that the shock/no-shock guidance associated with the identified segment agrees with the preliminary shock/no-shock guidance where the features of the identified segment meet one or more of the clauses. Where the medical device determines 694 that the shock/no-shock guidance does not agree with the preliminary shock/no-shock guidance, the medical device proceeds to operation 698 as illustrated in FIG. 6G. Where the medical device determines 694 that the shock/no-shock guidance associated with the identified segment agrees with the preliminary shock/no-shock guidance, the medical device records the agreed to shock/no-shock guidance as final shock/no-shock guidance and proceeds to operation 696.

Continuing with the process 600, the medical device renders 696 the final shock/no-shock guidance. For instance, the medical device can prompt the healthcare provider, via a user interface, to administer another cycle of CPR or administer transcutaneous electrotherapy. Subsequent to rendering 696 of the shock/no-shock guidance, the process 600 ends.

Continuing with the process 600 with reference to FIG. 6G, the medical device identifies 698 a segment of sensor data (e.g., any of the segments 320-324 of FIG. 3H) generated from sensor signals acquired during a pause in CPR. The identified segment of sensor data can include, for example, ECG data, motion data, and/or impedance data. The medical device next extracts 701 features from the identified segment. These features can include, for example, any of the features of the segments 202-208 described above with reference to FIG. 2.

Continuing with the process 600, the medical device determines 702 whether the identified segment includes excessive noise. For instance, in some examples, the medical device can execute a noise detection process (e.g. the noise detection process 700 of FIG. 7) to determine 702 whether the identified segment is contaminated with excessive noise. In these examples, the medical device determines 702 that the identified segment includes excessive noise where the noise detection process declares the same within the identified segment. Where the medical device determines 702 that the identified segment does not include excessive noise, the medical device proceeds to operation 704. Where the medical device determines 702 that the identified segment includes excessive noise, the medical device proceeds to operation 712.

Continuing with the process 600, the medical device determines 704 whether the identified segment meets a high accuracy clause. For instance, in some examples, the medical device determines 704 whether the identified segment meets the high accuracy clause by comparing the features of the identified segment to any high accuracy clause as described above with reference to FIG. 2. In these examples, the medical device determines 704 that the identified segment meets the high accuracy clause where the features satisfy the high accuracy clause. Where the medical device determines 704 that identified segment does not meet the high accuracy clause, the medical device proceeds to operation 706. Where the medical device determines 704 that the identified segment meets the high accuracy clause, the medical device records shock/no-shock guidance associated with the high accuracy clause as final shock/no-shock guidance and proceeds to operation 716.

Continuing with the process 600, the medical device determines 706 whether the identified segment meets a normal accuracy clause. For instance, in some examples, the medical device determines 706 whether the identified segment meets the normal accuracy clause by comparing the features of the identified segment to any normal accuracy clause as described above with reference to FIG. 2. In these examples, the medical device determines 706 that the identified segment meets the normal accuracy clause where the features satisfy the normal accuracy clause. Where the medical device determines 706 that identified segment does not meet the normal accuracy clause, the medical device proceeds to operation 712. Where the medical device determines 706 that the identified segment meets the normal accuracy clause, the medical device records treatment records 708 a vote for shock/no-shock guidance associated with the normal accuracy clause.

Continuing with the process 600, the medical device determines 710 whether a majority of the total number of votes possible has been reached. For instance, in some examples, to determine whether a majority has been reached, the medical device compares a threshold value to the number of votes already recorded for each possible shock/no-shock guidance. In these examples, the threshold value represents a majority of the total number of votes possible via execution of the operation 708. For instance, where the number of segments that can be identified via the operation 698 is limited to 15 due to time constraints, the threshold value is set to 8. Further, in these examples, the medical device determines 710 that a majority is reached where the number of votes already recorded for a possible shock/no-shock guidance exceeds the threshold value. Where the medical device determines 710 that a majority is reached, the medical device records the shock/no-shock guidance associated with the majority as finalized shock/no-shock guidance and proceeds to the operation 716. Where the medical device determines that a majority is not reached, the medical device proceeds to the operation 712. It should be noted that in some examples, the medical device modifies (e.g., decreases) the threshold value used to determine a majority by the number of segments identified as being contaminated with excessive noise in the operation 702.

Continuing with the process 600, the medical device determines 712 whether the number of segments identified in the operation 698 exceeds a maximum number of segments. For instance, in some examples, the medical device determines 712 whether the number of segments exceeds the maximum number by comparing the number of segments to a threshold value. This threshold value may vary between 9 and 20, in various examples. In certain examples, the medical device determines 712 that the number of segments exceeds the maximum number where the number of segments exceeds the threshold value. Where the medical device determines 712 that the number of segments does not exceed the maximum number, the medical device returns to identify 698 the next overlapping segment. Where the medical device determines 712 that the number of segments exceeds the maximum number, the medical device proceeds to operation 714.

Continuing with the process 600, the medical device renders 714 shock/no-shock guidance based on the votes recorded by the operation 708. For instance, the medical device can calculate a number of votes recorded for each type of shock/no-shock guidance (e.g., shock, no-shock, noise) that received at least one vote and render shock/no-shock guidance based on the type that received the most votes. For instance, where shock guidance receives 7 of 15 votes, no-shock guidance receives 6 of the 15 votes, and noise receives 2 of the 15 votes, the medical device may render shock guidance within the operation 714. To render the shock/no-shock guidance, the medical device can prompt the healthcare provider, via a user interface, to administer another cycle of CPR rather than allow the pause in CPR to continue. Subsequent to rendering 714 of the shock/no-shock guidance, the process 600 ends.

Continuing with the process 600, the medical device renders 716 finalized shock/no-shock guidance. For instance, the medical device can prompt the healthcare provider, via a user interface, to administer another cycle of CPR or administer transcutaneous electrotherapy. Subsequent to rendering 716 of the shock/no-shock guidance, the process 600 ends.

Turning now to FIGS. 8A-8F, a variety of practical transitions from CPR to analysis intervals is shown. These scenarios serve to further illustrate the function of the operations 506 and 514 of FIG. 5 and/or the operations 608 and 632 of FIG. 6A, in some examples.

Figure 8A:
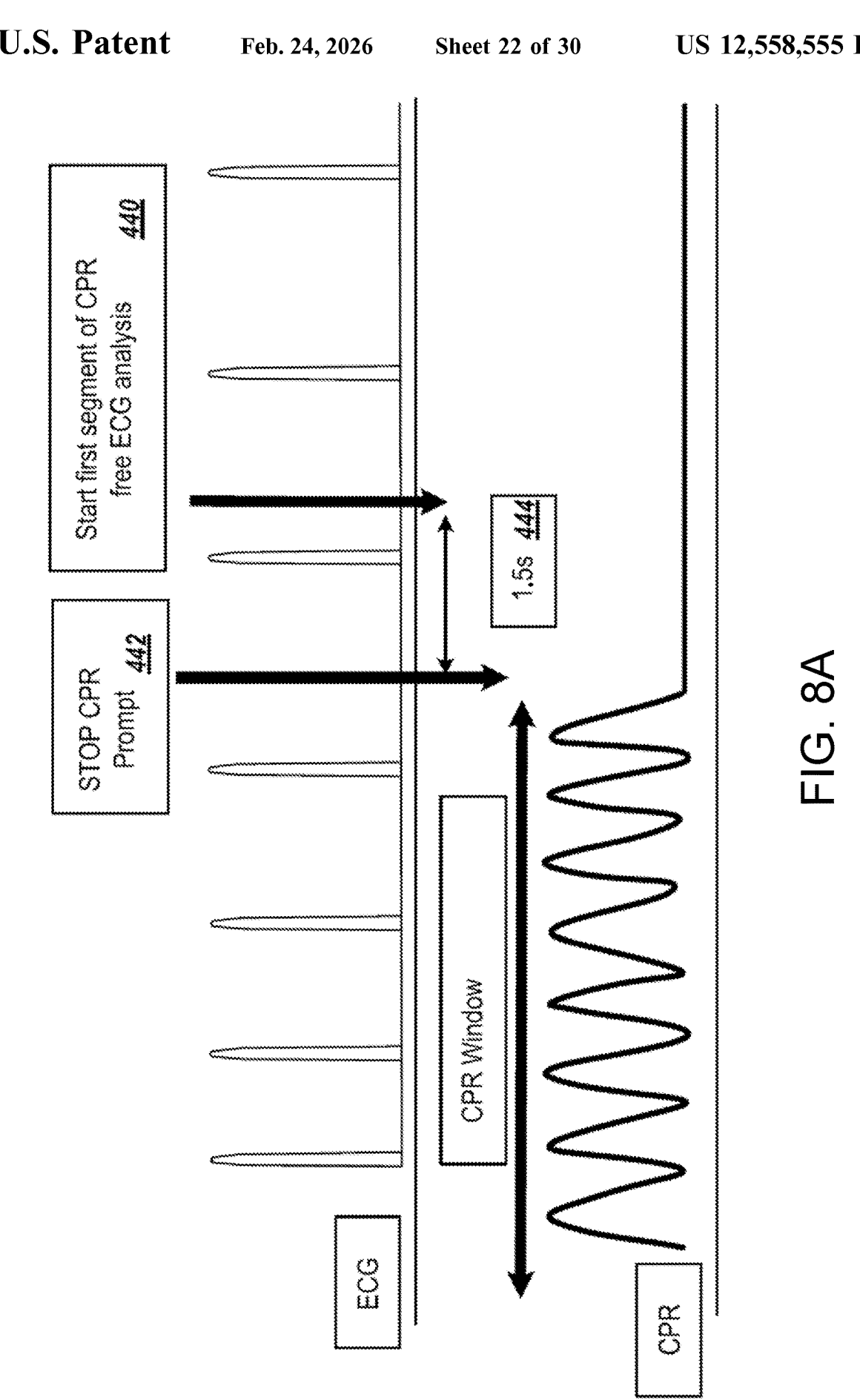
FIG. 8A is a graphical diagram illustrating an ECG waveform in relation to CPR treatments in accordance with at least one example disclosed herein.

As shown in FIG. 8A, a medical device determines that chest compressions should cease (bringing a CPR interval to an end) in favor of analyzing 440 ECG data to determine whether a shock should be applied (beginning an analysis interval). In this situation, an instructive prompt 442 is issued for the healthcare provider to stop CPR and be hands-free from the patient. In various implementations, the medical device may optionally pause for a short period of time before analysis of ECG data generated from signals acquired during a pause in CPR. This short pause 444 may be preferable in some cases to ensure that the ECG signal is substantially free of artifact, present or residual, having arisen from the chest compressions. While the example of FIG. 8A shows the short pause time before analysis of ECG data generated from signals acquired during a pause in CPR to be approximately 1.5 seconds, any appropriate pause time may be employed, such as less than 2 seconds, less than 1.5 seconds, less than 1 second, less than 0.5 seconds, less than 0.2 seconds, less than 0.1 second, etc. In some implementations, while not shown in this figure, upon detection of an interruption in chest compressions, the analysis of ECG data generated from signals acquired during a pause in CPR may be immediately employed.

Figure 8B:
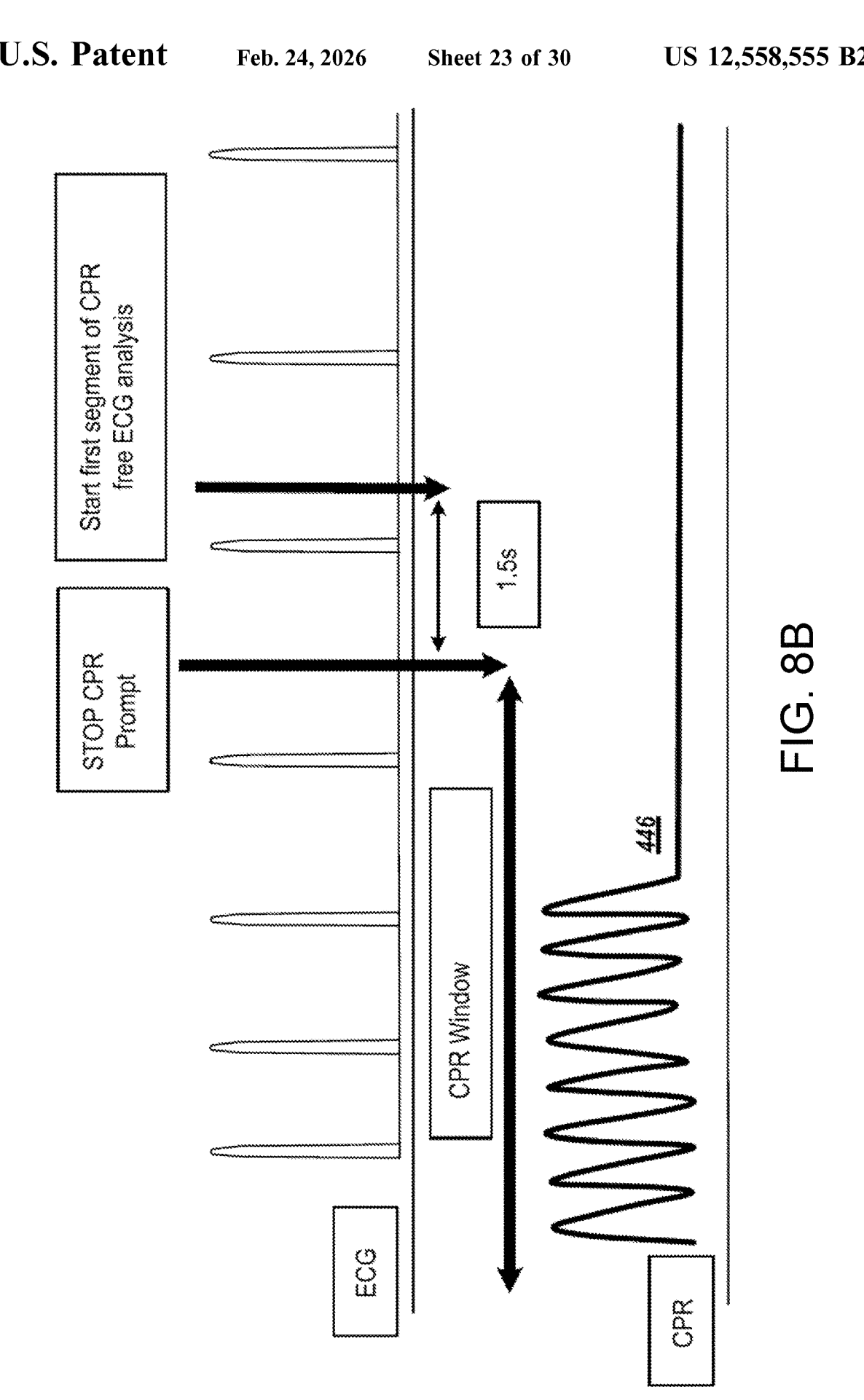
FIG. 8B is a graphical diagram illustrating another ECG waveform in relation to CPR treatments in accordance with at least one example disclosed herein.

FIG. 8B depicts an implementation where chest compressions are stopped 446 even prior to when the instructive prompt is provided by the medical device. While it is not advisable to cease chest compressions prematurely, for various reasons, it is common for healthcare providers to do so due to inexperience, improper training, and/or fatigue. In such a case, while not shown in the figure, the medical device may prompt the healthcare provider to continue chest compressions or display an idle timer that shows how long the healthcare provider has ceased compressions, up until the time when the medical device determines that chest compressions should be interrupted for analysis of ECG data generated from signals acquired during a pause in CPR to commence. The implementation of FIG. 8B still pauses for a short period of time after the prompt to stop CPR, however, it can be appreciated that such a pause is not required. For example, when an interruption in chest compressions is detected, the medical device may automatically and/or immediately begin analysis of ECG data generated from signals acquired during a pause in CPR without any such pause.

Figure 8C:
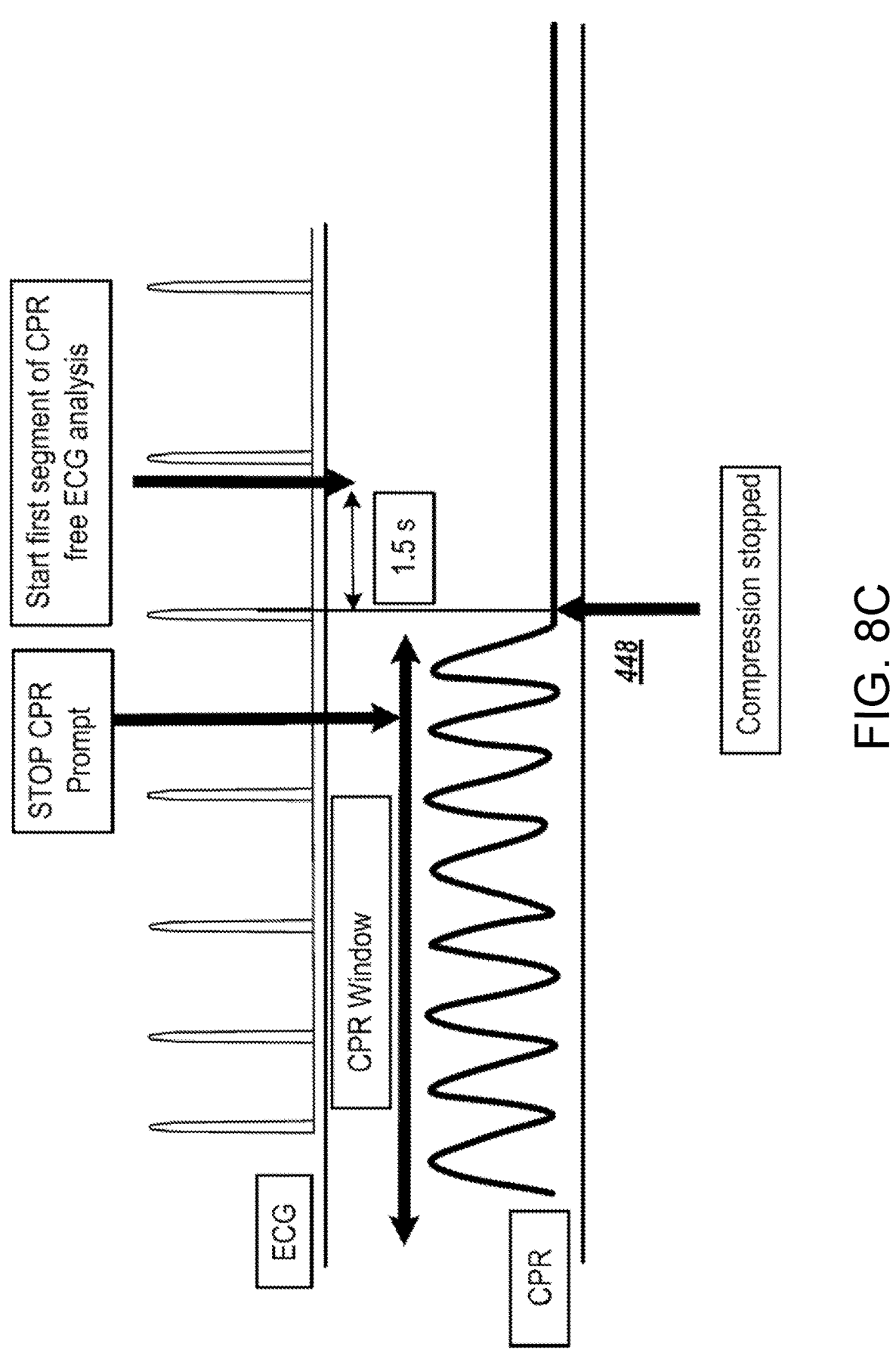
FIG. 8C is a graphical diagram illustrating another ECG waveform in relation to CPR treatments in accordance with at least one example disclosed herein.

FIG. 8C shows an implementation where chest compressions are continued for a short time 448 (e.g., 1-2 seconds) beyond the time in which the medical device issues the instructive prompt to stop CPR. In this case, the medical device tracks the chest compressions up until the time when compressions are ceased, optionally pauses for a short period of time (e.g., approximately 1.5 seconds), and then begins analysis of ECG data generated from signals acquired during a pause in CPR in accordance with the present disclosure.

Figure 8D:
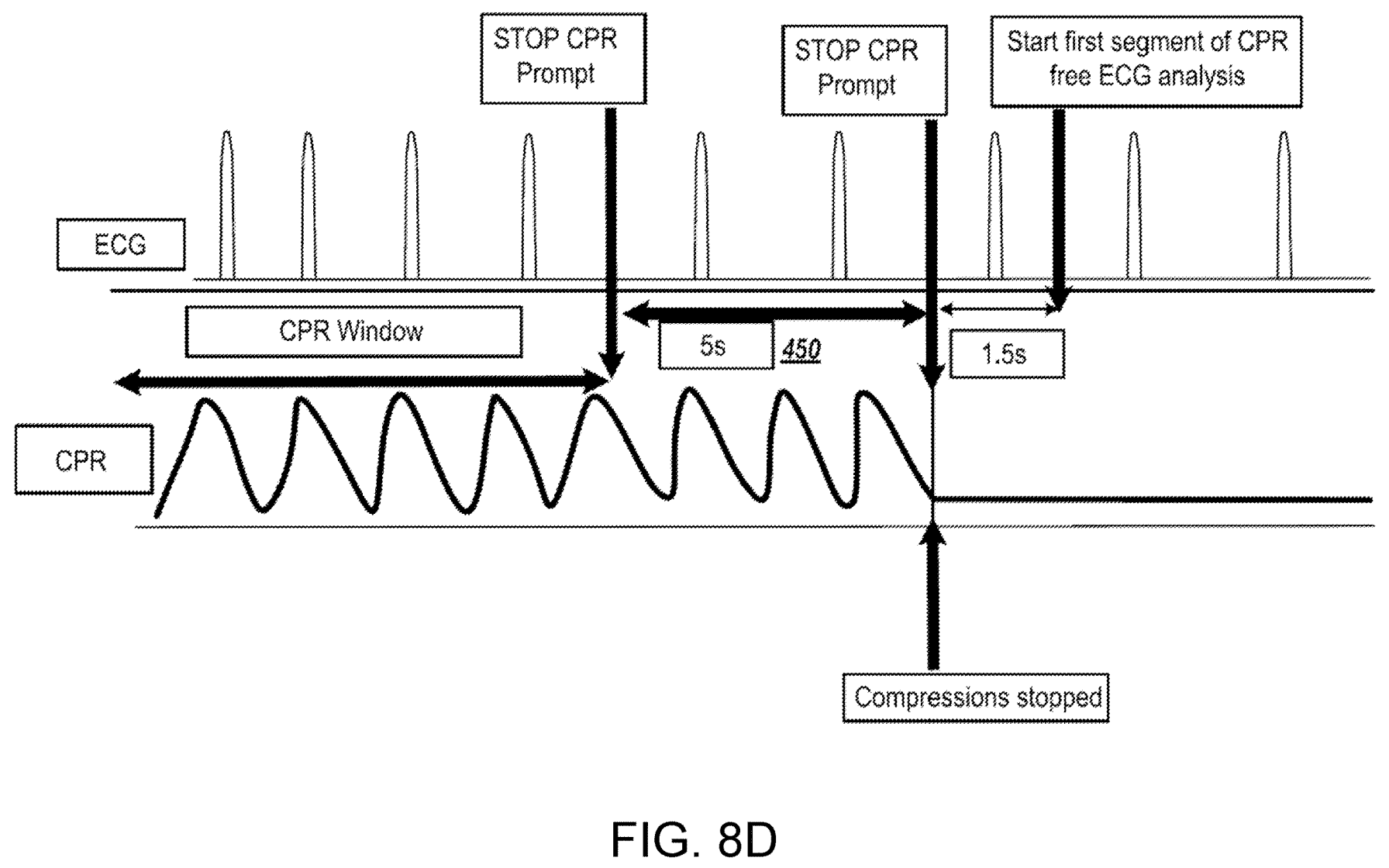

FIG. 8D depicts another implementation of an instance where chest compressions are continued for a longer period 450 than that shown in FIG. 8C. Here, the medical device continues to track the chest compressions, and after a sufficiently long time period, the medical device then issues a subsequent instructive prompt reminding the healthcare provider to stop CPR. It can be appreciated that the subsequent instructive prompt can be provided at any suitable time, which may be predetermined by an appropriate time interval. In this particular case, the medical device issues the subsequent prompt after approximately 3 seconds which, in some cases, may be similar to an initial segment of sensor data. As further shown, when chest compressions are interrupted, the medical device optionally pauses for a short time (e.g., approximately 1.5 seconds), and then commences analysis of ECG data generated from signals acquired during a pause in CPR.

Figure 8E:
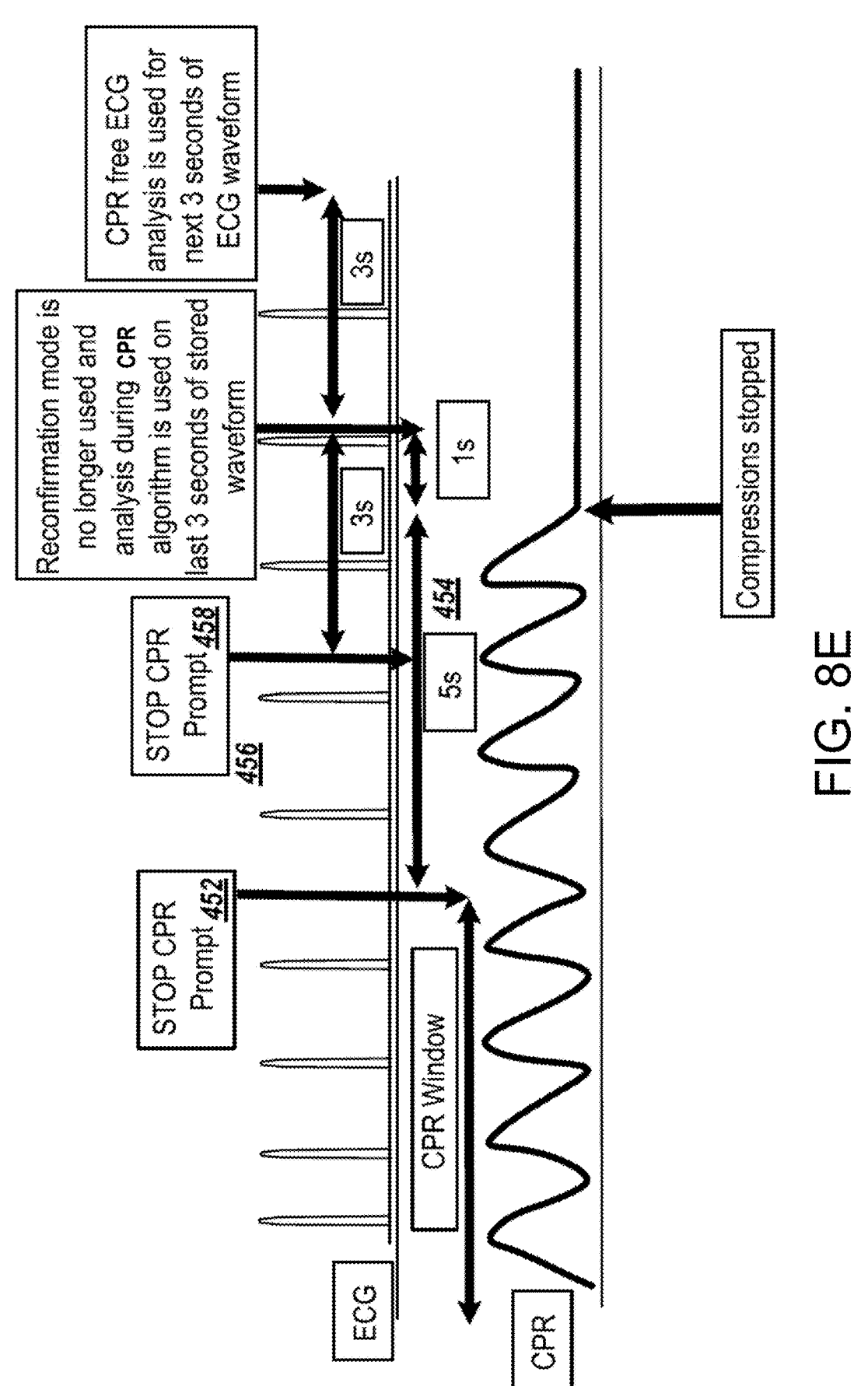
FIG. 8E is a graphical diagram illustrating another ECG waveform in relation to CPR treatments in accordance with at least one example disclosed herein.

FIG. 8E shows an implementation where chest compressions are continued for an even longer period of time 454. In this example, the medical device issues the first prompt 452 instructing the user to stop chest compressions, and then after a sufficiently long time interval 456 (e.g., approximately 3 seconds), the medical device then issues a subsequent instructive prompt 458 reminding the healthcare provider to stop CPR compressions. However, here, the medical device continues to sense chest compressions after the subsequent instructive prompt, resulting in further delay in the analysis of ECG data generated from signals acquired during a pause in CPR. In various implementations, the ECG signal is tracked according to short time segments (e.g., approximately 3 seconds), and once the medical device identifies an interruption in chest compressions, the analysis of ECG data generated from signals acquired during a pause in CPR begins at the start of the next time segment. As shown more specifically in FIG. 8E, the medical device does not detect an interruption in chest compressions until approximately 2 seconds after the most recent instructive prompt to stop CPR compressions. The analysis of ECG data generated from signals acquired during a pause in CPR then begins after the approximately 1 second that remains in the 3 second interval elapses. Though, for certain implementations, after the subsequent instructive prompt, as soon as an interruption in chest compressions has been determined, the medical device may immediately begin analysis of ECG data generated from signals acquired during a pause in CPR, without the optional pause.

Figure 8F:
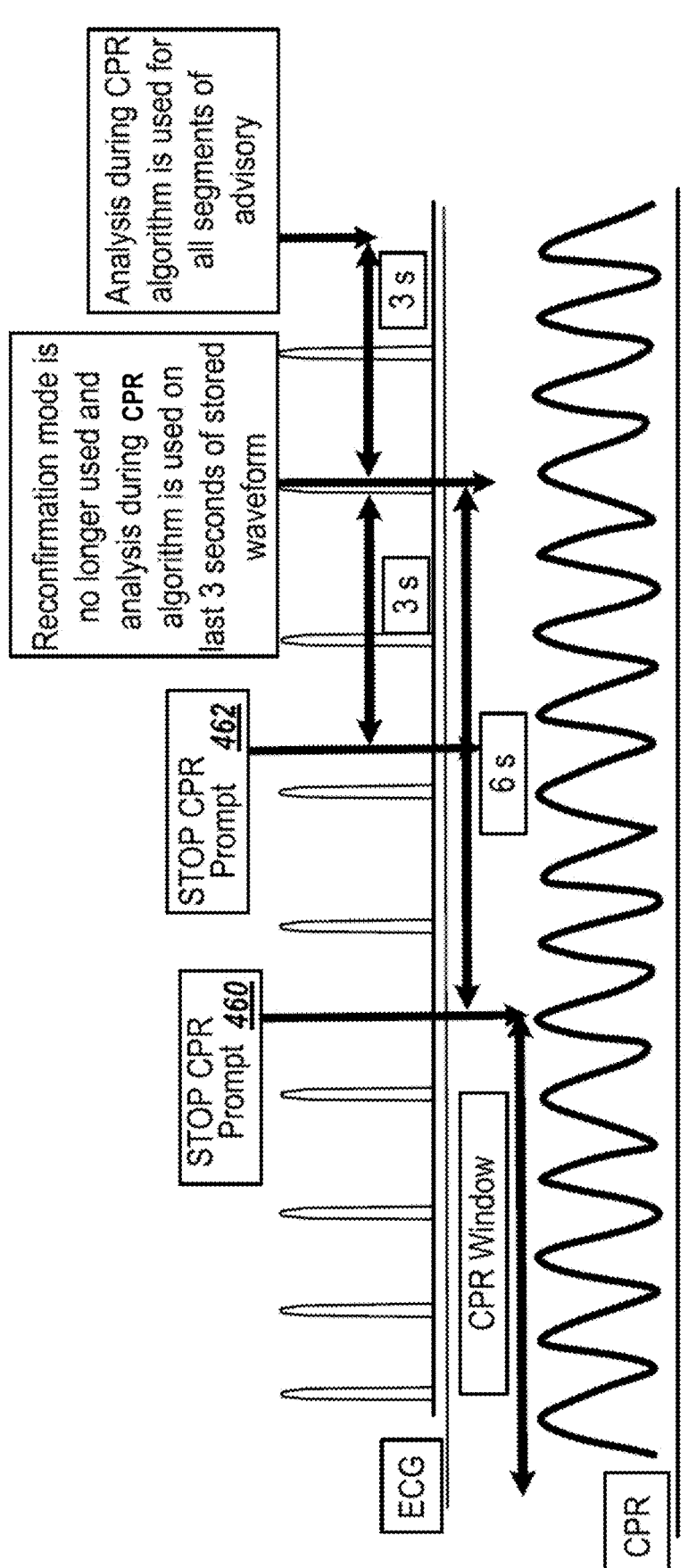
FIG. 8F is a graphical diagram illustrating another ECG waveform in relation to CPR treatments in accordance with at least one example disclosed herein.

FIG. 8F depicts another illustrative implementation where no interruption in CPR chest compressions is detected, despite multiple instructive prompts 460, 462 to stop chest compressions. In such a case, because chest compressions remain uninterrupted, the analysis of ECG data generated from signals acquired during a pause in CPR is unable to be used. In this case, the analysis of ECG data generated from signals acquired during active administration of CPR (which accounts for chest compression artifacts) is applied throughout the time in which chest compressions are administered.

Figure 9:
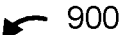
FIG. 9 is a histogram illustrating time utilized for medical devices to output shock/no-shock guidance from mixed-segment analysis of sensor data in accordance with at least one example disclosed herein.
Figure 9:
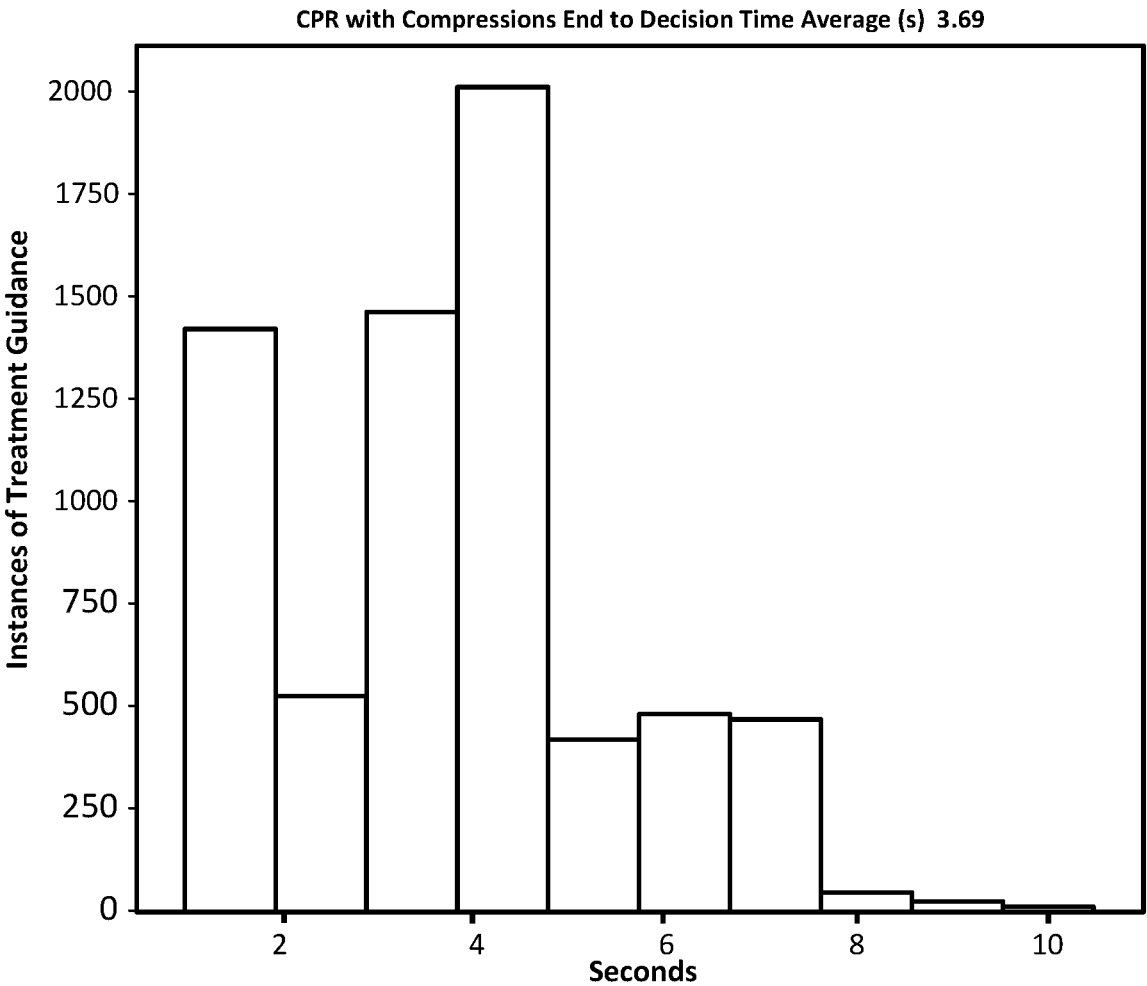

Testing of mixed-segment analysis processes, such as the process 600, shows a marked improvement over other CPR guidance processes with regard to the time utilized to produce accurate shock/no-shock guidance. One series of tests utilized a corpus of sensor data gathered from over 6,000 cycles of CPR administered to the patients. The corpus included ECG data captured during each cycle of CPR. In this series of tests, each of the patient encounters in the corpus was analyzed by a mixed-segment analysis process as described herein. FIG. 9 illustrates results of this series of tests in the form of a histogram 900.

As shown in the histogram 900, in approximately 20% of the CPR cycles analyzed, the mixed-segment process presented guidance within approximately 2 seconds of an initiation of a pause in CPR. In approximately 30% of the CPR cycles analyzed, the mixed-segment process presented guidance within approximately 3 seconds of an initiation of a pause in CPR. In approximately 50% of the CPR cycles analyzed, the mixed-segment process presented guidance within approximately 4 seconds of an initiation of a pause in CPR. In approximately 80% of the CPR cycles analyzed, the mixed-segment process presented guidance within approximately 5 seconds of an initiation of a pause in CPR. On average, the mixed-segment process presented shock/no-shock guidance within 3.69 seconds of an initiation of a pause in CPR.

Each of the processes disclosed herein each depicts one particular sequence of operations in a particular example. Some operations are optional and, as such, can be omitted in accord with one or more examples. Additionally, the order of operations can be altered, or other operations can be added, without departing from the scope of the apparatus and methods discussed herein. It should be noted that, in some examples, one or more of the processes disclosed herein are stored as sequences of instructions that are executable by a processor. In these examples, the sequences of instructions can be stored in one or more non-volatile/non-transitory data storage media accessible by the processor. The processor and/or data storage media can be a part of a medical device, as described herein.

Figure 10:
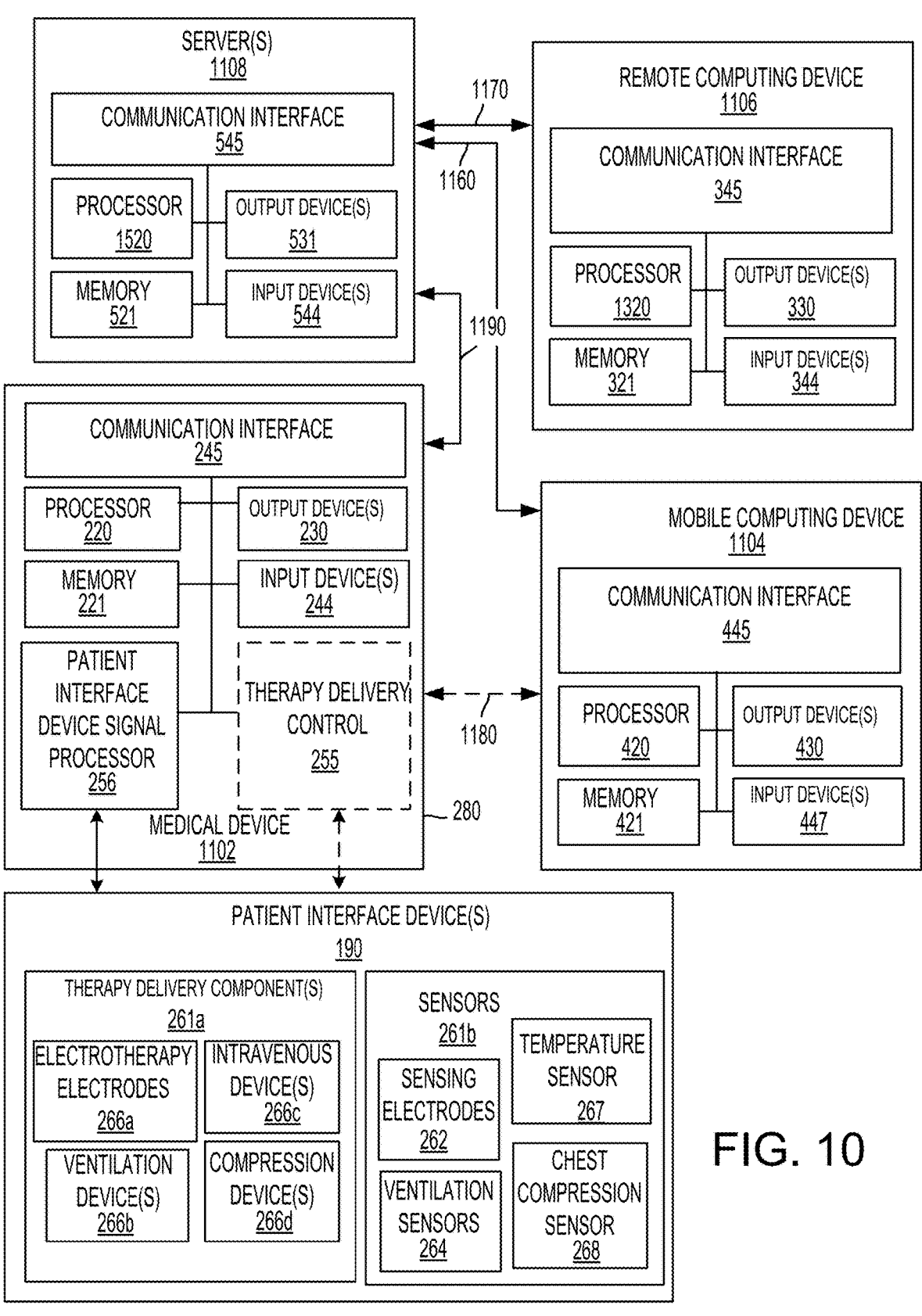
FIG. 10 is a schematic block diagram of examples of computing and medical device components in accordance with at least one example disclosed herein.

Referring now to FIG. 10, a block diagram of examples of computing and medical device components are shown schematically.

The medical device 1102 can include a processor 220, a memory 221, one or more output devices 230, one or more user input devices 244, and a communications interface 245. The communications interface 245 can include any of a variety of transmitters and/or receivers. For instance, in some examples, the communications interface 245 includes one or more of an NFC tag, an RFID tag, a barcode, and a QR code.

In various implementations, the medical device 1102 can be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 1102 can be an integrated therapy delivery/monitoring device within a single housing 280. The single housing 280 can surround, at least in part, a patient interface device signal processor 256 and/or a therapy delivery control module 255.

The patient interface device(s) 190 can include one or more therapy delivery component(s) 261a and/or one or more sensor device(s) 261b. The medical device 1102 can be configured to couple to the one or more therapy delivery component(s) 261a. In combination, the medical device 1102 and the one or more therapy delivery components can provide therapeutic treatment to a patient (e.g., the patient 104 of FIG. 1). In an implementation, the medical device 1102 can include or incorporate the therapy delivery component(s) 261a. The therapy delivery component(s) 261a are configured to deliver therapy to the patient and can be configured to couple to the patient. For example, the therapy delivery component(s) 261a can include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 1102 can include the one or more therapy delivery component(s) 261a and/or can be configured to couple to the one or more therapy delivery component(s) 261a in order to provide medical therapy to the patient. The therapy delivery component(s) 261a can be configured to couple to the patient. For example, a healthcare provider (e.g., the healthcare provider 102) may attach the electrodes to the patient, and the medical device 1102 (e.g., a defibrillator or defibrillator/patient monitor) may provide electrotherapy to the patient via the defibrillation electrodes. These examples are not limiting of the disclosure as other types of medical devices, therapy delivery components, sensors, and therapy are within the scope of the disclosure.

The medical device 1102 can be, for example, a therapeutic medical device capable of delivering a medical therapy. For example, the medical therapy can be electrical therapy (e.g. defibrillation, cardiac pacing, synchronized cardioversion, diaphragmatic or phrenic nerve stimulation) and the medical device 1102 can be a defibrillator, a defibrillator/monitor and/or another medical device configured to provide electrotherapy. As another example, the medical therapy can be chest compression therapy for treatment of cardiac arrest and the first medical device 1102 can be a mechanical chest compression device such as a belt-based chest compression device or a piston-based chest compression device. As other examples, the medical therapy can be ventilation therapy, therapeutic cooling or other temperature management, invasive hemodynamic support therapy (e.g. Extracorporeal Membrane Oxygenation (ECMO)), etc. and the medical device 1102 can be a device configured to provide a respective therapy. In an implementation, the medical device 1102 can be a combination of one or more of these examples. The therapeutic medical device can include patient monitoring capabilities via one or more sensors. These types of medical therapy and devices are examples only and not limiting of the disclosure.

The medical device 1102 can include, incorporate, and/or be configured to couple to the one or more sensor(s) 261b which can be configured to couple to the patient. The sensor(s) 261b are configured to provide signals indicative of sensor data to the medical device 1102. The sensor(s) 261b can be configured to couple to the patient. For example, the sensor(s) 261b can include cardiac sensing electrodes, a chest compression sensor, and/or ventilation sensors. The one or more sensors 261b can generate signals indicative of physiological parameters of the patient. For example, the physiological parameters can include one or more of at least one vital sign, an ECG, blood pressure, heart rate, pulse oxygen level, respiration rate, heart sounds, lung sounds, respiration sounds, tidal $CO_2$, saturation of muscle oxygen (SMO2), arterial oxygen saturation (SpO2), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. Additionally or alternatively, the one or more sensors 261b can generate signals indicative of chest compression parameters, ventilation parameters, drug delivery parameters, fluid delivery parameters, etc.

In addition to delivering therapy to the patient, the therapy delivery component(s) 261*a* can include, be coupled to, and/or function as sensors and provide signals indicative of sensor data (e.g., second sensor data) to the medical device 1102. For example, the defibrillation electrodes can be configured as cardiac sensing electrodes as well as electro-therapy delivery devices and can provide signals indicative of transthoracic impedance, electrocardiogram (ECG), heart rate and/or other physiological parameters. As another example, a therapeutic cooling device can be an intravenous cooling device. Such a cooling device can include an intra-venous (IV) device as a therapy delivery component configured to deliver cooling therapy and sense the patient's temperature. For example, the IV device can be a catheter that includes saline balloons configured to adjust the patient's temperature via circulation of temperature controlled saline solution. In addition, the catheter can include a temperature probe configured to sense the patient's temperature. As a further example, an IV device can provide therapy via drug delivery and/or fluid management. The IV device can also monitor and/or enable monitoring of a patient via blood sampling and/or venous pressure monitoring (e.g., central venous pressure (CVP) monitoring).

The medical device 1102 can be configured to receive the sensor signals (e.g., from the therapy delivery component(s) 261*a* and/or the sensor(s) 261*b*) and to process the sensor signals to determine and collect the patient data. The patient data can include patient data which can characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infra-red Spectroscopy (NIRS) measurements, etc.). Additionally or alternatively, the patient data can characterize the delivery of therapy (e.g., chest compression data such as compression depth, compression rate, etc.) and/or the patient data can characterize a status and/or condition of the medical equipment used to treat the patient (e.g., device data such as shock time, shock duration, attachment of electrodes, power-on, etc.).

The components of 220, 221, 230, 244, 245, and 255 of the medical device 1102 are communicatively coupled (directly and/or indirectly) to each other for bi-directional communication.

Although shown as separate entities in FIG. 10, the one or more of the components of the medical device 1102 can be combined into one or more discrete components and/or can be part of the processor 220. The processor 220 and the memory 221 can include and/or be coupled to associated circuitry to perform the functions described herein.

In an implementation, the medical device 1102 can be a therapeutic medical device configured to deliver medical therapy to the patient. Thus, the medical device 1102 can optionally include the therapy delivery control module 255. For example, the therapy delivery control module 255 can be an electrotherapy delivery circuit that includes one or more capacitors configured to store electrical energy for a pacing pulse or a defibrillating pulse. The electrotherapy delivery circuit can further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 255 can be a compression device such as an electro-mechanical controller configured to control a mechanical compression device. As a further example, the therapy delivery control module 255 can be an electro-mechanical controller configured to control drug delivery, temperature management, ventilation, and/or other type of therapy delivery. Alternatively, some examples of the medical device 1102 may not be configured to deliver medical therapy to the patient 104 but can be configured to provide patient monitoring and/or diagnostic care. As shown in FIG. 10, in some examples, the therapy delivery control module 255 exchanges messages 1180 with the mobile computing device 1104 (e.g., the patient mobile computing device). These messages can include patient data descriptive of therapy provided to the patient or other patient data stored on the medical device 1102.

The medical device 1102 can incorporate and/or be configured to couple to one or more patient interface device(s) 190. The patient interface device(s) 190 can include one or more therapy delivery component(s) 261*a* and one or more sensor(s) 261*b*. The one or more therapy delivery component(s) 261*a* and the one or more sensor(s) 261*b* can provide one or more signals to the medical device 1102 via wired and/or wireless connection(s).

The one or more therapy delivery component(s) 261*a* can include electrotherapy electrodes (e.g., the electrotherapy electrodes 266*a*), ventilation device(s) (e.g., the ventilation devices 266*b*), intravenous device(s) (e.g., the intravenous devices 266*c*), compression device(s) (e.g., the compression devices 266*d*), etc. For example, the electrotherapy electrodes can include defibrillation electrodes, pacing electrodes, and/or combinations thereof. The ventilation devices can include a tube, a mask, an abdominal and/or chest compressor (e.g., a belt, a cuirass, etc.), etc. and combinations thereof. The intravenous devices can include drug delivery devices, fluid delivery devices, and combinations thereof. The compression devices can include mechanical compression devices such as abdominal compressors, chest compressors, belts, pistons, and combinations thereof. In various implementations, the therapy delivery component(s) 261*a* can be configured to provide sensor data and/or be coupled to and/or incorporate sensors. For example, the electrotherapy electrodes can provide sensor data such as transthoracic impedance, ECG, heart rate, etc. Further the electrotherapy electrodes can include and or be coupled to a chest compression sensor. As another example, the ventilation devices can be coupled to and/or incorporate flow sensors, gas species sensors (e.g., oxygen sensor, carbon dioxide sensor, etc.), etc. As a further example, the intravenous devices can be coupled to and/or incorporate temperature sensors, flow sensors, blood pressure sensors, etc. As yet another example, the compression devices can be coupled to and/or incorporate chest compression sensors, patient position sensors, etc. The therapy delivery control module 255 can be configured to couple to and control the therapy delivery component(s) 261*a*.

In various implementations, the sensor(s) 261*b* can include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos can be two-dimensional or three-dimensional.

The sensor(s) 261*b* can include sensing electrodes (e.g., the sensing electrodes 262), ventilation sensors (e.g., the ventilation sensors 264), temperature sensors (e.g., the temperature sensor 267), chest compression sensors (e.g., the chest compression sensor 268), etc. For example, the sensing electrodes can include cardiac sensing electrodes. The cardiac sensing electrodes can be conductive and/or capacitive electrodes configured to measure changes in a patient's electrophysiology, for example to measure the patient's ECG information. In an implementation, the sensing electrodes can be configured to measure the transthoracic impedance and/or a heart rate of the patient. The ventilation sensors can include spirometry sensors, flow sensors, pressure sensors, oxygen and/or carbon dioxide sensors such as, for example, one or more of pulse oximetry sensors, oxygenation sensors (e.g., muscle oxygenation/pH), O2 gas sensors and capnography sensors, and combinations thereof. The temperature sensors can include an infrared thermometer, a contact thermometer, a remote thermometer, a liquid crystal thermometer, a thermocouple, a thermistor, etc. and can measure patient temperature internally and/or externally. The chest compression sensor can include one or more motion sensors including, for example, one or more accelerometers, one or more force sensors, one or more magnetic sensors, one or more velocity sensors, one or more displacement sensors, etc. The chest compression sensor can be, for example, but not limited to, a compression puck, a smart phone, a hand-held device, a wearable device, etc. The chest compression sensor can be configured to detect chest motion imparted by a healthcare provider and/or an automated chest compression device (e.g., a belt system, a piston system, etc.). The chest compression sensor can provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes can include or be configured to couple to the chest compression sensor.

Continuing with FIG. 10, examples of components of the mobile computing device 1104 are shown schematically. In an implementation, the mobile computing device 1104 can include a processor 420, a memory 421, one or more output devices 430, one or more user input devices 447, and a communications interface 445. FIG. 10 also illustrates schematically examples of components of the remote computing device 1106. As shown in FIG. 10, the remote computing device 1106 can include a processor 1320, a memory 321, one or more output devices 330, one or more user input devices 344, and a communications interface 345. FIG. 10 further illustrates schematically examples of components of the server(s) 1108. As shown in FIG. 10, the server(s) 1108 can include a processor 1520, a memory 521, one or more output devices 531, one or more user input devices 544, and a communications interface 545.

Each of the mobile computing device 1104 and the remote computing device 1106 can be a computer system, such as a desktop, notebook, mobile, portable, or other type of computing system. Each of these devices 1104 and 1106 can include server(s) and/or access server(s) via a monitor and/or other connected user interface device. Although described as server(s), the server(s) 1108 can be another type of computing system including for example a desktop, notebook, mobile, portable, or other type of computing system.

As shown in FIG. 10, each of the devices 1104 and 1106, along with the server(s) 1108 and the medical device 1102, includes a bus or other interconnection mechanism that communicably couples the processor, memory, output devices, input devices, and communication interface included therein. The bus can include a PCI/PCI-X or SCSI based system bus depending on the storage devices used, for example.

The processors 220, 1320, 420, and 1520 can each include a processor, such as, but not limited to, an Intel® Itanium® or Itanium 2® processor(s), or AMD® Opteron® or Athlon MP® processor(s), or Motorola® lines of processors. The communication interfaces 245, 345, 445, and 545 can each be any of an RS-232 port for use with a modem-based dialup connection, a 10/100 Ethernet port, or a Gigabit port using copper or fiber, for example. The communication interfaces 245, 345, 445, and 545 may be chosen depending on a network(s) such a Local Area Network (LAN), Wide Area Network (WAN), or any network to which the medical device 1102, the mobile computing device 1104, the remote computing device 1106, and/or the server(s) 1108 may connect. The memories 221, 321, 421, and 521 can be Random Access Memory (RAM), Read Only Memory (ROM), Flash memory, and/or another dynamic volatile and/or non-volatile storage device(s). The memories 221, 321, 421, and 521 can be used to store information and instructions. For example, hard disks such as the Adaptec® family of SCSI drives, an optical disc, an array of disks such as RAID (e.g. the Adaptec family of RAID drives), or any other mass storage devices may be used. The components described above are meant to exemplify some types of possibilities. In no way should the aforementioned examples limit the scope of the disclosure. The memories 221, 321, 421, and 521 can further include removable storage media such as external hard-drives, floppy drives, flash drives, IOMEGA® Zip Drives, Compact Disc-Read Only Memory (CD-ROM), Compact Disc-Re-Writable (CD-RW), or Digital Video Disk-Read Only Memory (DVD-ROM), for example.

Continuing with FIG. 10, the server(s) 1108 can include, for example, the one or more storage server(s) and one or more application server(s). In some examples, the server(s) 1108 are configured to exchange messages 1170 with the remote computing device 1106. These messages can include sensor and/or treatment data as described above. In some examples, the server(s) 1108 are configured to exchange messages 1190 with the medical device 1102. These messages can include data descriptive of a patient (e.g., the patient 104 of FIG. 1) being treated via the medical device and/or treatment being delivered by the medical device 1102.

Some examples of the present disclosure include various steps, some of which can be performed by hardware components or can be embodied in machine-executable instructions. These machine-executable instructions can be stored on a non-transitory data storage medium and can be used to cause a general-purpose or a special-purpose processor programmed with the instructions to perform the steps. The non-transitory data storage medium can further store an operating system and the machine-executable instructions can be included within one or more software applications or programs. These programs can implement the features disclosed herein and the methods that they execute. Alternatively, the steps can be performed by a combination of hardware, software, and/or firmware, on one device and/or distributed across multiple devices and/or processors. In addition, some examples of the present disclosure can be performed or implemented, at least in part (e.g., one or more modules), on one or more computer systems, mainframes (e.g., IBM mainframes such as the IBM zSeries, Unisys ClearPath Mainframes, HP Integrity NonStop server(s), NEC Express series, and others), or client-server type systems. In addition, specific hardware aspects of examples of the present disclosure can incorporate one or more of these systems, or portions thereof.

Figure 11:
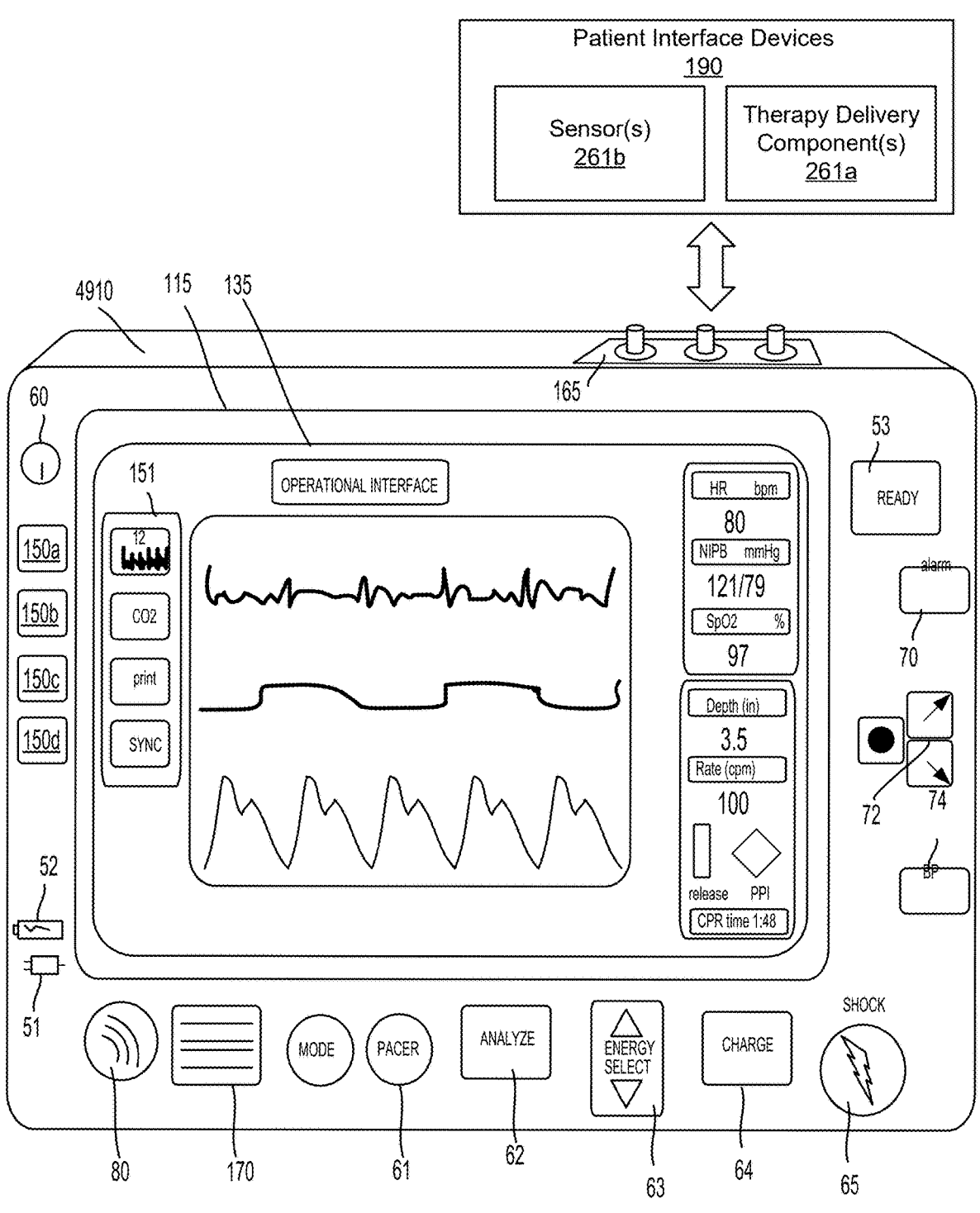
FIG. 11 is a schematic block diagram of a defibrillator in accordance with at least one example disclosed herein.

Referring to FIG. 11, an example of the medical device 1102 of FIG. 10 with an operational interface is shown. This example, the medical device 4910, is a patient monitor/defibrillator. This configuration of a medical device is an example only and not limiting of the disclosure. In various implementations, the medical device 4910 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 4910 may be an integrated therapy delivery/monitoring device that includes a single housing. The single housing may surround, at least in part, the therapy delivery components and the monitoring components. In an implementation, the medical device 4910 may be a modular therapy delivery/monitoring device.

The medical device 4910 may include one or more output or input/output devices, for example, a display screen 115. A processor of the medical device 4910 may control the display screen 115 to selectively display the operational interface 135. The operational interface 135 as shown in FIG. 11 is an example only and elements may be rearranged, combined, altered, or deleted. As discussed in further detail below, selective display refers to the ability of the processor to select amongst various available display modes which may include an operational interface only display mode.

The operational interface 135 may provide patient data received by the medical device 4910 from the patient interface device(s) 190 (e.g., the therapy delivery component(s) 261a and/or from the sensor(s) 261b). For example, the medical device 4910 may be configured to couple to the patient interface device(s) 190 via the one or more connection ports 165. The operational interface 135 may provide the patient data in real-time as the signals are received and processed by the processor 220 of the medical device 4910.

The therapy delivery component(s) 261a are configured to deliver therapy to the patient and may be configured to couple to the patient. For example, the therapy delivery component(s) 261a may include one or more of electro-therapy electrodes including defibrillation electrodes and/or pacing electrodes, chest compression devices, ventilation devices, drug delivery devices, etc. In addition to delivering therapy to the patient, the therapy delivery component(s) 261a may include, be coupled to, and/or function as sensors and provide signals indicative of sensor data (e.g., first sensor data) to the medical device 4910. For example, the therapy delivery component(s) 261a may be defibrillation and/or pacing electrodes and may provide signals indicative of transthoracic impedance, ECG, heart rate and/or other physiological parameters.

The sensor(s) 261b are configured to provide signals indicative of sensor data (e.g., second sensor data) to the medical device 4910. The sensor(s) 261b may be configured to couple to the patient. For example, the sensor(s) 261b may include cardiac sensing electrodes, a chest compression sensor, and/or ventilation sensors.

The medical device 4910 may be configured to receive the sensor signals (e.g., from the therapy delivery component(s) 261a and/or the sensor(s) 261b) indicative of patient data for the patient and configured to process the sensor signals to determine and collect the patient data. The patient data may include patient data which may characterize a status and/or condition of the patient (e.g., physiological data such as ECG, heart rate, pulse oximetry, non-invasive hemoglobin parameters, capnography, oxygen and $CO2$ concentrations in the airway, invasive and non-invasive blood pressures, tissue pH, tissue oxygenation, near infra-red spectroscopy, etc.). Additionally or alternatively, the patient data may characterize the delivery of therapy (e.g., chest compression data such as compression depth, compression rate, etc.) and/or the patient data may characterize a status and/or condition of the medical equipment used to treat the patient (e.g., device data such as shock time, shock duration, attachment of electrodes, power-on, etc.).

In addition to the display screen 115, the medical device 4910 may include one or more other output devices such as, for example, a speaker 170. The processor 220 may be configured to control the speaker 170 to provide audible instructions, a metronome (e.g., a chest compression metronome), feedback, and/or physiological information for a user of the medical device 4910. The medical device 4910 may further include device status indicators and/or device operation controls. For example, device status indicators may include a power-on indicator 51, a battery charge indicator 52, and/or a device ready indicator 53. The device operation controls may include a power-on control 60, a pacer mode control 61, a heart rhythm analyze control 62, a defibrillation energy selection control 63, a charge control 64, a shock delivery control 65, an alarm control 70, one or more display navigation controls 72, and a sensor control 74. Activation of the sensor control 74 may cause an associated patient data sensor to capture patient data and provide the data to the medical device 4910. The display screen 115 may provide the captured patient data. For example, activation of the sensor control 74 may cause a blood pressure sensor to measure the patient's blood pressure and may cause the operational interface 135 to display the measured blood pressure in response to activation of the sensor control 74. The medical device 4910 may include one or more soft-keys 150a, 150b, 150c, 150d, one or more soft-key labels 151, and/or an NFC tag 80. The NFC tag 80 may enable the medical device 4910 to communicatively couple with another device, such as the mobile computing device 1104.

Having thus described several aspects of at least one example, it is to be appreciated that various alterations, modifications, and improvements will readily occur to those skilled in the art. For instance, examples disclosed herein can also be used in other contexts. Such alterations, modifications, and improvements are intended to be part of this disclosure and are intended to be within the scope of the examples discussed herein. Accordingly, the foregoing description and drawings are by way of example only.

The invention claimed is:

1. An external defibrillator comprising:
therapy delivery circuitry configured to discharge electrotherapy to a patient;
at least one chest compression sensor configured to acquire motion signals during and after administration of cardiopulmonary resuscitation (CPR) to the patient;
at least one electrocardiogram (ECG) sensor configured to acquire ECG signals from the patient; and
at least one processor coupled to the therapy delivery circuitry, the at least one chest compression sensor, and the at least one ECG sensor and configured to:
generate first ECG data from ECG signals acquired during a cycle of CPR, generate second ECG data from ECG signals acquired after the cycle of CPR, identify a plurality of temporally overlapping segments in the first ECG data, analyze the plurality of temporally overlapping segments in the first ECG data to determine an initial shock/no-shock decision that is based on the ECG signals acquired during the cycle of CPR, use the first ECG data to select a particular reconfirmation time period, identify one or more segments of the second ECG data, each having a duration equal to the particular reconfirmation time period, confirm the initial shock/no-shock decision using the identified one or more segments of the second ECG data having the duration equal to the particular reconfirmation time period, and control the therapy delivery circuitry to discharge the electrotherapy where the initial shock/no-shock decision is confirmed to specify the electrotherapy.

2. The external defibrillator of claim 1, wherein to determine the initial shock/no-shock decision comprises to analyze each segment of the plurality of temporally overlapping segments to:

derive at least one feature from the segment;

determine whether the at least one feature meets at least one criterion of a plurality of criteria, each criterion of the plurality of criteria specifying one or more constraints on one or more features of an ECG signal acquired during the cycle of CPR; and increment at least one counter associated with the at least one criterion where the at least one feature meets the at least one criterion.

3. The external defibrillator of claim 2, wherein the at least one feature specifies at least one attribute of an ECG waveform specified in the segment.

4. The external defibrillator of claim 3, wherein the at least one attribute is one or more of waveform slope, waveform amplitude, waveform frequency, QRS width, QRS rate, or QRS variation.

5. The external defibrillator of claim 2, wherein the plurality of criteria comprises at least one criterion associated with noise.

6. The external defibrillator of claim 5, wherein the at least one processor is further configured to determine whether the noise is reducible via settling time.

7. The external defibrillator of claim 1, wherein a first segment of the plurality of temporally overlapping segments spans a duration different from a duration of a second segment of the plurality of temporally overlapping segments.

8. The external defibrillator of claim 1, wherein at least two segments of the plurality of temporally overlapping segments span an equal duration.

9. The external defibrillator of claim 1, wherein a first segment of the plurality of temporally overlapping segments comprises an overlapping portion sharing a period of time with a second segment of the plurality of temporally overlapping segments and a non-overlapping portion distinct from the overlapping portion.

10. The external defibrillator of claim 1, wherein a first segment of the plurality of temporally overlapping segments spans 3 seconds and comprises an overlapping portion spanning 2.5 seconds.

11. The external defibrillator of claim 1, wherein the one or more segments of the second ECG data are temporally overlapping segments.

12. The external defibrillator of claim 11, wherein to confirm the initial shock/no-shock decision comprises to analyze a particular segment of the second ECG data identified as having the duration equal to the particular reconfirmation time period to:

derive at least one feature from the particular segment;

determine whether the at least one feature meets at least one criterion specifying one or more constraints on one or more features of an ECG signal acquired after the cycle of CPR; and confirm the initial shock/no-shock decision where the at least one feature meets the at least one criterion.

13. The external defibrillator of claim 1, wherein to confirm the initial shock/no-shock decision comprises to analyze each segment of the second ECG data identified as having the duration equal to the particular reconfirmation time period to:

derive at least one feature from the segment;

determine whether the at least one feature meets at least one criterion specifying one or more constraints on one or more features of an ECG signal acquired after the cycle of CPR; and confirm the initial shock/no-shock decision where the at least one feature meets the at least one criterion.

14. The external defibrillator of claim 13, wherein the particular reconfirmation time period is 1 second or 2 seconds.

15. The external defibrillator of claim 1, wherein the initial shock/no-shock decision specifies the electrotherapy or continued CPR.

16. The external defibrillator of claim 1, the at least one processor being further configured to:

one or more of:

determine at least one impedance measurement based on an impedance detection signal acquired after the cycle of CPR; or determine at least one acceleration measurement based on motion signals acquired after the cycle of CPR; and determine, based on one or more of the at least one impedance measurement or the at least one acceleration measurement, whether the second ECG data comprises noise sufficient to prevent confirmation.

17. The external defibrillator of claim 16, wherein the at least one impedance measurement comprises a plurality of impedance measurements, and to determine whether the second ECG data comprises noise sufficient to prevent confirmation comprises to:

derive at least one standard deviation measurement for the plurality of impedance measurements;

compare the at least one standard deviation measurement to at least one threshold value; and determine that the second ECG data comprises noise sufficient to prevent confirmation where the at least one standard deviation measurement transgresses the at least one threshold value and an amplitude specified within the second ECG data transgresses a threshold amplitude value.

18. The external defibrillator of claim 16, wherein to determine whether the second ECG data comprises noise sufficient to prevent confirmation comprises to:

determine whether the second ECG data indicates saturation; and determine that the second ECG data comprises noise sufficient to prevent confirmation where the second ECG data indicates saturation.

19. The external defibrillator of claim 16, wherein the at least one impedance measurement comprises a plurality of impedance measurements, and to determine whether the second ECG data comprises noise sufficient to prevent confirmation comprises to:

determine that the second ECG data does not indicate saturation;

derive at least one standard deviation measurement for the plurality of impedance measurements;

compare the at least one standard deviation measurement to at least one threshold value;

determine that the at least one standard deviation measurement transgresses the at least one threshold value;

determine whether an amplitude specified within the second ECG data transgresses a threshold amplitude value; and determine that the second ECG data comprises noise sufficient to prevent confirmation where the at least one standard deviation measurement transgresses the at least one threshold value and the amplitude transgresses the threshold amplitude value.

20. The external defibrillator of claim 16, wherein the at least one acceleration measurement comprises a plurality of acceleration measurements, and to determine whether the second ECG data comprises noise sufficient to prevent confirmation comprises to:

derive at least one standard deviation measurement for the plurality of acceleration measurements;

compare the at least one standard deviation measurement to at least one threshold value; and determine that the second ECG data comprises noise sufficient to prevent confirmation where the at least one standard deviation measurement transgresses the at least one threshold value and an amplitude specified within the second ECG data transgresses a threshold amplitude value.

21. The external defibrillator of claim 18, wherein the at least one acceleration measurement comprises a plurality of acceleration measurements, and to determine whether the second ECG data comprises noise sufficient to prevent confirmation comprises to:

determine that the second ECG data does not indicate saturation;

derive at least one standard deviation measurement for the plurality of acceleration measurements;

compare the at least one standard deviation measurement to at least one threshold value;

determine that the at least one standard deviation measurement transgresses the at least one threshold value;

determine whether an amplitude specified within the second ECG data transgresses a threshold amplitude value; and determine that the second ECG data comprises noise sufficient to prevent confirmation where the at least one standard deviation measurement transgresses the at least one threshold value and the amplitude transgresses the threshold amplitude value.

\*    \*    \*    \*    \*